US007595397B2

(12) United States Patent
Zindell et al.

(10) Patent No.: US 7,595,397 B2
(45) Date of Patent: Sep. 29, 2009

(54) COMPOUNDS WHICH MODULATE THE CB2 RECEPTOR

(75) Inventors: Renee Zindell, New Milford, CT (US); Doris Riether, New York, NY (US); David S. Thomson, Ridgefield, CT (US); Eugene Richard Hickey, Danbury, CT (US); Innocent Mushi, Oxford (GB); Monika Ermann, Wantage (GB)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 290 days.

(21) Appl. No.: 11/608,537

(22) Filed: Dec. 8, 2006

(65) Prior Publication Data
US 2007/0191340 A1  Aug. 16, 2007

Related U.S. Application Data

(60) Provisional application No. 60/750,638, filed on Dec. 15, 2005.

(51) Int. Cl.
C07D 265/30 (2006.01)
A61K 31/5355 (2006.01)
(52) U.S. Cl. .................................. 544/106; 514/239.5
(58) Field of Classification Search .................. 544/106
See application file for complete search history.

(56) References Cited

U.S. PATENT DOCUMENTS

| 5,256,658 | A | * | 10/1993 | Hsi et al. ................. 514/236.2 |
| 5,428,037 | A | | 6/1995 | Pascal et al. |
| 5,847,153 | A | | 12/1998 | Warpehoski et al. |
| 5,968,929 | A | | 10/1999 | Blythin et al. |
| 6,057,371 | A | | 5/2000 | Glennon |
| 6,414,011 | B1 | | 7/2002 | Hogenkamp et al. |
| 6,437,177 | B1 | | 8/2002 | Warpehoski et al. |
| 6,528,529 | B1 | | 3/2003 | Brann et al. |
| 6,610,711 | B2 | | 8/2003 | Armer et al. |
| 6,737,418 | B2 | | 5/2004 | Hogenkamp et al. |
| 2002/0099035 | A1 | | 7/2002 | Sandanayaka et al. |
| 2004/0242913 | A1 | | 12/2004 | Ducray et al. |
| 2007/0021430 | A1 | | 1/2007 | Abouabdellah et al. |

FOREIGN PATENT DOCUMENTS

| EP | 0 970 046 B1 | 10/2003 |
| EP | 0 929 519 B1 | 2/2005 |
| FR | 2866885 A1 | 2/2004 |
| WO | WO 98/13340 | 4/1998 |
| WO | 01 29007 A1 | 4/2001 |
| WO | 02 062750 A1 | 8/2002 |
| WO | WO 03/055482 | 7/2003 |
| WO | 2004 018433 A1 | 3/2004 |
| WO | WO 2004/050643 | 6/2004 |
| WO | 2004060882 A1 | 7/2004 |
| WO | WO 2005/040355 | 5/2005 |
| WO | WO 2006/012227 | 2/2006 |
| WO | 2006 060461 A1 | 6/2006 |

OTHER PUBLICATIONS

RN 57992-82-2, retrieved from CAPLUS on Jan. 2, 2009.*
RN 112298-90-5, retrieved from CAPLUS on Jan. 2, 2009.*
RN 262371-16-4, retrieved from CAPLUS on Jan. 2, 2009.*
Johansen et al.; AMPA Receptor Agonists: Resolution, Configurational Assignment, and Pharmacology of (+)-(S)- and (−)-(R)-2-Amino-3-(3-Hydroxy-5-(2-Pyridyl) Isoxazol-4-yl)Propionic Acid (2-Py-AMPA); Chirality, New York, 1997; vol. 9, No. 3; pp. 274-280.
Gavalda et al.; N-Sulfonyl hydroxamate derivatives as inhibitors of class II fructose-1,6-diphosphate aldolase; Bioorganic & Medicinal Chemistry Letter, 2005; vol. 15, No. 24; pp. 5375-5377.
Mohler et al.; Nonsteroidal tissue selective androgen receptor modulators: a promising class of clinical candidates; University of Tennessee Health Science Center; Expert Opinion of Therapeutic Patents; Nov. 2005; vol. 15, No. 11; pp. 1565-1585.
St. Goldschmidt, et al., "Biphenyl derivatives II. Basic 4-Biphenyl Compounds". Receuil Travaux Chimiques Des Pays-Bas, vol. 69, 1950, pp. 1109-1117.
D. Chen, et al., "Preparation, properties, and synthetic potentials of novel boronates in a flourous version (flourous boronates)". Organic Letters, vol. 4. No. 6, 2002, pp. 1003-1005.
O.V. Miroshnikova, et al., "Structure-activity relationships in the series of eremomycin carboxamides". Journal of Antibiotics, vol. 53, No. 3, 2000, pp. 286-293.
J. Balzarini, et al., "Antiretroviral activity of semisynthetic derivatives of glycopeptide antibiotics". J. Med. Chem., 2003, vol. 46, No. 13, pp. 2755-2764.
J. L. Herndon, et al., "Ketanserin analogues. Structure-affinity relationships for 5-HT2 and 5-HT1c serotoninin receptor binding". J. Med. Chem, 1992, vol. 35, No. 26, pp. 4903-4910.
K. Audouze, et al., "New series of morpholine and 1,4-oxazepane derivatives as dopamine D4 receptor ligands. Synthesis and 3D-QSAR model." J. Med. Chem, vol. 47, No. 12, pp. 3089-3104.
L. Revesz, et al., "Novel CCR1 antagonists with oral activity in the mouse collagen induced arthritis". Bioorganic and Medicinal Chemistry Letters, vol. 15, 2005, pp. 5160-5164.

(Continued)

Primary Examiner—Rei-Tsang Shiao
Assistant Examiner—Shawquia Young
(74) Attorney, Agent, or Firm—Michael P. Morris; Mary-Ellen M. Devlin; Anthony P. Bottino

(57) ABSTRACT

Compounds are provided which bind to and are agonists, antagonists or inverse agonists of the CB2 receptor, the compounds having the general formula

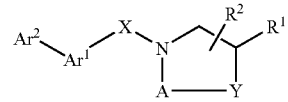

wherein, $R^1$, $R^2$, A, Y, X, $Ar^1$ and $Ar^2$ have the meanings given in the specification, and the preparation and use thereof. The compounds are valuable CB2 receptor modulators.

4 Claims, No Drawings

OTHER PUBLICATIONS

M. T. Leffler, et al. "N-Arylalkylmorpholines". Journal of the American Chemical Society, vol. 60, 1938, pp. 896-899.

R. Baltzly, et al., "Unsymmetrically substituted piperazines. V. Piperazine ureas". The Journal of the American Chemical Society, vol. 76, 1954, pp. 1165-1166.

R. Baltzly, et al., "The preparation of N-mono-substituted and unsymmetrically disubstituted piperzines". Journal of American Chemical Society, vol. 66, 1944, pp. 263-265.

C. B. Pollard, et al., "Some amides of piperazines". Journal of American Chemical Society, vol. 75, 1953, p. 491.

R. E. Lutz, et al., "Antimalarials. Some piperazine derivatives". Journal of Organic Chemistry, vol. 12, 1947, pp. 771-775.

R. A. Dav, Jr., et al., "Polarography of phenyl 2-thienyl and 2,2'-dithienyl ketones". 1953.

* cited by examiner

COMPOUNDS WHICH MODULATE THE CB2 RECEPTOR

CROSS REFERENCE TO RELATED APPLICATIONS

This application claims the benefit of U.S. Provisional Patent Application No. 60/750,638, filed Dec. 15, 2005 entitled "Compounds Which Modulate The CB2 Receptor," the disclosure of which is hereby incorporated by reference in its entirety.

BACKGROUND OF THE INVENTION

1. Technical Field

The present invention relates to novel compounds which modulate the CB2 receptor and their use as medicaments.

2. Background Information

Cannabinoids are a group of about 60 distinct compounds found in *Cannabis sativa* (also know as marijuana) with cannabinol, cannabidiol and $\Delta^9$-tetrahydrocannabinol (THC) being the most representative molecules. The therapeutic usage of *Cannabis* can be dated back to ancient dynasties of China and includes applications for various illnesses ranging from lack of appetite, emesis, cramps, menstrual pain, spasticity to rheumatism. The long history of *Cannabis* use has led to the development of several pharmaceutical drugs. For example, Marinol and Cesamet which are based on THC and its analogous nabilone, respectively, are used as anti-emetic and appetite stimulant. Despite of the clinical benefits, the therapeutic usage of cannabis is limited by its psychoactive effects including hallucination, addiction and dependence. Mechoulam R, ed. *Cannabinoids as Therapeutic Agents*, Boca Raton, Fla.; CRC Press, 1986 provides a review of the medicinal use of cannabis.

The physiological effects of cannabinoids are mediated by at least two G-protein coupled receptors, CB1 and CB2. Autoradiographic studies have demonstrated that CB1 receptors are expressed primarily in the central nervous system, specifically in the cerebral cortex, hippocampus, basal ganglia and cerebellum. They are also found in the reproductive system and other peripheral tissues including that of the immune system, but to a lesser degree. CB1 receptors regulate the release of neurotransmitters from the pre-synaptic neurons and are believed to mediate most of the euphoric and other central nervous system effects of cannabis, such as THC-induced ring-catalepsy, hypomobility, and hypothermia, which were found to be completely absent in mice with a deletion of the CB1 gene (Zimmer et al., Increased mortality, hypoactivity, and hypoalgesia in cannabinoid CB1 receptor knockout mice. Proc Natl Acad Sci USA. (1999) 96:5780-5785.)

CB2 receptors are almost exclusively found in the immune system, with the greatest density in the spleen. It is estimated that the expression level of CB2 in the immune cells is about 10 to 100 times higher than CB1. Within the immune system, CB2 is found in various cell types, including B cells, NK cells, monocytes, microglial cells, neutrophils, T cells, dentritic cells and mast cells, suggesting that a wide range of immune functions can be regulated through CB2 modulators (Klein et al., The cannabinoid system and immune system. J Leukoc Biol (2003) 74:.486-496). This is supported by the finding that the immunomodulatory effect of THC is absent in CB2 deficient mice (Bicklet et al., Immunomodulation by cannabinoid is absent in mice deficient for the cannabinoid CB2 receptor. Eur J Pharmacol (2000) 396:141-149). CB2 selective ligands have been developed and tested for their effects in various imflammatory settings. For example, in animal models of inflammation, CB2 selective agonists, inverse agonists and antagonists have been shown to be effective in suppressing inflammation (Hanus et al., HU-308: a specific agonist for CB(2), a peripheral cannabinoid receptor. Proc Natl Acad Sci USA. (1999) 96:14228-14233, Ueda et al., Involvement of cannabinoid CB(2) receptor-mediated response and efficacy of cannabinoid CB(2) receptor inverse agonist, JTE-907, in cutaneous inflammation in mice. Eur J. Pharmacol. (2005) 520:164-171 and Smith et al., The anti-inflammatory activities of cannabinoid receptor ligands in mouse peritonitis models Eur J Pharmacol. (2001) 432:107-119.). Furthermore, CB2 selective agonists inhibit disease severity and spasticity in animal models for multiple sclerosis (Baker et al., Cannabinoids control spasticity and tremor in a multiple sclerosis model. Nature (2000) 404:84-87. Arevalo-Martin et al., Therapeutic action of cannabinoids in a murine model of multiple sclerosis J Neurosci. (2003) 23:2511-2516.). Taken together, these results support the notion that CB2 receptor modulators can be employed for the treatment of medical conditions having an inflammatory component.

In addition to inflammation, CB2 agonists have been shown to inhibit pain and emesis. For instance, CB2 selective agonists blunt the pain response induced by thermal or other stimuli (Malan et al., CB2 cannabinoid receptor-mediated peripheral antinociception. Pain. (2001) 93:239-45 and Nackley et al., Selective activation of cannabinoid CB(2) receptors suppresses spinal fos protein expression and pain behavior in a rat model of inflammation. Neuroscience (2003) 119:747-57.) CB2 activation has also been demonstrated to inhibit neuropathic pain response (Ibrahim et al., Activation of CB2 cannabinoid receptors by AM1241 inhibits experimental neuropathic pain: pain inhibition by receptors not present in the CNS. Proc Natl Acad Sci USA. (2003) 100:10529-33.) Finally, in contrast to the earlier data which did not find CB2 in the brain, a recent article demonstrated the expression of CB2 in the brain, at about 1.5% of the level in the spleen. CB2 activation is shown by this article to be responsible for the anti-emetic effect of endocannabinoid (Van Sickle et al., Identification and functional characterization of brainstem cannabinoid CB2 receptors. Science. 2005 310:329-332.) The foregoing results confirm that CB2 agonists can be used for the treatment of inflammatory and neuropathic pain as well as emesis.

BRIEF SUMMARY OF THE INVENTION

The present invention provides novel compounds which bind to and are agonists, antagonists or inverse agonists of the CB2 receptor. The invention also provides a method and pharmaceutical compositions for treating inflammation by way of the administration of therapeutic amounts of these compounds. Lastly, the invention provides a method and pharmaceutical compositions for treating pain by way of the administration of therapeutic amounts of a subset of the new compounds which are CB2 agonists.

DETAILED DESCRIPTION OF THE INVENTION

In its broadest generic aspect the invention provides compounds of the formula

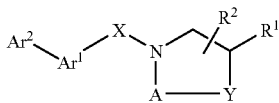
(I)

wherein, $R^1$ is hydrogen, $C_1$-$C_6$ alkyl optionally substituted with aryl or heteroaryl, $C_3$-$C_{10}$ cycloalkyl, optionally substituted aryl, optionally substituted heteroaryl; or, $R^1$ is $C_1$-$C_3$ alkyl substituted with Z-$R^6$, wherein Z is O, S, $SO_2$, NH, NMe or $CH_2$ and $R^6$ is optionally substituted aryl or heteroaryl, provided that Y is O or $NR^3$ and n is 2 or 3;

$R^2$ is hydrogen or $C_1$-$C_6$ alkyl;

A is a group of the formula —$(CH_2)_n$— wherein n is 1, 2 or 3, which is optionally substituted with one or two $C_1$-$C_6$ alkyl groups;

Y is a methylene group, provided that n is 1, 2 or 3, wherein said methylene group is optionally substituted with a halogen atom or with a $C_1$-$C_6$ alkyl group (which, in turn, is optionally substituted with one to three halogen atoms); or, Y is selected from the group consisting of O and $NR^3$, provided that n is 2 or 3, wherein, $R^3$ is hydrogen, $C_1$-$C_6$ alkyl (optionally substituted by one to 3 halogen atoms), $C_3$-$C_6$ cycloalkyl, phenyl, benzyl, pyridyl, C(O)$R^4$, $SO_2R^4$, C(O)NH$R^4$, or C(O)NMe$R^4$, wherein, $R^4$ is hydrogen, $C_1$-$C_6$ alkyl (optionally substituted by one to 3 halogen atoms), $C_3$-$C_6$ cycloalkyl, phenyl, benzyl or pyridyl; or, Y is selected from the group consisting of S, SO and $SO_2$, provided that n is 2;

X is a methylene group (which is optionally mono- or disubstituted with methyl) or a carbonyl group;

$Ar^1$ is a divalent moiety which is either phenylene or a six-membered heteroarylene, which divalent moiety is optionally mono- or disubstituted with moieties selected from the group consisting of $C_1$-$C_6$ alkyl (optionally substituted by one to 3 halogen atoms), $C_3$-$C_{10}$ cycloalkyl and halogen; and, $Ar^2$ is an aryl or heteroaryl moiety which is optionally substituted with $C_1$-$C_6$ alkyl (which is optionally substituted with 1 to 3 halogen atoms), $C_1$-$C_6$ alkoxy (which is optionally substituted with 1 to 3 halogen atoms), $C_1$-$C_6$ alkylthio, $C_1$-$C_6$ alkoxycarbonyl, $C_1$-$C_6$ alkylaminocarbonyl, $C_1$-$C_6$ dialkylaminocarbonyl, hydroxyl, halogen, cyano or nitro.

In a first subgeneric aspect, the invention provides compounds of the formula I wherein, $R^1$ is hydrogen, $C_1$-$C_6$ alkyl, $C_3$-$C_{10}$ cycloalkyl, phenyl, benzyl or pyridyl;

$R^2$ is hydrogen or $C_1$-$C_6$ alkyl;

A is a group of the formula —$(CH_2)_n$— wherein n is 1, 2 or 3, which is optionally substituted with one or two $C_1$-$C_6$ alkyl groups;

Y is a methylene group, provided that n is 1, 2 or 3, wherein said methylene group is optionally substituted with a halogen atom or with a $C_1$-$C_6$ alkyl group (which, in turn, is optionally substituted with one to three halogen atoms); or, Y is selected from the group consisting of O and $NR^3$, provided that n is 2 or 3, wherein, $R^3$ is hydrogen, $C_1$-$C_6$ alkyl (optionally substituted by one to 3 halogen atoms), $C_3$-$C_6$ cycloalkyl, phenyl, benzyl, pyridyl, C(O)$R^4$, $SO_2R^4$, C(O)NH$R^4$, or C(O)NMe$R^4$, wherein, $R^4$ is hydrogen, $C_1$-$C_6$ alkyl (optionally substituted by one to 3 halogen atoms), $C_3$-$C_6$ cycloalkyl, phenyl, benzyl or pyridyl; or, Y is selected from the group consisting of S, SO and $SO_2$, provided that n is 2;

X is a methylene group (which is optionally mono- or disubstituted with methyl) or a carbonyl group;

$Ar^1$ is a divalent moiety which is either phenylene or a six-membered heteroarylene, which divalent moiety is optionally mono- or disubstituted with moieties selected from the group consisting of $C_1$-$C_6$ alkyl (optionally substituted by one to 3 halogen atoms), $C_3$-$C_{10}$ cycloalkyl and halogen; and, $Ar^2$ is an aryl or heteroaryl moiety which is optionally substituted with $C_1$-$C_6$ alkyl (which is optionally substituted with 1 to 3 halogen atoms), $C_1$-$C_6$ alkoxy (which is optionally substituted with 1 to 3 halogen atoms), $C_1$-$C_6$ alkylthio, $C_1$-$C_6$ alkoxycarbonyl, $C_1$-$C_6$ alkylaminocarbonyl, $C_1$-$C_6$ dialkylaminocarbonyl, hydroxyl, halogen, cyano or nitro.

In a further subgeneric aspect, the invention provides compounds of the formula I wherein, $R^1$ is hydrogen, $C_1$-$C_6$ alkyl, $C_3$-$C_{10}$ cycloalkyl, phenyl, benzyl or pyridyl;

$R^2$ is hydrogen;

A is a group of the formula —$(CH_2)_n$—, wherein n is 1, 2 or 3;

Y is a methylene group, provided that n is 1, 2 or 3; or,

Y is selected from the group consisting of O and NH, provided that n is 2 or 3;

Y is selected from the group consisting of S, SO and $SO_2$, provided that n is 2;

X is a methylene group;

$Ar^1$ is a divalent moiety which is either phenylene or a six-membered heteroarylene, which divalent moiety is optionally mono- or disubstituted with moieties selected from the group consisting of $C_1$-$C_6$ alkyl (optionally substituted by one to 3 halogen atoms), $C_3$-$C_{10}$ cycloalkyl and halogen; and, $Ar^2$ is a moiety selected from the group consisting of phenyl, thienyl and furanyl, which moiety is optionally substituted with $C_1$-$C_6$ alkyl (which is optionally substituted with 1 to 3 halogen atoms), $C_1$-$C_6$ alkoxy (which is optionally substituted with 1 to 3 halogen atoms), hydroxyl, halogen, cyano or nitro.

In a still further subgeneric aspect, the invention provides compounds of the formula I wherein, $R^1$ is phenyl or benzyl;

$R^2$ is hydrogen or $C_1$-$C_6$ alkyl;

A is —$(CH_2)_2$—;

Y is a methylene group, O or NH;

X is a methylene group;

$Ar^1$ is 1,4-phenylene or 1,4-pyridylene; and, $Ar^2$ is phenyl or thienyl, which are optionally mono-substituted with chloro, cyano, trifluoromethyl, methoxy or ethoxy or disubstituted with chloro.

The invention also includes tautomers, prodrugs and pharmaceutically acceptable salts the above-described compounds of the formula I.

Compounds of the formula I are agonists, antagonists or inverse agonists of the CB2 receptor and modulate the activity of this receptor. By virtue of this fact the compounds of the formula I can be used for treating inflammation, in a manner described more fully below.

Those compounds of the formula I which are agonists of the CB2 receptor can additionally be used for treating pain, in a manner described more fully below.

The invention also includes compounds of the formula

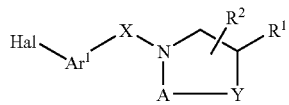

(IA)

wherein, $R^1$ is hydrogen, $C_1$-$C_6$ alkyl, $C_3$-$C_{10}$ cycloalkyl, phenyl, benzyl or pyridyl;

$R^2$ is hydrogen or $C_1$-$C_6$ alkyl;

A is a group of the formula —$(CH_2)_n$—, wherein n is 1, 2 or 3, which is optionally substituted with one or two $C_1$-$C_6$ alkyl groups;

Y is a methylene group, provided that n is 1 or 2, wherein said methylene group is optionally substituted with a halogen atom or with a $C_1$-$C_6$ alkyl group (which, in turn, is optionally substituted with one to three halogen atoms); or, Y is selected from the group consisting of O, S, SO, $SO_2$ and $NR^3$, provided that n is 2 or 3, wherein, $R^3$ is hydrogen, $C_1$-$C_6$ alkyl (optionally substituted by one to 3 halogen atoms), $C_3$-$C_6$ cycloalkyl, phenyl, benzyl, pyridyl, C(O)$R^4$, $SO_2R^4$ or C(O)NH$R^4$, C(O)NMe$R^4$, wherein, $R^4$ is hydrogen, $C_1$-$C_6$ alkyl (optionally substituted by one to 3 halogen atoms), $C_3$-$C_6$ cycloalkyl, phenyl, benzyl or pyridyl;

X is a methylene group (which is optionally mono- or disubstituted with methyl) or a carbonyl group;

$Ar^1$ is a divalent moiety which is either phenylene or a six-membered heteroarylene, which divalent moiety is optionally mono- or disubstituted with moieties selected from the group consisting of $C_1$-$C_6$ alkyl (optionally substituted by one to 3 halogen atoms), $C_3$-$C_{10}$ cycloalkyl and halogen; and, Hal is a halogen atom which is affixed to $Ar^1$.

Preferred compounds of the formula IA are those wherein:

$R^1$ is phenyl or benzyl;

$R^2$ is hydrogen or $C_1$-$C_6$ alkyl;

A is —$(CH_2)_2$—;

Y is O or NH;

X is a methylene group;

$Ar^1$ phenylene or pyridylene; and,

Hal is a bromine atom.

Compounds of the formula IA use useful as intermediates for the production of compounds of the formula I. Some compounds of the formula IA also modulate the activity of the CB2 receptor and by virtue of this fact the can be used for treating inflammation, in the manner described more fully below.

The compounds of formula I may be made using the general synthetic methods described below, which also constitute part of the invention.

General Synthetic Methods

The invention also provides processes for making compounds of Formula (I). In all schemes, unless specified otherwise, $Ar_1$, $Ar_2$, $R_1$, $R_2$, A, n, X, and Y in the formulas below shall have the meaning of $Ar_1$, $Ar_2$, $R_1$, $R_2$, A, n, X, and Y in Formula (I) of the invention described herein above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC), if desired, and intermediates and products may be purified by chromatography on silica gel and/or by recrystallization.

The examples which follow are illustrative and, as recognized by one skilled in the art, particular reagents or conditions could be modified as needed for individual compounds without undue experimentation. Starting materials and intermediates used, in the schemes below, are either commercially available or easily prepared from commercially available materials by those skilled in the art.

Compounds of Formula (I) may be synthesized by the methods illustrated in Schemes 1-5

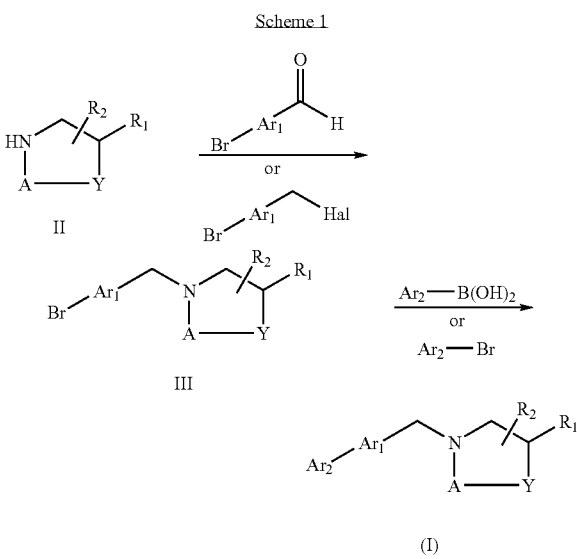

Scheme 1

As illustrated in Scheme 1, reacting a starting material of formula II with an aldehyde of formula Br—$Ar_1$—CHO or a ketone, in a suitable solvent such as THF, in the presence of a suitable reducing agent provides the alkylated amine of formula III. Alternatively, the starting amine II may also be reacted with an halide of formula Br—$Ar_1$—$CH_2$-Hal (Hal is Cl, Br or I), in a suitable solvent such as acetonitrile, in the presence of a base such as potassium carbonate to provide the alkylated amine of formula III. The appropriately substituted starting amine II may be obtained either commercially or made by procedures known to one skilled in the art.

Cross coupling the above compound of formula III with a boronic acid of formula $Ar_2$—B(OH)$_2$, in a suitable solvent, in the presence of a suitable catalyst such as tetrakis(triphenylphosphine)palladium(0) provides the compound of formula (I). Alternatively the compound of formula III may also be reacted with an aryl or heteroaryl halide of formula $Ar_2$—Br, in a suitable solvent such as DMF, in the presence of bis(pinacolato)diboron and a suitable catalyst such as tetrakis (triphenylphosphine)palladium(0) to provide the compound of formula (I).

Further modification of the initial product of formula (I), when Y=NH, by methods known in the art and illustrated in the Examples below, may be used to prepare additional compounds of this invention.

Compounds of formula (I), wherein X is a carbonyl may be prepared by the method outlined in Scheme 2

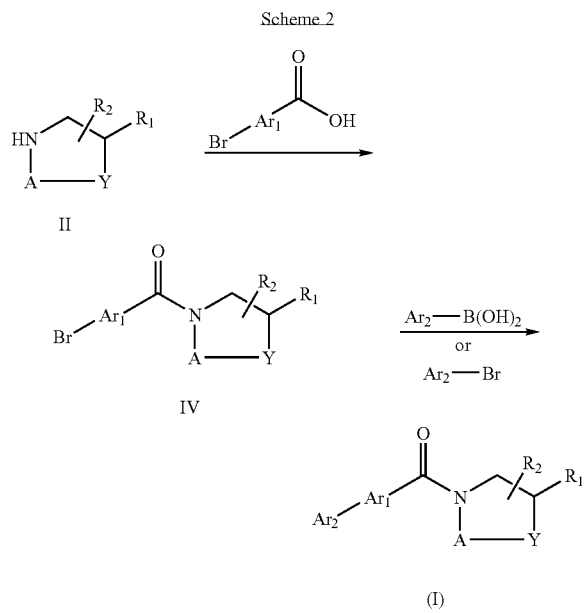

As outlined in Scheme 2, reacting a starting material of formula II with an acid of formula Br—Ar$_1$—COOH provides a coupled compound of formula IV. The appropriately substituted starting amine II may be obtained either commercially or made by procedures known to one skilled in the art. Standard peptide coupling reactions known in the art (see for example M. Bodanszky, 1984, The Practice of Peptide Synthesis, Springer-Verlag) may be employed in these syntheses. An example of suitable coupling conditions is treatment of a solution of the carboxylic acid in a suitable solvent such as DMF with EDC, HOBT, and a base such as diisopropylethylamine, followed by the desired amine. Alternatively, reaction of the carboxylic acid with reagents such as oxalyl chloride provides the corresponding acid chloride. Reaction of the acid chloride with the desired amine in a suitable solvent provides a compound of formula (IV).

Cross coupling the above compound of formula IV with a boronic acid of formula Ar$_2$—B(OH)$_2$, in a suitable solvent, in the presence of a suitable catalyst such as tetrakis(triphenylphosphine)palladium(0) provides the compound of formula (I). Alternatively the compound of formula IV may also be reacted with an aryl or heteroaryl halide of formula Ar$_2$—Br, in a suitable solvent such as DMF, in the presence of bis(pinacolato)diboron and a suitable catalyst such as tetrakis(triphenylphosphine)palladium(0) to provide the compound of formula (I).

Further modification of the initial product of formula (I), when Y=NH, by methods known in the art and illustrated in the Examples below, may be used to prepare additional compounds of this invention.

Starting materials of the formula II wherein n is 2 and Y is O, may be prepared by the method outlined in Scheme 3

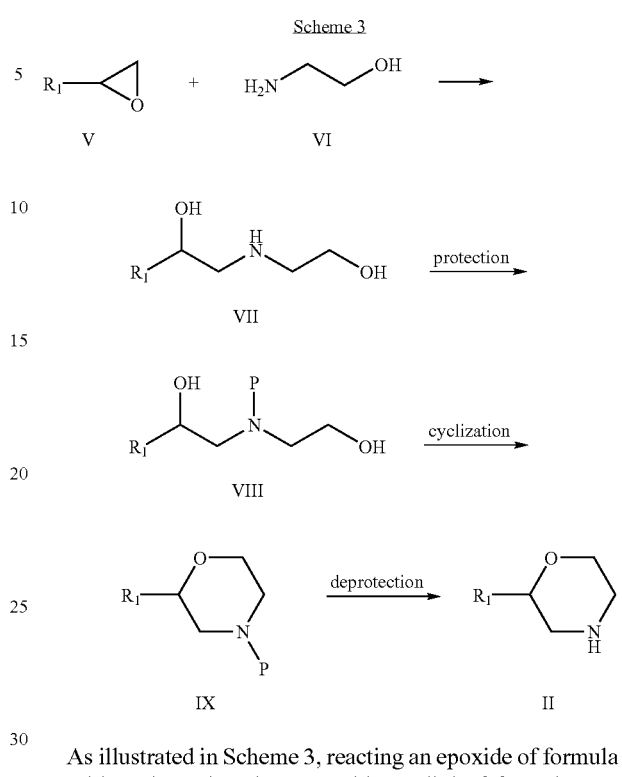

As illustrated in Scheme 3, reacting an epoxide of formula V with amino ethanol VI, provides a diol of formula VII. Reacting the compound of formula VIII with di-t-butyl dicarbonate, in a suitable solvent such as methylene chloride, in the presence of a base such as triethylamine provides a N-protected compound of the formula VIII, wherein P is a protecting group such as BOC. Cyclizing compound VIII in a suitable solvent such as toluene, in the presence of triphenyl phosphine and diethylazodicarboxylate followed by deprotection under standard conditions, provides compound of formula II.

Starting materials of the formula II wherein n is 3 and Y is O, may also be prepared by the method outlined in Scheme 3 by using propanolamine instead ethanolamine VI.

Starting materials of the formula II wherein n is 2 and Y is NH, may be prepared by the method outlined in Scheme 4

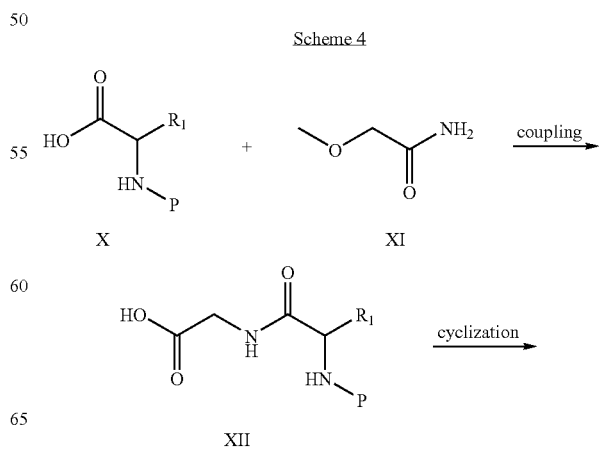

-continued

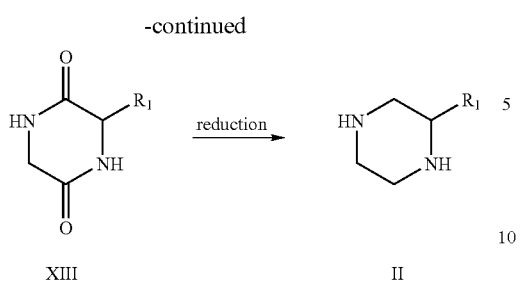

XIII    II

Coupling a N-protected amino acid X with glycine methyl ester via the formation of a mixed anhydride using isobutyl-chloroformate in a suitable solvent, in the presence of a suitable base provides the coupled product of formula XII. Cyclizing the compound of formula XII in a suitable solvent such as methylene chloride in the presence of an acid provides the cyclized compound of formula XIII. Reacting the compound of formula XIII with a reducing agent such as lithium aluminium hydride in a suitable solvent, such as THF, provides the compound of formula II.

Starting materials of the formula II wherein n is 3 and Y is NH, may also be prepared by the method outlined in Scheme 4 by using homoglycine methyl ester instead glycine methyl ester XI.

Starting materials of the formula II wherein n is 1, 2 or 3, and Y is methylene may be either available commercially or made by the method outlined in Scheme 5.

Scheme 5

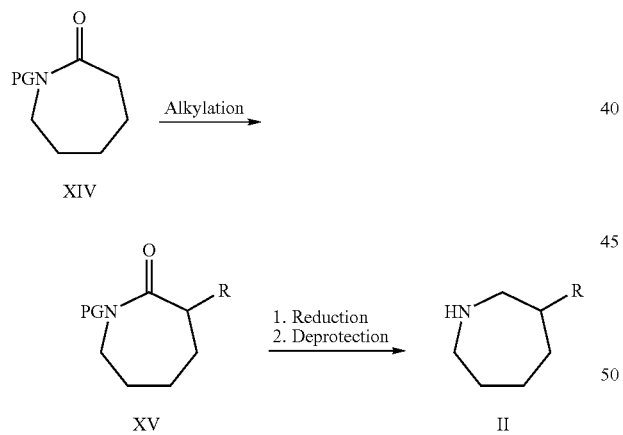

XIV

XV    II

As illustrated in Scheme 5, alkylation of the starting material XIV wherein PG is a protecting group and n is 3, in the presence of a base in a suitable solvent provides the alkylated intermediate XV. Reduction followed by deprotection of the intermediate XV, under standard conditions, provides the starting material of formula II.

SPECIFIC SYNTHETIC EXAMPLES

The manner in which the compounds of the invention can be made will be further understood by way of the following Examples.

Example 1

2-Phenyl-4-(2'-trifluoromethyl-biphenyl-4-ylmethyl)-morpholine 4-(4-Bromo-benzyl)-2-phenyl morpholine

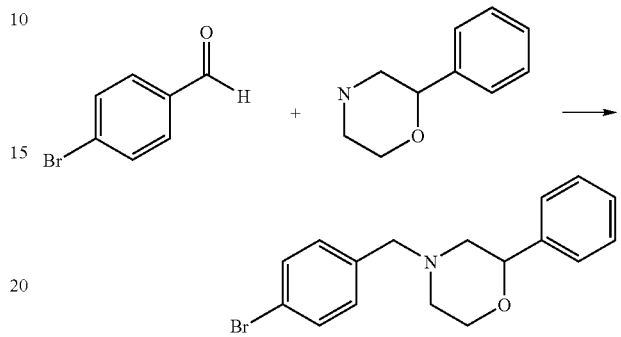

429 mg of 4-Bromobenzaldehyde was dissolved in 6 mL of THF and 386 mg of the HCl salt of 2-Phenylmorpholine (Array) and 1.15 g of MP-BH(OAc)$_3$ (2.77 mmol/g) was added. The reaction was agitated on an orbital shaker overnight at room temperature. The reaction was filtered and the resin washed several times with dichloromethane. The filtrate was concentrated and purified by flash chromatography. Yield: 281 mg.

2-Phenyl-4-(2'-trifluoromethyl-biphenyl-4-ylmethyl)-morpholine

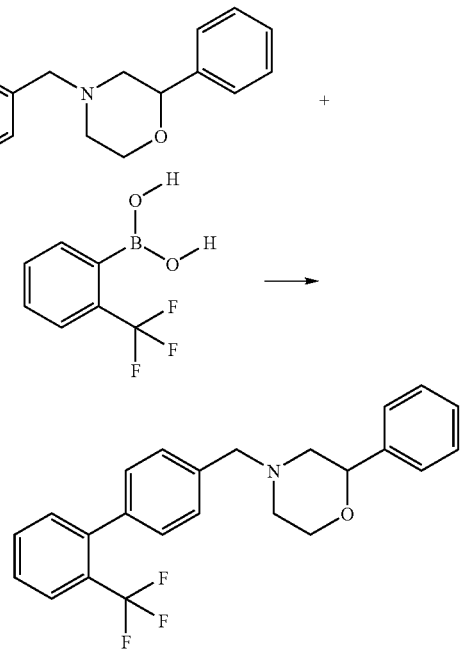

106 mg of 4-(4-Bromo-benzyl)-2-phenyl-morpholine was combined with 91 mg of 2-(Trifluoromethyl)phenyl boronic acid, 18 mg of tetrakis(triphenylphosphine)palladium(0), 1.1 mL of 2M sodium carbonate solution, 2.9 mL toluene and 1.4 mL ethanol. The reaction mixture was heated in a sealed tube at 120° C. overnight in an oil bath. The reaction mixture was filtered through Celite and concentrated in vacuo. The residue was diluted with water and extracted with ethyl acetate. The combined organic phases were washed with brine, dried over sodium sulfate, filtered and concentrated in vacuo. The crude material was purified by flash chromatography eluting in a 10 to 40% ethyl acetate/hexanes gradient. The product fractions were pooled and concentrated to afford 88.3 mg of product. ES MS (+) m/z 398

Example 2

(S)-2-Phenyl-4-(2'-trifluoromethyl-biphenyl-4-ylm-ethyl)-morpholine (S)-2-(2-Hydroxy-ethylamino)-1-phenyl-ethanol

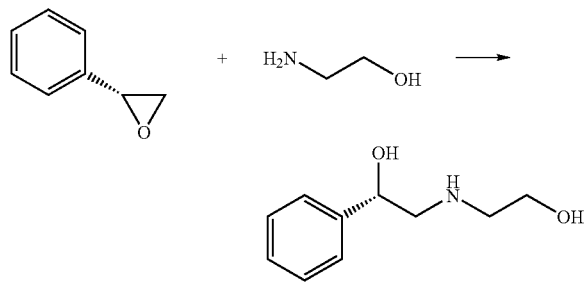

5 g of (S)-(+)-styrene oxide and 15.410 mL ethanol amine were stirred at room temperature overnight. The solution is poured into water and the water was extracted with dichloromethane. The combined dichloromethane layers were washed with brine and concentrated. The oil was used crude. Assumed quantitative yield carried on to the next step. Theoretical wt: 7.9 g (S)-(2-Hydroxy-ethyl)-(2-hydroxy-2-phenyl-ethyl)-carbamic acid tert-butyl ester

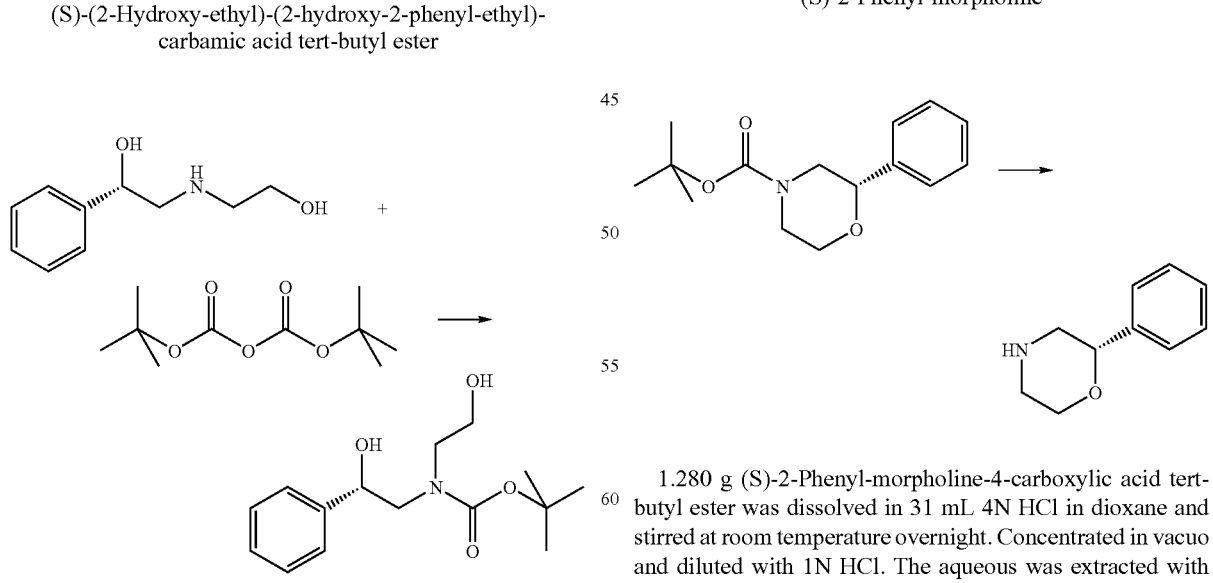

7.920 g (S)-2-(2-Hydroxy-ethylamino)-1-phenyl-ethanol and 10.5 g di-t-butyl dicarbonate in 262 mL methylene chloride were stirred together at room temperature and 9.14 mL triethylamine was added. The solution was stirred at room temperature overnight. The solution was then poured into water and extracted with methylene chloride. The combined organics were washed with brine and dried with sodium sulfate. After filtration, the crude material was purified by flash chromatography. Wt: 3.1832 g, 26% yield (S)-2-Phenyl-morpholine-4-carboxylic acid tert-butyl ester 3 g of (S)-(2-Hydroxy-ethyl)-(2-hydroxy-2-phenyl-ethyl)-carbamic acid tert-butyl ester and 0.327 g of triphenylphosphine were dissolved in 53.3 mL toluene. 0.217 g of diethylazodicarboxylate in 5.4 mL toluene was added dropwise to the resulting solution at room temperature under argon atmosphere and the mixture was stirred overnight. The solvent was removed in vacuo and the material purified by column chromatography.

(S)-2-Phenyl-morpholine 1.280 g (S)-2-Phenyl-morpholine-4-carboxylic acid tert-butyl ester was dissolved in 31 mL 4N HCl in dioxane and stirred at room temperature overnight. Concentrated in vacuo and diluted with 1N HCl. The aqueous was extracted with ether and then basicified to pH12-14 with 2N NaOH followed by extraction with DCM. The organic layers were dried over Na2SO4, filtered and concentrated in vacuo to afford 617 mg of product by H NMR. 78% yield.

(S)-4-(4-Bromo-benzyl)-2-phenyl-morpholine

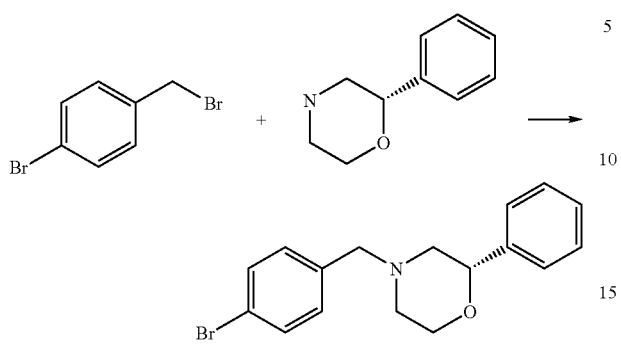

1.417 g of 4-Bromobenzyl bromide and 0.617 g of (S)-2-Phenyl-morpholine in 11 mL of acetonitrile were stirred at room temperature and 1.567 g of potassium carbonate was added. The reaction was stirred at room temperature overnight. The solution was filtered through Celite and concentrated in vacuo to afford a brown solid. Purification by flash chromatography afforded 0.851 g of product. 68% yield ES MS m/z 331.

(S)-2-Phenyl-4-(2'-trifluoromethyl-biphenyl-4-ylmethyl)-morpholine

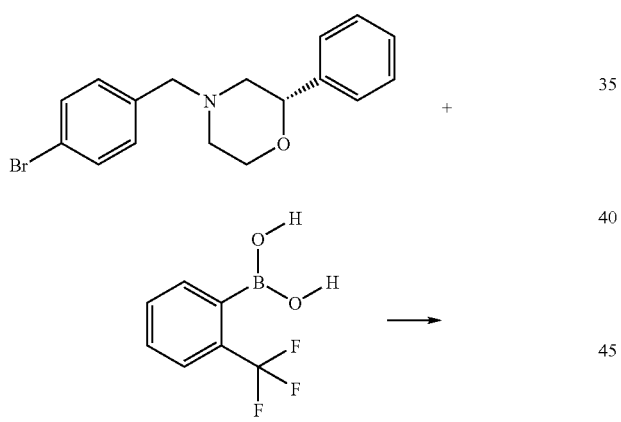

106 mg of (S)-4-(4-Bromo-benzyl)-2-phenyl-morpholine was combined with 91 mg of 2-(Trifluoromethyl)phenyl boronic acid, 18 mg of tetrakis(triphenylphosphine)palladium(0), 1.1 mL of 2M sodium carbonate solution, 2.9 mL toluene and 1.4 mL ethanol. The reaction mixture was heated in a sealed tube at 120° C. overnight in an oil bath. The reaction mixture was filtered through Celite and concentrated in vacuo. The residue was diluted with water and extracted with ethyl acetate. The combined organic phases were washed with brine, dried over sodium sulfate, filtered and concentrated in vacuo. The crude material was purified by flash chromatography eluting in a 10 to 40% ethyl acetate/hexanes gradient. The product fractions were pooled and concentrated to afford 88.3 mg of product. ES MS (+) m/z 398.

In an alternate embodiment the intermediate used in Example 2 is synthesized as follows:

2-Bromo-N-((S)-2-hydroxy-2-phenyl-ethyl)-acetamide

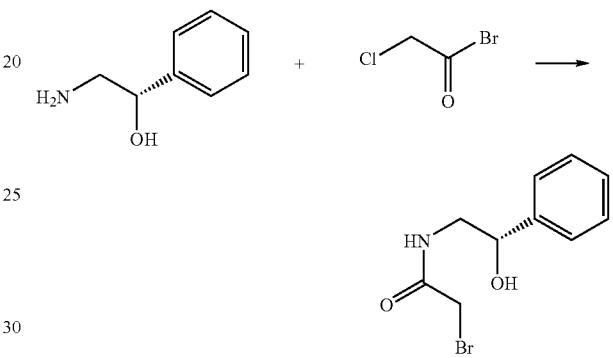

To a cold (0° C.) biphasic solution of (S)-(+)-2-amino-1-phenylethanol (6.2 g, 45.2 mmol) in EtOAc (450 mL) and saturated aqueous NaHCO$_3$ (125 mL) was added bromoacetyl bromide (4.32 mL, 49.7 mmol) via syringe. The mixture was stirred at 0° C. for 1 h then layers were separated. The aqueous layer was extracted with EtOAc (2×100 mL) then combined organics were dried with Na$_2$SO$_4$, filtered, and concentrated to dryness to afford the desired product as a residue (11.6 g, quant.) that was used in the next transformation: ES MS (+) m/z 258.

(S)-6-Phenyl-morpholin-3-one

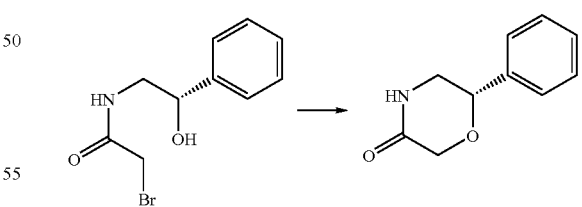

To a solution of the above bromide (11.6 g, 49.6 mmol) in dry t-BuOH (575 mL) was added potassium t-butoxide (13.9 g, 124.0 mmol). The reaction mixture was stirred for 1.5 h then treated with aqueous 6M HCl (25 mL). The solution was concentrated in vacuo. The solids were extracted with CH$_2$Cl$_2$ (600 mL), washed with aqueous saturated NaHCO$_3$ (2×200 mL), dried with Na$_2$SO$_4$, filtered, and concentrated to give the desired pure product (2.90 g, 33%) that was used in the next transformation: ES MS (+) m/z 178

(S)-2-Phenyl-morpholine

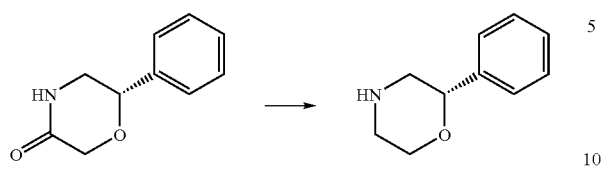

To a cold (0° C.) suspension of LAH (1.24 g, 32.7 mmol) in dry THF (40 mL) was added a solution of the morpholine amide (2.9 g, 16.46 mmol) in THF (35 mL). The cold bath was removed and the reaction mixture was stirred at 23° C. for 2 h then cooled to 0° C., diluted with Et$_2$O (100 mL), carefully treated with water until gas evolution ceased. A white precipitate had formed at this point. The solution was treated with Na$_2$SO$_4$, and all solids were filtered. The filter cake was washed with CH$_2$Cl$_2$ (100 mL) and the filtrate was concentrated in vacuo to give a pale yellow oil (2.00 g, 75%) that was used without further purification. An analytically pure sample can be obtained via purification by flash chromatography (SiO$_2$, CH$_2$Cl$_2$ to 9:1 CH$_2$Cl$_2$:MeOH) to give a 46% yield of the desired product: ES MS (+) m/z 164.

Example 3

4-(2'-Chloro-biphenyl-3-ylmethyl)-2-phenyl-morpholine

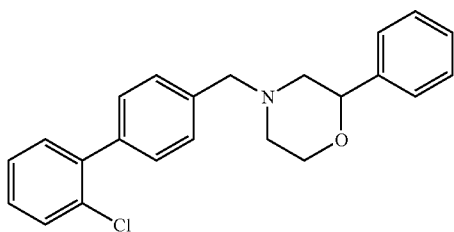

The above compound was made in the same manner as Example 1 but with the appropriate boronic acid. 84% yield ES MS m/z(+) 364

Example 4

4-(2',5'-Dichloro-biphenyl-4-ylmethyl)-2-phenyl-morpholine

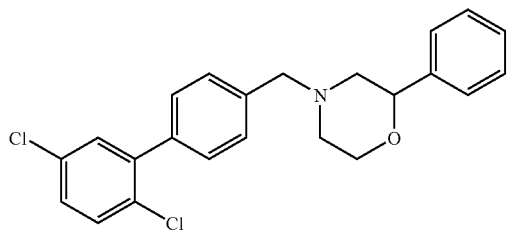

The above compound was made in the same manner as Example 1 but with the appropriate boronic acid. 70% yield ES MS m/z(+) 398

Example 5

4-(2',5'-Dimethyl-biphenyl-4-ylmethyl)-2-phenyl-morpholine

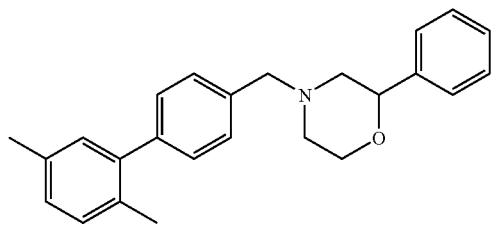

The above compound was made in the same manner as Example 1 but with the appropriate boronic acid. 75% yield ES MS m/z(+) 358

Example 6

4-(5'-Chloro-2'-methyl-biphenyl-4-ylmethyl)-2-phenyl-morpholine

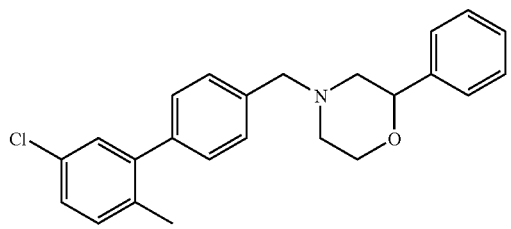

The above compound was made in the same manner as Example 1 but with the appropriate boronic acid. 86% yield ES MS m/z(+) 378

Example 7

4-(2'-Chloro-5'-methyl-biphenyl-4-ylmethyl)-2-phenyl-morpholine

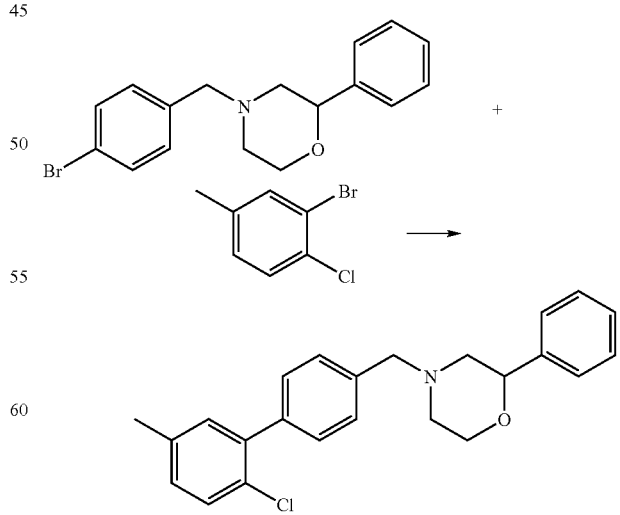

109 mg of 4-(4-Bromo-benzyl)-2-phenyl-morpholine was combined with 102 mg of bis(pinacolato)diboron, 97 mg of potassium acetate, 11 mg tetrakis(triphenylphosphine)palladium(0), and 1.9 mL DMF. The mixture was heated in a microwave reactor at 120° C. for 7 minutes and cooled. 0.8 mL of 2M aqueous sodium bicarbonate was added along with 101 mg of 3-Bromo-4-chlorotoluene in 0.15 mL DMF. The mixture was heated in the microwave reactor for an additional 5 minutes at 120° C. The reaction was cooled and filtered through Celite, washing with methylene chloride. The eluant was concentrated and purified by flash chromatography twice using an ethyl acetate/hexanes gradient to afford 3.5 mg of product. ES MS (+) m/z 378

Example 8

4-(4'-Methyl-biphenyl-4-ylmethyl)-2-phenyl-morpholine

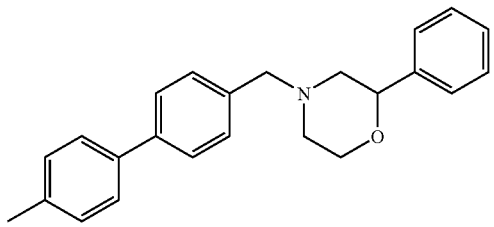

91 mg of 4-(4-Bromo-benzyl)-2-phenyl-morpholine was combined with 56 mg of 4-Methylphenyl boronic acid, 16 mg of tetrakis(triphenylphosphine)palladium(0), 0.92 mL of 2M sodium carbonate solution, 2.5 mL toluene and 1.23 mL ethanol. The reaction mixture was heated in a sealed tube at 120° C. overnight in an oil bath. The reaction mixture was filtered through Celite and concentrated in vacuo. The residue was diluted with 4 mL DCM and 130 mg of MP-TsOH resin (4.2 mmol/g loading) was added and the mixture agitated at room temperature overnight. The solution is filtered and the resin is then washed with 2M N3 in methanol to liberate product. The resin is washed several times with methylene chloride, concentrated in vacuo and purified by reverse phase HPLC. 18.5 mg of product was obtained as oil. ES MS m/z 344, 20% yield Example 9

4-(2',3'-Dichloro-biphenyl-4-ylmethyl)-2-phenyl-morpholine

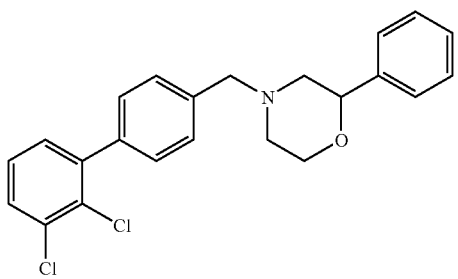

The above compound was made in the same manner as Example 8 but with the appropriate boronic acid. 10% yield, ES MS m/z 398

Example 10

4-(2',4'-Dichloro-biphenyl-4-ylmethyl)-2-phenyl-morpholine

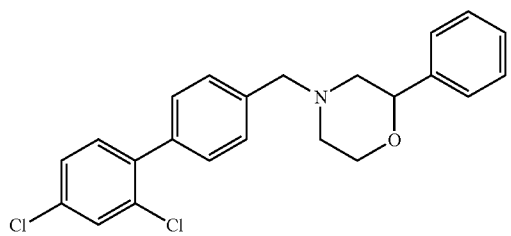

The above compound was made in the same manner as Example 8 but with the appropriate boronic acid. 3% yield, ES MS m/z 398

Example 11

4'-(2-Phenyl-morpholin-4-ylmethyl)-biphenyl-2-carbonitrile

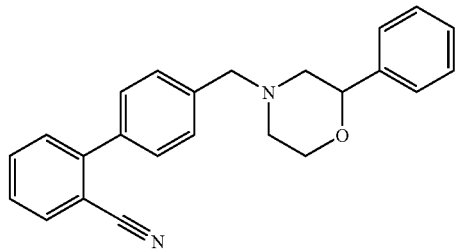

The above compound was made in the same manner as Example 8 but with the appropriate boronic acid. 5% yield, ES MS m/z 355

Example 12

4-(4-Naphthalen-2-yl-benzyl)-2-phenyl-morpholine

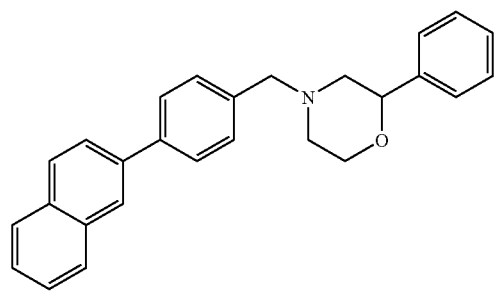

The above compound was made in the same manner as Example 8 but with the appropriate boronic acid. 4% yield, ES MS m/z 380

Example 13

2-Phenyl-4-(4-thiophen-3-yl-benzyl)-morpholine

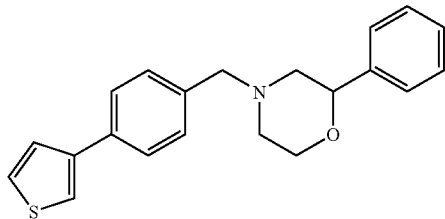

The above compound was made in the same manner as Example 8 but with the appropriate boronic acid. 16% yield, ES MS m/z 336

Example 14

4-(2'-Ethoxy-biphenyl-4-ylmethyl)-2-phenyl-morpholine

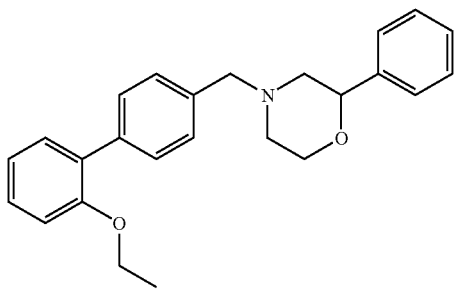

The above compound was made in the same manner as Example 8 but with the appropriate boronic acid. 12% yield, ES MS m/z 374

Example 15

2-Phenyl-4-(4-pyridin-4-yl-benzyl)-morpholine

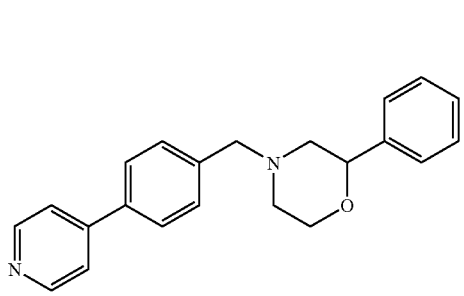

The above compound was made in the same manner as Example 8 but with the appropriate boronic acid. 21% yield, ES MS m/z 331

Example 16

4-[4-(2-Chloro-thiophen-3-yl)-benzyl]-2-phenyl-morpholine

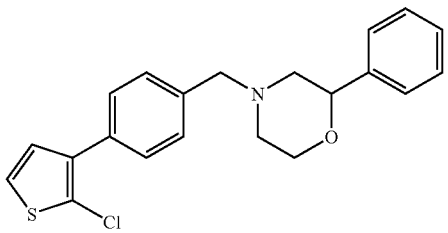

91 mg of 4-(4-Bromo-benzyl)-2-phenyl-morpholine was combined with 77 mg of bis(pinacolato)diboron, 81 mg of potassium acetate, 16 mg tetrakis(triphenylphosphine)palladium(0), and 1.9 mL DMF. The mixture was heated in a microwave reactor at 120° C. for 7 minutes and cooled. 0.7 mL of 2M aqueous sodium carbonate was added along with 81 mg of 2-Chloro-3-bromothiophene in 0.12 mL DMF. The mixture was heated in the microwave reactor for an additional 5 minutes at 120° C. The reaction was cooled and filtered through Celite, washing with methylene chloride. The residue was diluted with 4 mL DCM and 130 mg of MP-TsOH resin (4.2 mmol/g loading) was added and the mixture agitated at room temperature overnight. The solution is filtered and the resin is then washed with 2M N3 in methanol to liberate product. The resin is washed several times with methylene chloride, concentrated in vacuo and purified by reverse phase HPLC. 10.9 mg of product is obtained as oil, 10% yield. ES MS m/z 398

The above compound was made in the same manner as Example 24 but with the appropriate aryl bromide. 5% yield, ES MS m/z 370

Example 17

2-Phenyl-4-(4-pyridin-2-yl-benzyl)-morpholine

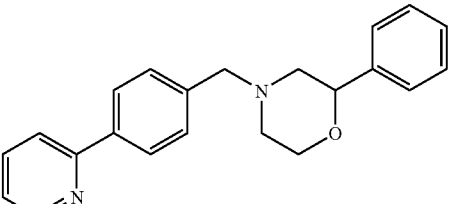

The above compound was made in the same manner as Example 16 but with the appropriate aryl bromide. 6% yield, ES MS m/z 331

Example 18

4-(2'-Trifluoromethyl-biphenyl-4-ylmethyl)-morpholine 4-(4-Bromo-benzyl)-morpholine

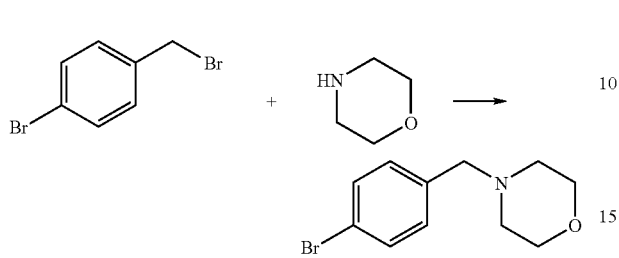

2 g of 4-Bromobenzyl bromide and 0.7 mL morpholine in 24 mL of acetonitrile were stirred at room temperature and 1.1 g of potassium carbonate was added. The reaction was stirred at room temperature overnight. The solution was filtered through Celite and concentrated in vacuo to afford a brown solid. Purification was done by flash chromatography using a methylene chloride/methanol gradient to afford 1.9 g of product as a white solid. ES MS (+) m/z 257 mp=72° C.

4-(2'-Trifluoromethyl-biphenyl-4-ylmethyl)-morpholine

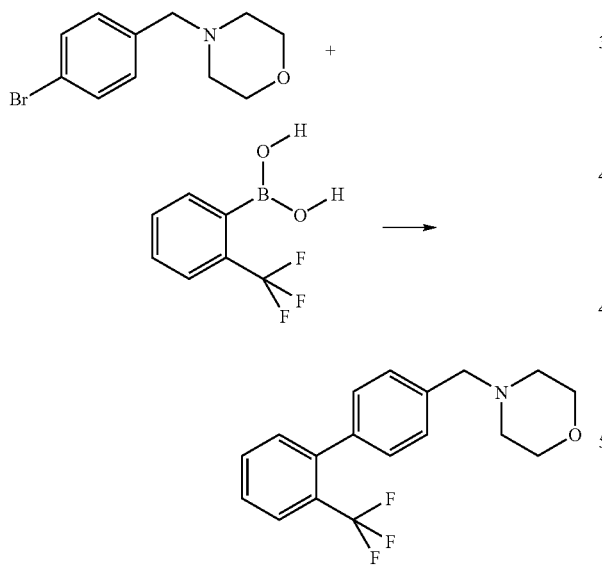

100 mg of 4-(4-Bromo-benzyl)-morpholine was combined with 111 mg of 2-(Trifluoromethyl)phenyl boronic acid, 23 mg of tetrakis(triphenylphosphine)palladium(0), 1.3 mL of 2M sodium carbonate solution, 3.6 mL toluene and 1.7 mL ethanol. The reaction mixture was heated in a sealed tube at 120° C. overnight in an oil bath. The reaction mixture was filtered through Celite and concentrated in vacuo. The residue was purified by flash chromatography using flash chromatography followed by reverse phase HPLC. 24.6 mg of product is obtained. ES MS (+) m/z 322

Example 19

4-(2'-Chloro-biphenyl-4-ylmethyl)-morpholine

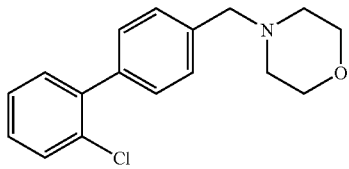

The above compound was made in the same manner as Example 18 but with the appropriate boronic acid. 36% yield, ES MS m/z 288

Example 20

4-(2',5'-Dichloro-biphenyl-4-ylmethyl)-morpholine

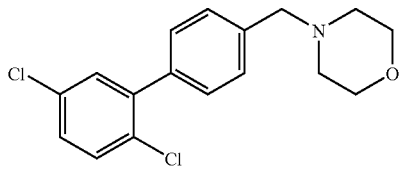

The above compound was made in the same manner as Example 18 but with the appropriate boronic acid. 42% yield, ES MS m/z 322

Example 21

4-(2',5'-Dimethyl-biphenyl-4-ylmethyl)-morpholine

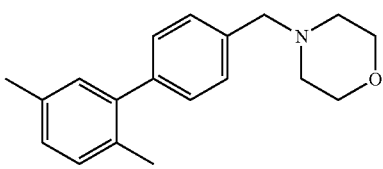

The above compound was made in the same manner as Example 18 but with the appropriate boronic acid. 38% yield, ES MS m/z 282

Example 22

4-(5'-Chloro-2'-methyl-biphenyl-4-ylmethyl)-morpholine

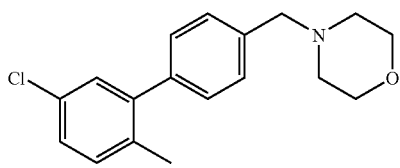

The above compound was made in the same manner as Example 18 but with the appropriate boronic acid. 49% yield, ES MS m/z 302

Example 23

4-(2'-Chloro-5'-methyl-biphenyl-4-ylmethyl)-morpholine

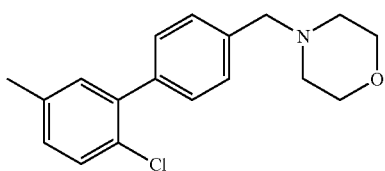

The above compound was made in the same manner as Example 7 but with 4-(4-Bromo-benzyl)-morpholine. 49% yield, ES MS m/z 302

Example 24

4-(3-Bromo-benzyl)-2-phenyl-morpholine

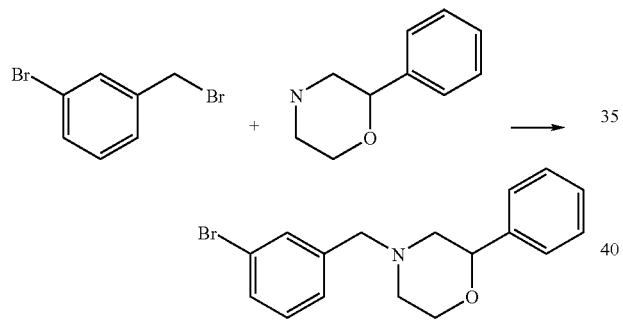

1.877 g of 3-Bromobenzyl bromide and 1 g of 2-Phenyl-morpholine in 15 mL of acetonitrile were stirred at room temperature and 2.076 g of potassium carbonate was added. The reaction was stirred at room temperature overnight. The solution was filtered through Celite and concentrated in vacuo to afford a brown solid. Purification by flash chromatography afforded 1.073 g of product. 65% yield ES MS m/z 332

Example 25

2-Phenyl-4-(2'-trifluoromethyl-biphenyl-3-ylmethyl)-morpholine

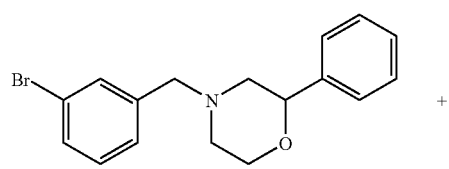

+

-continued

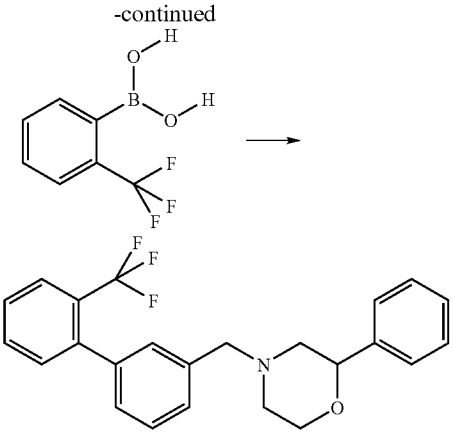

100 mg of 4-(3-Bromo-benzyl)-morpholine was combined with 86 mg of 2-(Trifluoromethyl)phenyl boronic acid, 17 mg of tetrakis(triphenylphosphine)palladium(0), 1.0 mL of 2M sodium carbonate solution, 2.7 mL toluene and 1.4 mL ethanol. The reaction mixture was heated in a sealed tube at 120° C. overnight in an oil bath. The reaction mixture was filtered through Celite and concentrated in vacuo. The residue was purified by flash chromatography using flash chromatography using an ethyl acetate/hexanes gradient. 122 mg of product was obtained. ES MS (+) m/z 398

Example 26

4-(2'-Chloro-biphenyl-3-ylmethyl)-2-phenyl-morpholine

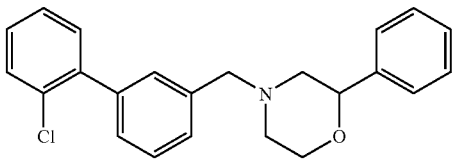

The above compound was made in the same manner as Example 24 but with the appropriate boronic acid. 77% yield, ES MS m/z 364

Example 27

4-(2',5'-Dichloro-biphenyl-3-ylmethyl)-2-phenyl-morpholine

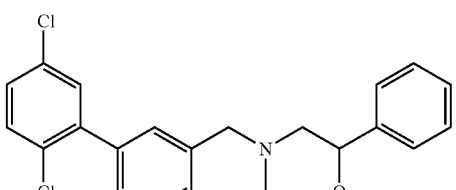

The above compound was made in the same manner as Example 24 but with the appropriate boronic acid. 87% yield, ES MS m/z 398

Example 28

4-(2',5'-Dimethyl-biphenyl-3-ylmethyl)-2-phenyl-morpholine

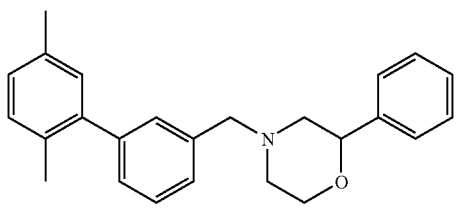

The above compound was made in the same manner as Example 24 but with the appropriate boronic acid. 82% yield, ES MS m/z 358

Example 29

4-(2-Bromo-benzyl)-2-phenyl-morpholine

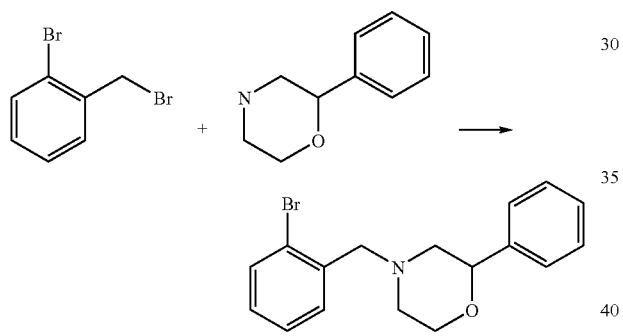

1.877 g of 2-Bromobenzyl bromide and 1 g of 2-Phenyl-morpholine in 15 mL of acetonitrile were stirred at room temperature and 2.076 g of potassium carbonate was added. The reaction was stirred at room temperature overnight. The solution was filtered through Celite and concentrated in vacuo to afford a brown solid. Purification by flash chromatography afforded 1.052 g of product. 63% yield ES MS m/z 332

Example 30

2-Phenyl-4-(2'-trifluoromethyl-biphenyl-2-ylmethyl)-morpholine

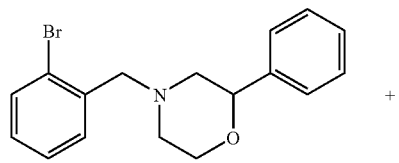

+

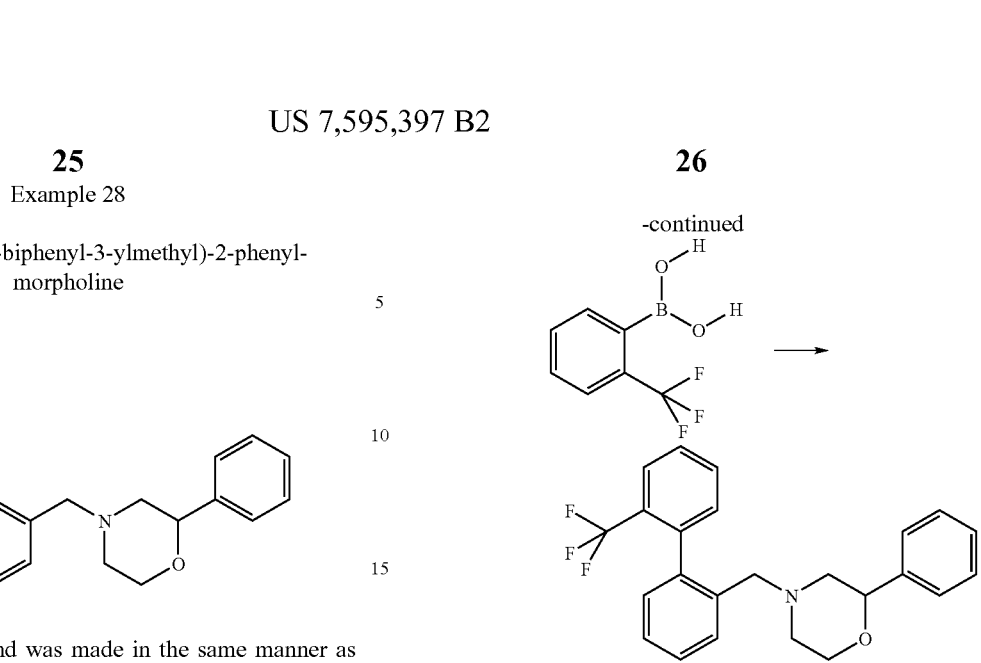

100 mg of 4-(2-Bromo-benzyl)-morpholine was combined with 86 mg of 2-(Trifluoromethyl)phenyl boronic acid, 17 mg of tetrakis(triphenylphosphine)palladium(0), 1.0 mL of 2M sodium carbonate solution, 2.71 mL toluene and 1.4 mL ethanol. The reaction mixture was heated in a sealed tube at 120° C. overnight in an oil bath. The reaction mixture was filtered through Celite and concentrated in vacuo. The residue was purified by flash chromatography using flash chromatography using an ethyl acetate/hexanes gradient. 74 mg of product is obtained. ES MS (+) m/z 398

Example 31

4-(5'-Chloro-2'-methyl-biphenyl-2-ylmethyl)-2-phenyl-morpholine

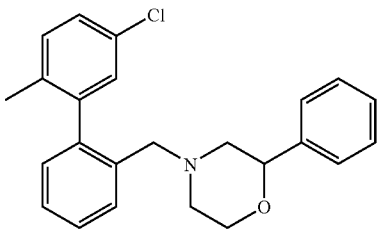

The above compound was made in the same manner as Example 7 but with 4-(2-Bromo-benzyl)-morpholine and the appropriate arylbromide. 45% yield, ES MS m/z 378

Example 32

4-(2'-Chloro-5'-methyl-biphenyl-2-ylmethyl)-2-phenyl-morpholine

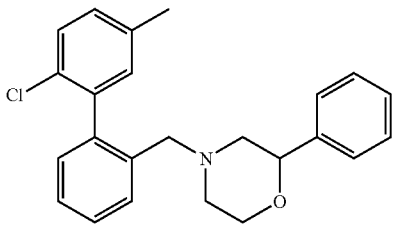

The above compound was made in the same manner as Example 7 but with 4-(2-Bromo-benzyl)-morpholine as the appropriate arylbromide. 39% yield, ES MS m/z 378

Example 33

3-Phenyl-1-(2'-trifluoromethyl-biphenyl-4-ylmethyl)-piperazine (2-tert-Butoxycarbonylamino-2-phenyl-acetylamino)-acetic acid methyl ester

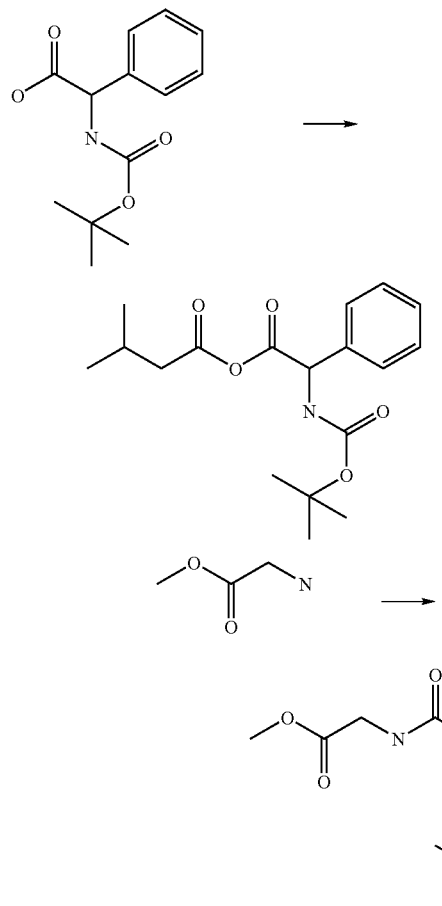

5 g of N-tert-butoxycarbonyl phenylglycine were dissolved in THF under nitrogen atmosphere and cooled to 0° C. 1.1 equiv. of triethylamine were added, followed by 1.1 equiv. of isobutylchloroformate to form the mixed anhydride solution. The reaction was stirred at room temperature for 1 h. 1.1 equiv. of the HCl salt of glycine methyl ester were dissolved in anhydrous dichloromethane, 1 eqiv. of triethylamine were added. This solution was then added dropwise to the cooled, mixed anhydride solution. The reaction was stirred for 3 h at 0° C. The reaction was filtered and the filtrate concentrated in vacuo. The residue was taken up into ethyl acetate, washed with 5% aqueous citric acid solution, 5% aqueous sodium bicarbonate solution, water and brine. The organic phase was dried over sodium sulfate, filtered and concentrated in vacuo to afford in a quantitative yield (2-tert-butoxycarbonylamino-2-phenyl-acetylamino)-acetic acid methyl ester as colorless oil. ES MS(+) m/z 323

3-Phenyl-piperazine-2,5-dione

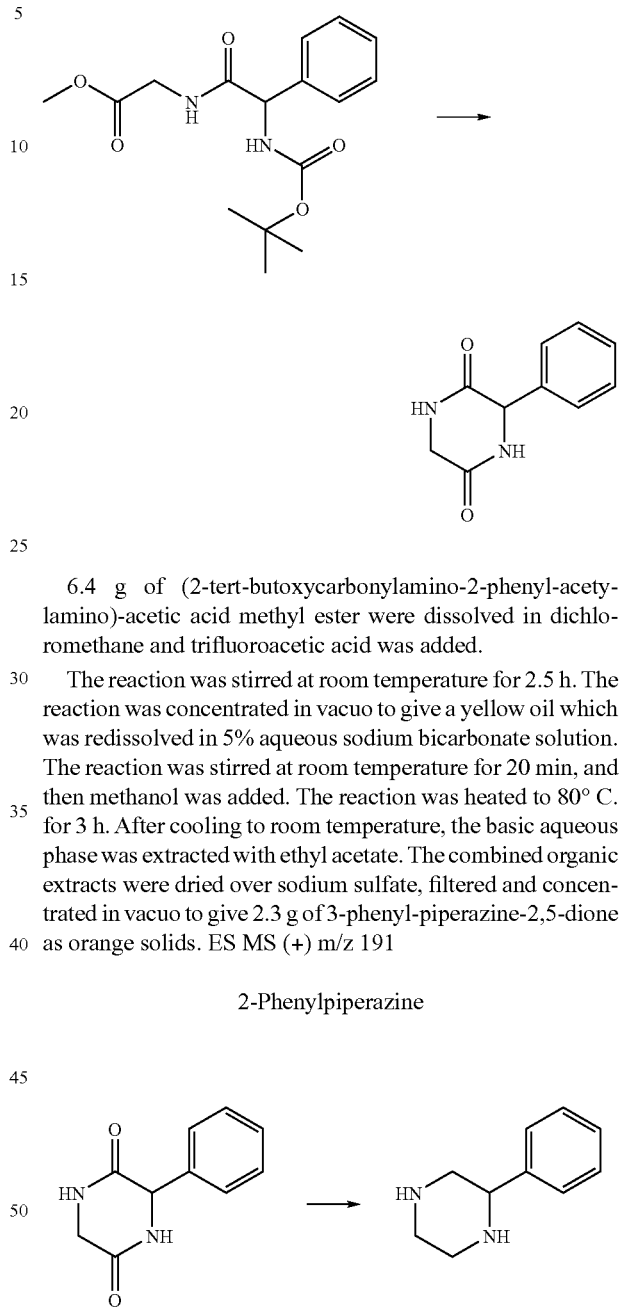

6.4 g of (2-tert-butoxycarbonylamino-2-phenyl-acetylamino)-acetic acid methyl ester were dissolved in dichloromethane and trifluoroacetic acid was added.

The reaction was stirred at room temperature for 2.5 h. The reaction was concentrated in vacuo to give a yellow oil which was redissolved in 5% aqueous sodium bicarbonate solution. The reaction was stirred at room temperature for 20 min, and then methanol was added. The reaction was heated to 80° C. for 3 h. After cooling to room temperature, the basic aqueous phase was extracted with ethyl acetate. The combined organic extracts were dried over sodium sulfate, filtered and concentrated in vacuo to give 2.3 g of 3-phenyl-piperazine-2,5-dione as orange solids. ES MS (+) m/z 191

2-Phenylpiperazine 2.3 g of 3-phenyl-piperazine-2,5-dione were suspended in anhydrous THF under nitrogen and cooled in an ice-bath. 4 equiv. of lithium aluminium hydride were added. The reaction was stirred at 0° C. for 0.5 h, and then heated to reflux overnight. The reaction was quenched by the subsequent addition of 1 mL/gLiAlH$_4$ of water, 1 mL/gLiAlH$_4$ of 5% aqueous Sodium hydroxide solution and 3 mL/gLiAlH$_4$ of water. The resulting solid were separated by filtration through Celite and rinsed with ethyl acetate. The filtrate was concentrated in vacuo to afford 2 g of 2-phenylpiperazine as brown oil. ES MS (+) m/z 163

1-(4-Bromo-benzyl)-3-phenyl-piperazine

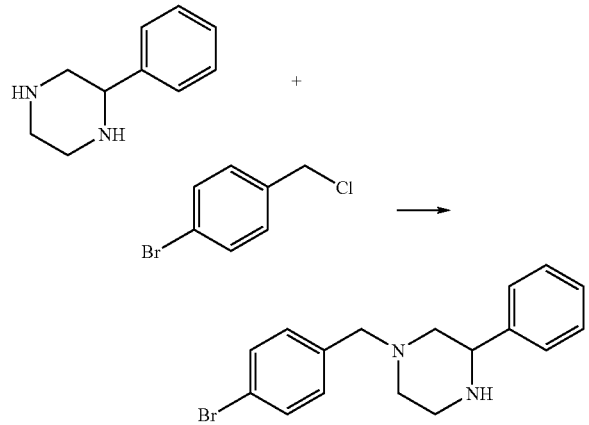

2 g of 2-phenylpiperazine were dissolved in acetonitrile and cooled to 0° C. A solution of 0.5 quiv. 4-bromobenzyl-chloride in acetonitrile was added dropwise over 1 h. The reaction was stirred at room temperature overnight. The reaction mixture was concentrated and the residue was purified by column chromatography (silica, eluent dichloromethane, 0-5% methanol) to afford 1 g of 1-(4-bromo-benzyl)-3-phenyl-piperazine. ES MS (+) m/z 301.

or:

1-(4-Bromo-benzyl)-3-phenyl-piperazine

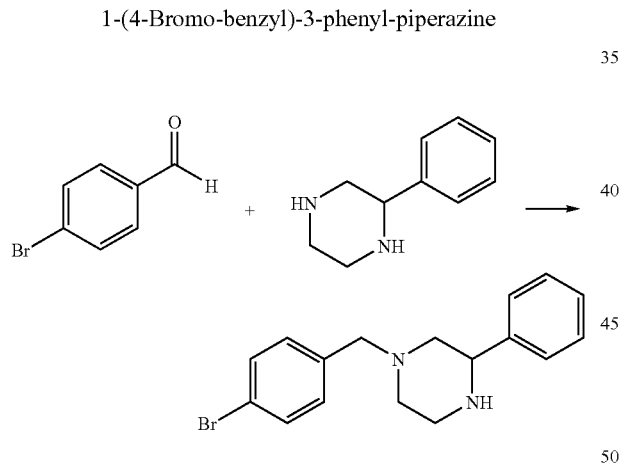

1.03 g of 4-Bromobenzaldehyde was dissolved in 15 mL of THF and 1 g of 2-Phenylpiperazine and 2.67 g of MP-BH(OAc)3 (2.77 mmol/g) was added. The reaction was agitated on an orbital shaker overnight at room temperature. The reaction was concentrated in vacuo and purified by flash chromatography. 530 mg of product is isolated. ES MS (+) m/z 331.

or:

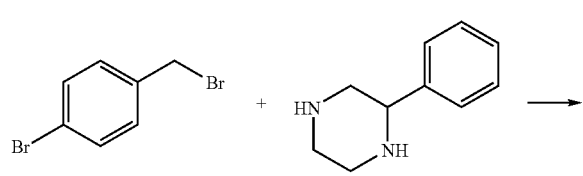

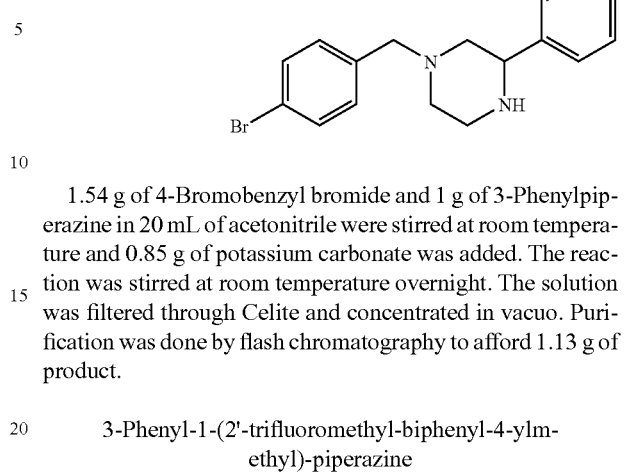

1.54 g of 4-Bromobenzyl bromide and 1 g of 3-Phenylpiperazine in 20 mL of acetonitrile were stirred at room temperature and 0.85 g of potassium carbonate was added. The reaction was stirred at room temperature overnight. The solution was filtered through Celite and concentrated in vacuo. Purification was done by flash chromatography to afford 1.13 g of product.

3-Phenyl-1-(2'-trifluoromethyl-biphenyl-4-ylmethyl)-piperazine

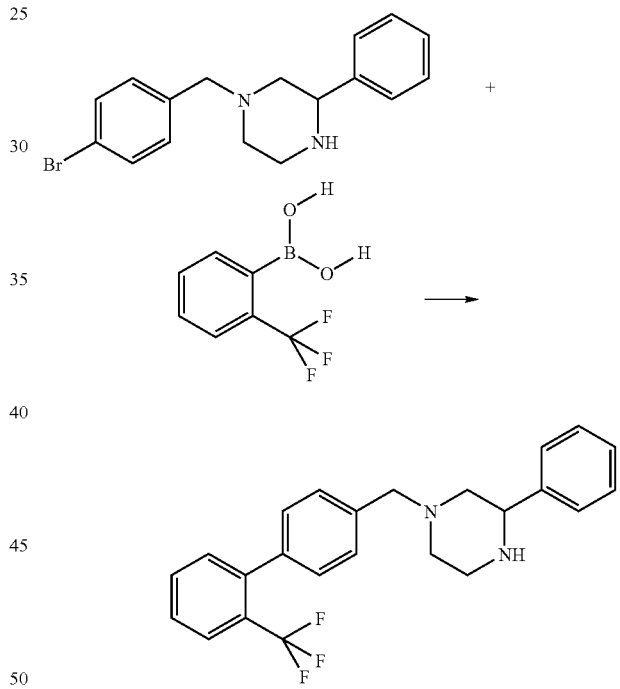

100 mg of 1-(4-Bromo-benzyl)-3-phenyl-piperazine was combined with 136 mg of 2-(Trifluoromethyl)phenyl boronic acid, 17 mg of tetrakis(triphenylphosphine)palladium(0), 1.01 mL of 2M sodium carbonate solution, 2.7 mL toluene and 1.4 mL ethanol. The reaction mixture was heated in a sealed tube at 120° C. overnight in an oil bath. The reaction mixture was filtered through Celite and concentrated in vacuo. The residue was diluted with water and extracted with ethyl acetate. The combined organic phases were washed with brine, dried over sodium sulfate, filtered and concentrated in vacuo. The crude material was purified by flash chromatography eluting in a 0-20% methylene chloride/methanol gradient. The product fractions were pooled and concentrated to afford 49.5 mg of product. ES MS (+) m/z 397

Example 34

1-(2'-Chloro-biphenyl-4-ylmethyl)-3-phenyl-piperazine

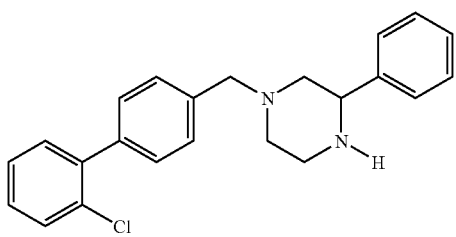

The above compound was made in the same manner as Example 33 but with the appropriate boronic acid. 28% yield, ES MS m/z 363

Example 35

1-(2',5'-Dimethyl-biphenyl-4-ylmethyl)-3-phenyl-piperazine

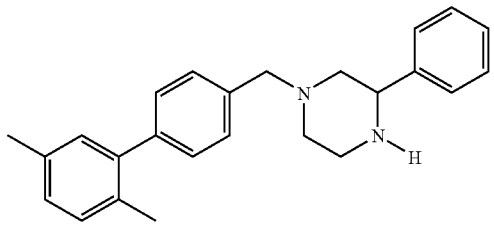

The above compound was made in the same manner as Example 33 but with the appropriate boronic acid. 21% yield, ES MS m/z 357

Example 36

1-(5'-Chloro-2'-methyl-biphenyl-4-ylmethyl)-3-phenyl-piperazine

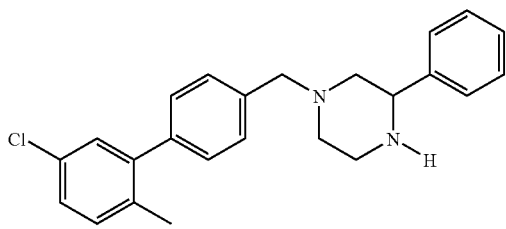

The above compound was made in the same manner as Example 33 but with the appropriate boronic acid. 24% yield, ES MS m/z 377

Example 37

1-(2'-Chloro-5'-methyl-biphenyl-4-ylmethyl)-3-phenyl-piperazine

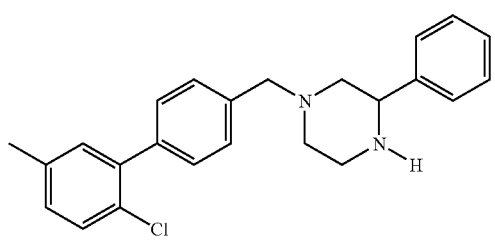

The above compound was made in the same manner as Example 7 but with 1-(4-Bromo-benzyl)-3-phenyl-piperazine. 26% yield, ES MS m/z 377

Example 38

6-Dimethyl-4-(2'-trifluoromethyl-biphenyl-4-ylmethyl)-morpholine 4-(4-Bromo-benzyl)-2,6-dimethyl-morpholine

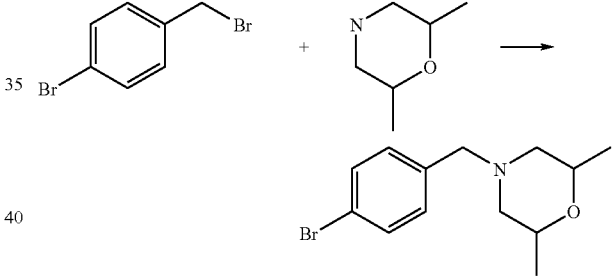

2 g of 4-Bromobenzyl bromide and 0.99 mL 3,5-Dimethylmorpholine in 24 mL of acetonitrile were stirred at room temperature and 1.106 g of potassium carbonate was added. The reaction was stirred at room temperature overnight. The solution was filtered through Celite and concentrated in vacuo to afford a brown solid. Purification was done by flash chromatography using a methylene chloride/methanol gradient to afford 365 mg of product as one regioisomer, the trans methyl, and 1.54 g of the cis methyl regioisomer. ES MS (+) m/z 284.

2,6-Dimethyl-4-(2'-trifluoromethyl-biphenyl-4-ylmethyl)-morpholine

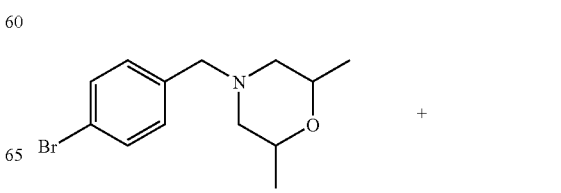

-continued

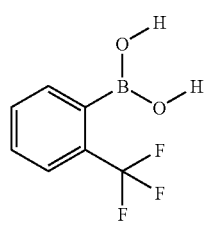
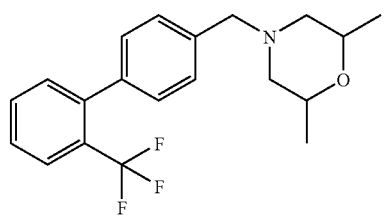

100 mg of 4-(4-Bromo-benzyl)-2,6-dimethyl-morpholine was combined with 100 mg of 2-(Trifluoromethyl)phenyl boronic acid, 20 mg of tetrakis(triphenylphosphine)palladium(0), 1.179 mL of 2M sodium carbonate solution, 3.2 mL toluene and 1.6 mL ethanol. The reaction mixture was heated in a sealed tube at 120° C. overnight in an oil bath. The reaction mixture was filtered through Celite and concentrated in vacuo. The residue was purified by reverse phase HPLC. ES MS (+) m/z 350.

Example 39

4-(2'-Chloro-biphenyl-4-ylmethyl)-trans-2,6-dimethyl-morpholine

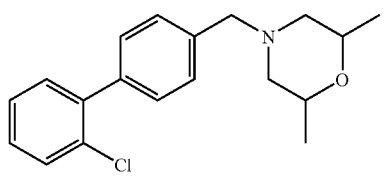

The above compound was made in the same manner as Example 38 but with the appropriate boronic acid. 32% yield, ES MS m/z 316

Example 40

4-(2',5'-Dichloro-biphenyl-4-ylmethyl)-2,6-dimethyl-morpholine

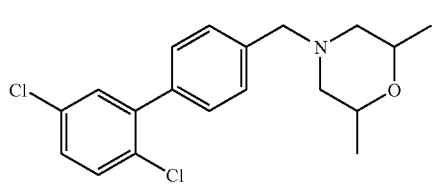

The above compound was made in the same manner as Example 38 but with the appropriate boronic acid. 35% yield, ES MS m/z 350

Example 41

4-(2',5'-Dimethyl-biphenyl-4-ylmethyl)-2,6-dimethyl-morpholine

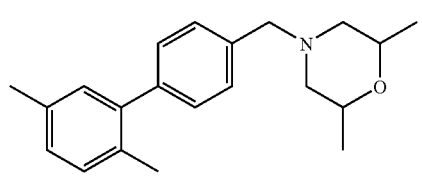

The above compound was made in the same manner as Example 50 but with the appropriate boronic acid. 38% yield, ES MS m/z 310

Example 42

4-(5'-Chloro-2'-methyl-biphenyl-4-ylmethyl)-trans-2,6-dimethyl-morpholine

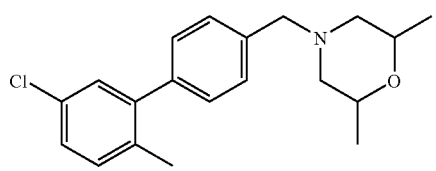

The above compound was made in the same manner as Example 7 but with the appropriate arylbromide and 4-(4-Bromo-benzyl)-2,6-dimethyl-morpholine. 9% yield, ES MS m/z 330

Example 43

2-Pyridin-3-yl-4-(2'-chloro-biphenyl-4-ylmethyl)-morpholine 4-(4-Bromo-benzyl)-2-pyridin-3-yl-morpholine

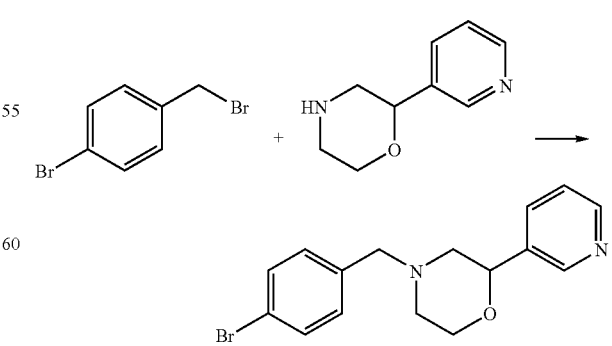

5.632 g of 4-Bromobenzyl bromide and 3.819 g of 2-Pyridin-3-yl morpholine oxalate (Array) in 50 mL of acetonitrile were stirred at room temperature and 6.229 g of potassium carbonate was added. The reaction was stirred at room temperature overnight. The solution was filtered through Celite and concentrated in vacuo to afford a brown solid. Purification is done by flash chromatography to afford product. Wt: 211 mg; 16% yield. ES MS m/z 334

2-Pyridin-3-yl-4-(2'-chloro-biphenyl-4-ylmethyl)-morpholine

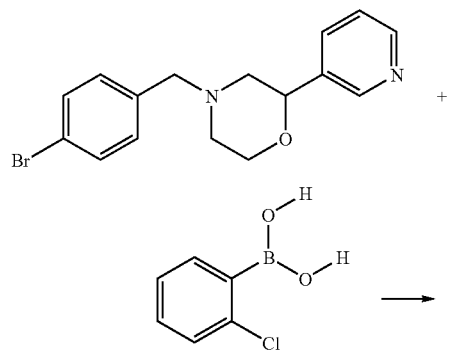

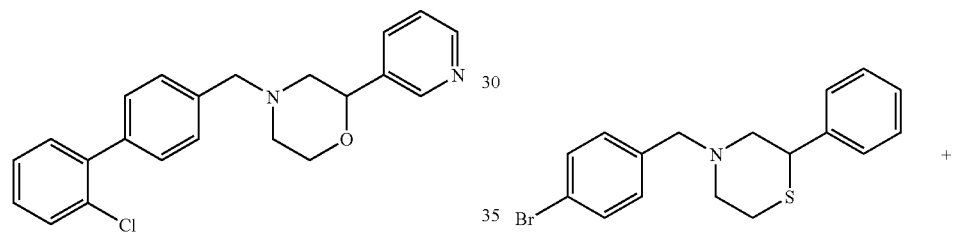

105 mg of 4-(4-Bromo-benzyl)-2-pyridin-3-yl-morpholine was combined with 74 mg of 2-Chlorophenyl boronic acid, 36 mg of tetrakis(triphenylphosphine)palladium(0), 1.055 mL of 2M sodium carbonate solution, 2.8 mL toluene and 1.4 mL ethanol. The reaction mixture was heated in a sealed tube at 120° C. overnight in an oil bath. The reaction mixture was filtered through Celite and concentrated in vacuo. The residue was purified by reverse phase HPLC. ES MS (+) m/z 365, 97% yield.

Example 44

2-Phenyl-4-(2'-trifluoromethyl-biphenyl-4-ylmethyl)-thiomorpholine 4-(4-Bromo-benzyl)-2-phenyl-thiomorpholine

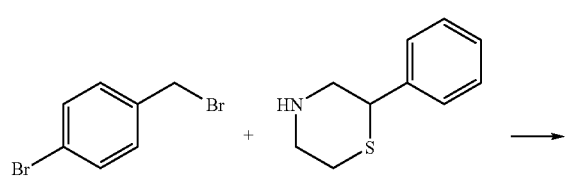

-continued

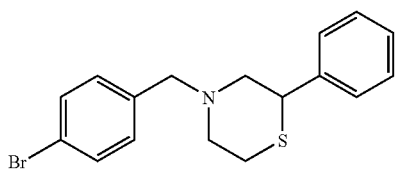

5.632 g of 4-Bromobenzyl bromide and 2.694 g of 2-Phenylthiomorpholine (Array) in 50 mL of acetonitrile were stirred at room temperature and 6.229 g of potassium carbonate was added. The reaction was stirred at room temperature overnight. The solution was filtered through Celite and concentrated in vacuo to afford a brown solid. Purification was done by flash chromatography to afford product. Wt: 0.859 g, 53% yield. ES MS m/z 348/350

2-Phenyl-4-(2'-trifluoromethyl-biphenyl-4-ylmethyl)-thiomorpholine

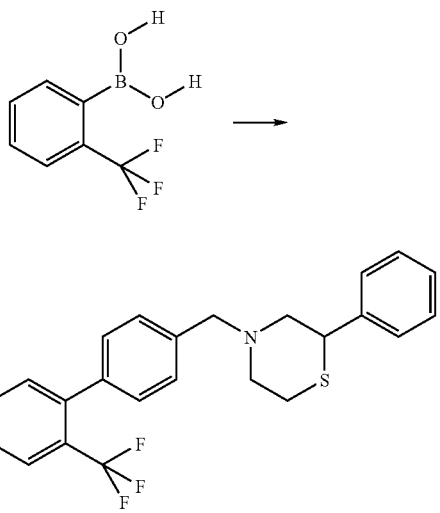

100 mg of 105 mg of 4-Bromobenzyl bromide was combined with 82 mg of 2-(Trifluoromethyl)phenyl boronic acid, 33 mg of tetrakis(triphenylphosphine)palladium(0), 0.96 mL of 2M sodium carbonate solution, 2.6 mL toluene and 1.3 mL ethanol. The reaction mixture was heated in a sealed tube at 120° C. overnight in an oil bath. The reaction mixture was filtered through Celite and concentrated in vacuo. The residue was purified by reverse phase HPLC. ES MS (+) m/z 414, 75% yield.

Example 45

4-(2'-Chloro-biphenyl-4-ylmethyl)-2-phenyl-thiomorpholine

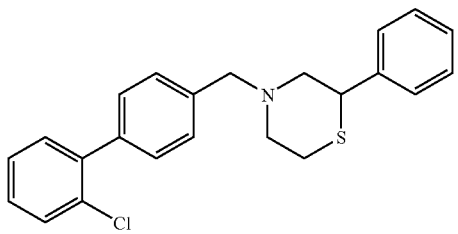

The above compound was made in a similar manner to Example 44 but with the appropriate boronic acid. 78% yield, ES MS m/z 380.

Example 46

4-(2',5'-Dichloro-biphenyl-4-ylmethyl)-2-phenyl-thiomorpholine

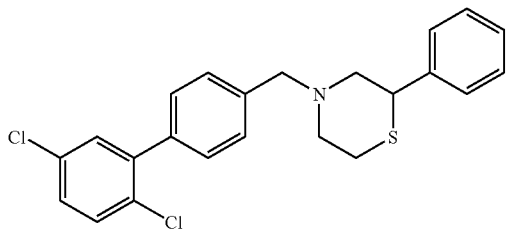

The above compound was made in a similar manner to Example 44 but with the appropriate boronic acid. 16% yield, ES MS m/z 414.

Example 47

3-Phenyl-1-(2'-trifluoromethyl-biphenyl-4-ylmethyl)-pyrrolidine 1-(4-Bromo-benzyl)-3-phenyl-pyrrolidine

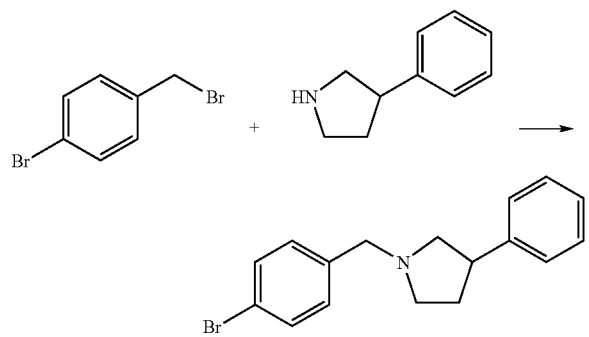

5.632 g of 4-Bromobenzyl bromide and 2.211 of 3-Phenylpyrrolidine (Array) in 50 mL of acetonitrile were stirred at room temperature and 6.229 g of potassium carbonate was added. The reaction was stirred at room temperature overnight. The solution was filtered through Celite and concentrated in vacuo to afford a brown solid. Purification was done by flash chromatography to afford product. Wt: 33 mg, 2% yield, ES MS m/z 316/318

3-Phenyl-1-(2'-chloromethyl-biphenyl-4-ylmethyl)-pyrrolidine

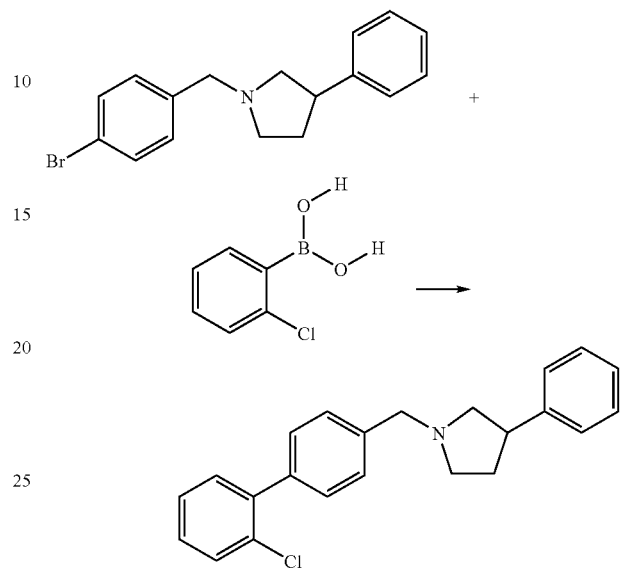

33 of 41-(4-Bromo-benzyl)-3-phenyl-pyrrolidine was combined with 24 mg of 2-Chlorophenyl boronic acid, 12 mg of tetrakis(triphenylphosphine)palladium(0), 0.348 mL of 2M sodium carbonate solution, 0.936 mL toluene and 0.468 mL ethanol. The reaction mixture was heated in a sealed tube at 120° C. overnight in an oil bath. The reaction mixture was filtered through Celite and concentrated in vacuo. The residue was purified by reverse phase HPLC. ES MS (+) m/z 348, 36% yield.

Example 48

3-Phenyl-1-(2'-trifluoromethyl-biphenyl-4-ylmethyl)-piperidine 1-(4-Bromo-benzyl)-3-phenyl-piperidine

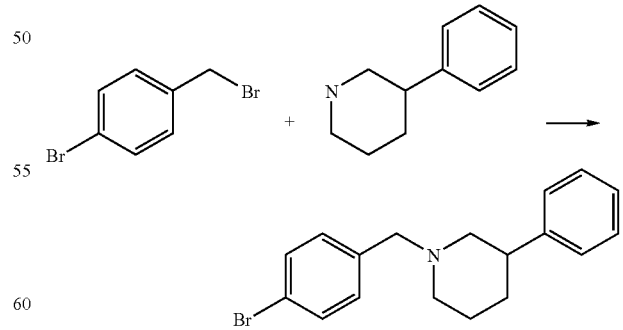

5.632 g of 4-Bromobenzyl bromide and 2.422 g of 2-Phenylpiperidine (Array) in 50 mL of acetonitrile were stirred at room temperature and 6.229 g of potassium carbonate was added. The reaction was stirred at room temperature overnight. The solution was filtered through Celite and concentrated in vacuo to afford a brown solid. Purification was done by flash chromatography to afford product. Wt:0.908 g, 54% yield.

3-Phenyl-1-(2'-trifluoromethyl-biphenyl-4-ylm-ethyl)-piperidine

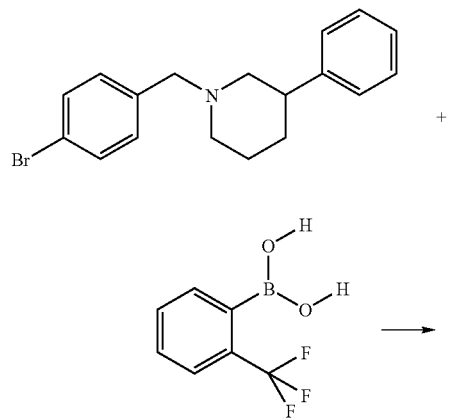

100 mg of 1-(4-Bromo-benzyl)-3-phenyl-piperidine was combined with 862 mg of 2-(Trifluoromethyl)phenyl boronic acid, 35 mg of tetrakis(triphenylphosphine)palladium(0), 1.015 mL of 2M sodium carbonate solution, 2.7 mL toluene and 1.4 mL ethanol. The reaction mixture was heated in a sealed tube at 120° C. overnight in an oil bath. The reaction mixture was filtered through Celite and concentrated in vacuo. The residue was purified by reverse phase HPLC. ES MS (+) m/z 396, 100% yield Example 49

1-(5'-Chloro-2'-methyl-biphenyl-4-ylmethyl)-3-phenyl-piperidine

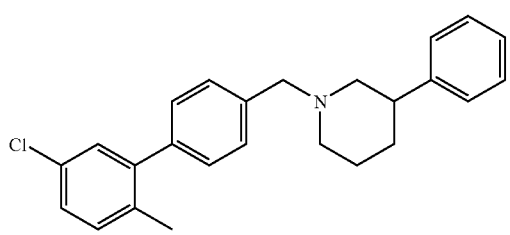

The above compound was made in the same manner as Example 7 but with the appropriate arylbromide and 1-(4-Bromo-benzyl)-3-phenyl-piperidine. 27% yield, ES MS m/z 376

Example 50

1-(2'-Chloro-biphenyl-4-ylmethyl)-3-phenyl-piperidine

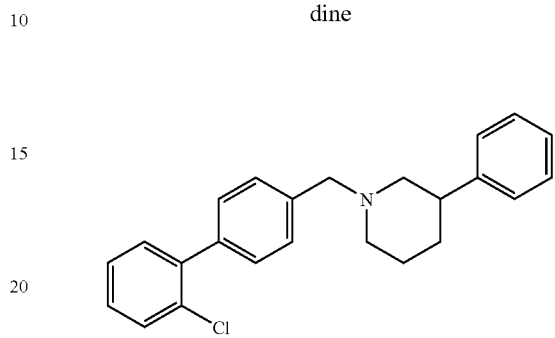

The above compound was made in a similar manner as Example 48 but with the appropriate boronic acid. 36% yield ES MS m/z 362.

Example 51

1-(2',5'-Dichloro-biphenyl-4-ylmethyl)-3-phenyl-piperidine

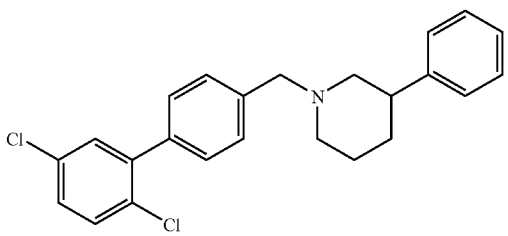

The above compound was made in a similar manner as Example 48 but with the appropriate boronic acid. 28% yield ES MS m/z 396.

Example 52

(2-Phenyl-morpholin-4-yl)-(2'-trifluoromethyl-biphenyl-4-yl)-methanone (4-Bromo-phenyl)-(2-phenyl-morpholin-4-yl)-methanone

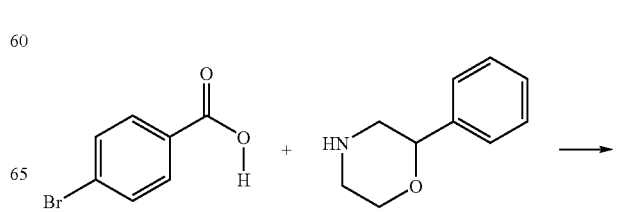

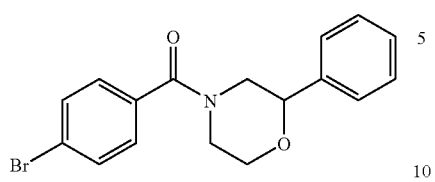

5 g of p-Bromobenzoic acid, 4.966 g 3-Phenylmorpholine HCl, 5.245 g EDC, 3.696 g HOBt and 4.766 mL Hunig's Base in 25 mL DMF was stirred at room temperature overnight. The reaction was diluted with water and extracted with ethyl acetate. The organic layers were combined, washed with 1N HCl, aqueous saturated sodium bicarbonate solution and brine. The organics were concentrated in vacuo and purified by flash chromatography to afford product. Wt: 1.335 g, 77% yield. ES MS m/z 346/348

(2-Phenyl-morpholin-4-yl)-(2'-trifluoromethyl-biphenyl-4-yl)-methanone

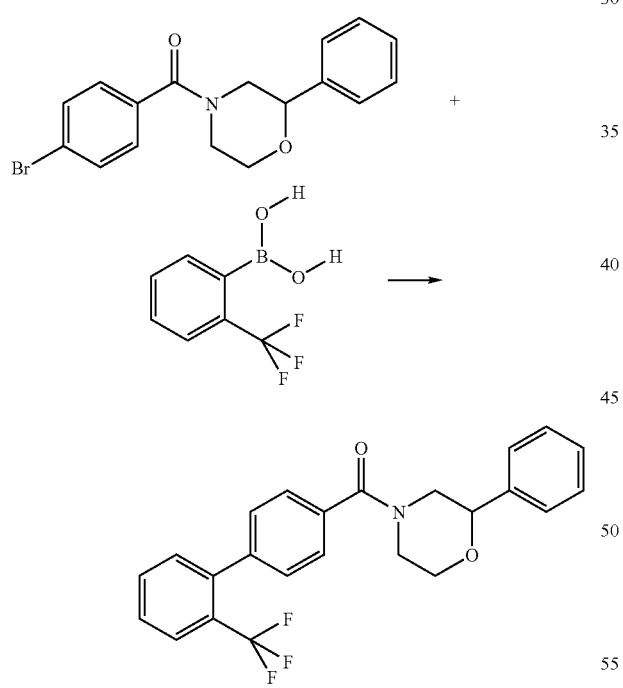

100 mg of (4-Bromo-phenyl)-(2-phenyl-morpholin-4-yl)-methanone was combined with 82 mg of 2-(Trifluoromethyl) phenyl boronic acid, 33 mg of tetrakis(triphenylphosphine) palladium(0), 0.968 mL of 2M sodium carbonate solution, 2.6 mL toluene and 1.3 mL ethanol. The reaction mixture was heated in a sealed tube at 120° C. overnight in an oil bath. The reaction mixture was filtered through Celite and concentrated in vacuo. The residue was purified by reverse phase HPLC. ES MS (+) m/z 412, 97% yield.

Example 53

(2'-Chloro-biphenyl-4-yl)-(2-phenyl-morpholin-4-yl)-methanone

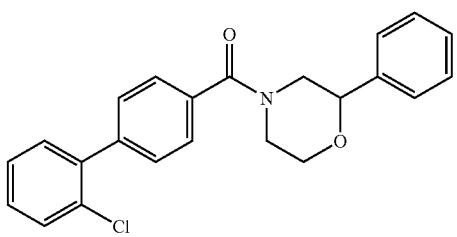

The above example was made in a similar manner to Example 60 but with the appropriate boronic acid. 59% yield, ES MS m/z 378.

Example 54

(2',5'-Dimethyl-biphenyl-4-yl)-(2-phenyl-morpholin-4-yl)-methanone

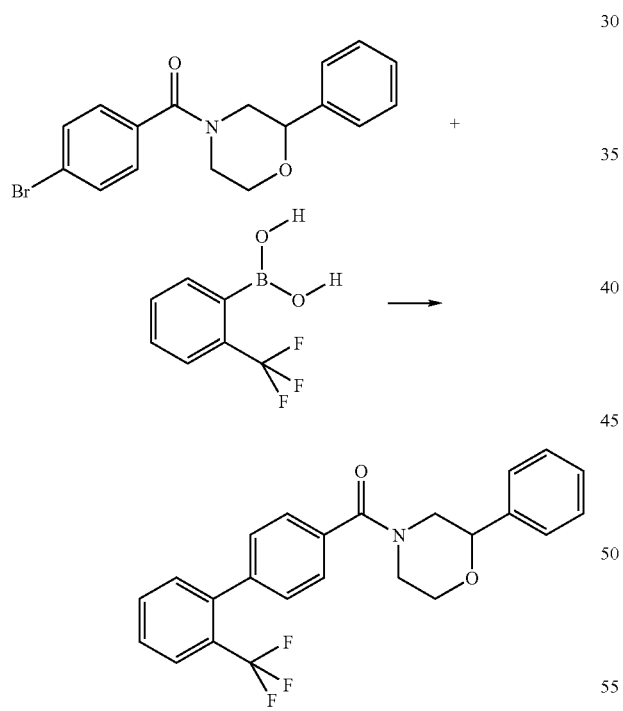

The above example was made in a similar manner to Example 60 but with the appropriate boronic acid. 68% yield, ES MS m/z 372.

Example 55

(2',3'-Dichloro-biphenyl-4-yl)-(2-phenyl-morpholin-4-yl)-methanone

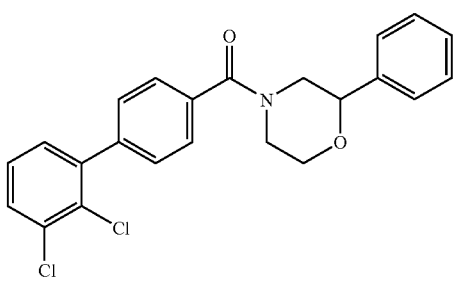

The above example was made in a similar manner to Example 60 but with the appropriate boronic acid. 19% yield, ES MS m/z 412.

Example 56

(3-Phenyl-piperidin-1-yl)-(2'-trifluoromethyl-biphenyl-4-yl)-methanone (4-Bromo-phenyl)-(3-phenyl-piperidin-1-yl)-methanone

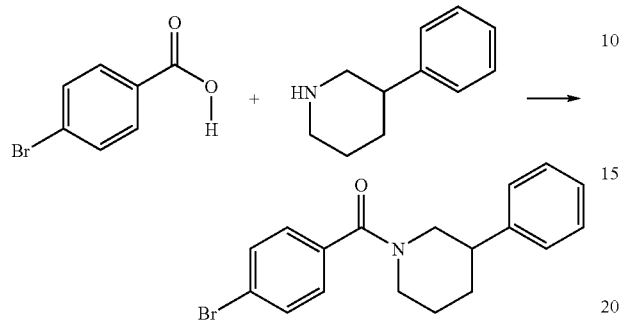

The above compound could be made in the following manner, analogous to Example 60. 1 eq. of p-Bromobenzoic acid could be combined with 1 eq. 3-Phenylpiperidine HCl, 1.1 equivalents EDC, 1.1 equivalents HOBt and 2.2 equivalents Hunig's Base in DMF (concentration of 1 mL of DMF/mmol acid) would be stirred at room temperature overnight. The solution would then be diluted with water and extracted with ethyl acetate. The organic layers would then be combined and washed with water, aqueous saturated sodium bicarbonate solution, 1N HCl and brine. The organic layers would be dried with sodium sulfate, filtered and concentrated. Purification would be done with flash chromatography to afford product.

(3-Phenyl-piperidin-1-yl)-(2'-trifluoromethyl-biphenyl-4-yl)-methanone

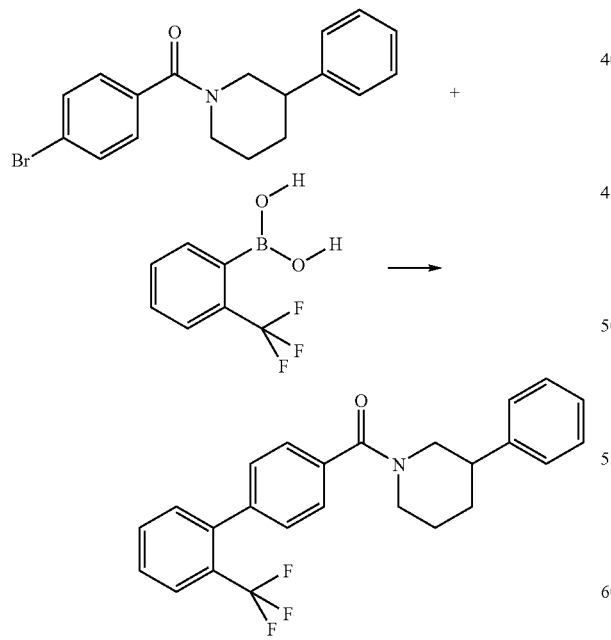

This compound could be made in the following manner analogous to Example 60; 1 equivalent of (4-Bromo-phenyl)-(3-phenyl-piperidin-1-yl)-methanone would be combined with 1.5 equivalents of 2-(Trifluoromethyl)phenyl boronic acid, 10 mol % of tetrakis(triphenylphosphine)palladium(0), 6.7 equivalents of 2M sodium carbonate solution, toluene and ethanol. The reaction mixture would be heated in a sealed tube at 120° C. overnight in an oil bath. The reaction mixture would then be filtered through Celite and concentrated in vacuo. The residue would be diluted with water and extracted with ethyl acetate. The combined organic phases would be washed with brine, dried over sodium sulfate, filtered and concentrated in vacuo. The crude material would be purified by flash chromatography to afford product.

Example 57

(3-Phenyl-pyrrolidin-1-yl)-(2'-trifluoromethyl-biphenyl-4-yl)-methanone (4-Bromo-phenyl)-(3-phenyl-pyrrolidin-1-yl)-methanone

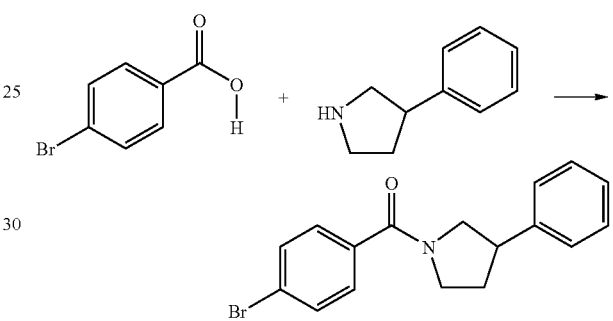

The above compound could be made in the following manner analogous to Example 60: 1 equivalent of p-Bromobenzoic acid, 1 equivalent 3-Phenylpyrrolidine, 1.1 equivalents of EDC, 1.1 equivalents of HOBt and 1 equivalent of Hunig's Base in DMF would be stirred at room temperature overnight. The solution would then be diluted with water and extracted with ethyl acetate. The organic layers would be combined and washed with water, aqueous saturated sodium bicarbonate solution, 1N HCl and brine. The organic layers would be dried with sodium sulfate, filtered and concentrated. Purification would be done with flash chromatography to afford product.

(3-Phenyl-pyrrolidin-1-yl)-(2'-trifluoromethyl-biphenyl-4-yl)-methanone

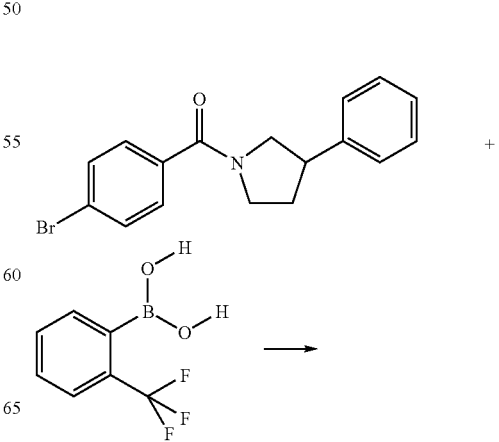

-continued

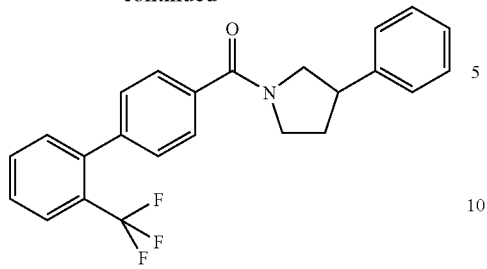

The above compound could be made in the following manner: 1 eq. of (4-Bromo-phenyl)-(3-phenyl-pyrrolidin-1-yl)-methanone would be combined with 1.5 eq. of 2-(Trifluoromethyl)phenyl boronic acid, 10 mol % of tetrakis (triphenylphosphine)palladium(0), 6.7 eq. of 2M sodium carbonate solution, toluene and ethanol. The reaction mixture would be heated in a sealed tube at 120° C. overnight in an oil bath. The reaction mixture would be filtered through Celite and concentrated in vacuo. The residue would be diluted with water and extracted with ethyl acetate. The combined organic phases would be washed with brine, dried over sodium sulfate, filtered and concentrated in vacuo. The crude material would be purified by flash chromatography to afford product.

Example 58

2-Benzyl-4-(2'-trifluoromethyl-biphenyl-4-ylmethyl)-morpholine 1-(2-Hydroxy-ethylamino)-3-phenyl-propan-2-ol

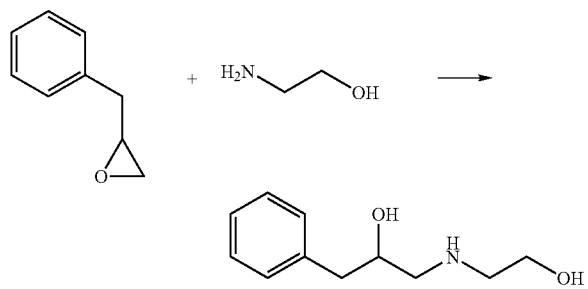

The above compound could be made in the same manner as Example 1 using the appropriate epoxide. 1 equivalent of (2,3-Epoxypropyl)benzene oxide and 4 eq. ethanol amine could be stirred at room temperature overnight. The solution could be poured into water and the water is extracted with dichloromethane. The combined dichloromethane layers could be washed with brine and concentrated.

(2-Hydroxy-ethyl)-(2-hydroxy-3-phenyl-propyl)-carbamic acid tert-butyl ester

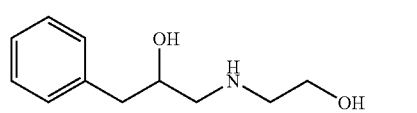

-continued

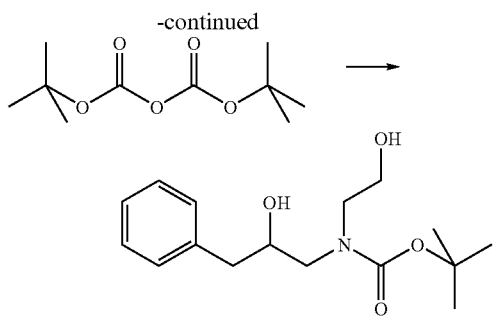

The above compound could be made in the following manner: 1 eq. 1-(2-Hydroxy-ethylamino)-3-phenyl-propan-2-ol and 1.1 eq. di-t-butyl dicarbonate in methylene chloride could be stirred together at room temperature and 1.5 eq. triethylamine could be added. The solution could be stirred at room temperature overnight. The solution could be poured into water and extracted with methylene chloride. The combined organics could be washed with brine and dried with sodium sulfate. After filtration, the crude material could be purified by flash chromatography.

2-Benzyl-morpholine-4-carboxylic acid tert-butyl ester

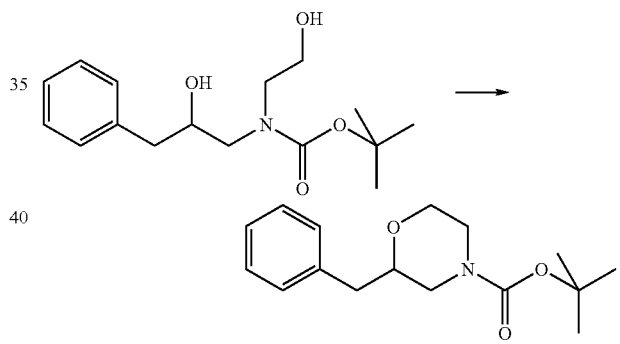

The above compound could be made in the following manner: 1 eq. of (2-Hydroxy-ethyl)-(2-hydroxy-3-phenyl-propyl)-carbamic acid tert-butyl ester and 1.2 eq. of triphenylphosphine could be dissolved in toluene. 1.2 eq. of diethylazodicarboxylate in toluene could be added dropwise to the resulting solution at room temperature under argon atmosphere and the mixture could be stirred overnight. The solvent could be removed in vacuo and the material purified by column chromatography.

2-Benzyl-morpholine

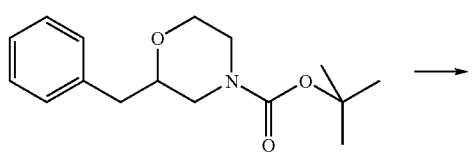

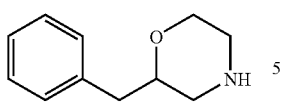

The above compound could be made in the following manner: 1 eq. 2-Benzyl-morpholine-4-carboxylic acid tert-butyl ester could be dissolved in 4N solution of hydrogen chloride in dioxane and the mixture could be stirred at 60° C. for 3 h. The solvent could be removed in vacuo and 1N aqueous hydrogen chloride solution could be added to the resulting residue, and the mixture could be washed with diethyl ether. The aqueous layer could be adjusted to pH 14 by addition of 2N NaOH solution and extracted with methylene chloride. The organic layer could be washed with brine and dried over sodium sulfate. After filtering, the material could be purified by column chromatography.

2-Benzyl-4-(4-bromo-benzyl)-morpholine

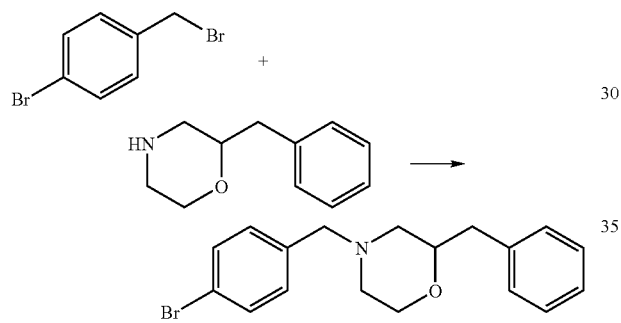

The above compound could be made in the following manner: 1.5 eq. of 4-Bromobenzyl bromide and 1 eq. of 2-Benzyl-morpholine in acetonitrile could be stirred at room temperature and 3 eq. of potassium carbonate could be added. The reaction could be stirred at room temperature overnight. The solution could be filtered through Celite and concentrated in vacuo to afford a brown solid. Purification could be done by flash chromatography to afford product.

2-Benzyl-4-(2'-trifluoromethyl-biphenyl-4-ylm-ethyl)-morpholine

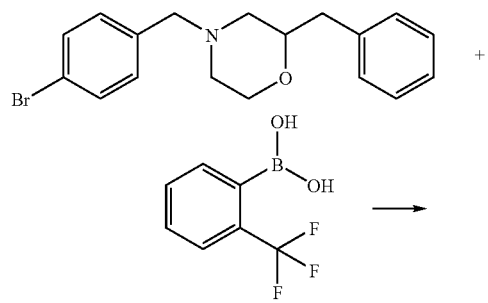

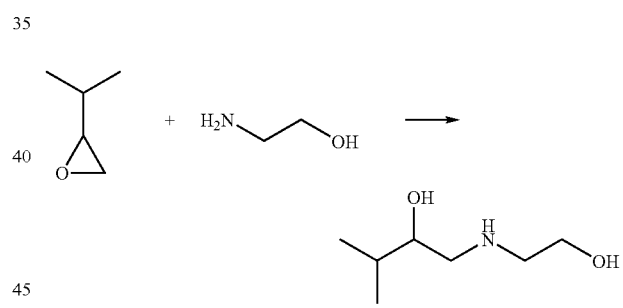

The above compound could be made in the following manner: 1 eq. of 2-Benzyl-4-(4-bromo-benzyl)-morpholine could be combined with 1.5 eq. of 2-(Trifluoromethyl)phenyl boronic acid, 10 mol % of tetrakis(triphenylphosphine)palladium(0), 6.7 eq. of 2M sodium carbonate solution, toluene and ethanol. The reaction mixture could be heated in a sealed tube at 120° C. overnight in an oil bath. The reaction mixture could be filtered through Celite and concentrated in vacuo. The residue could be diluted with water and extracted with ethyl acetate. The combined organic phases could be washed with brine, dried over sodium sulfate, filtered and concentrated in vacuo. The crude material could be purified by flash chromatography to afford product.

Example 59

2-Isopropyl-4-(2'-trifluoromethyl-biphenyl-4-ylm-ethyl)-morpholine 1-(2-Hydroxy-ethylamino)-3-methyl-butan-2-ol

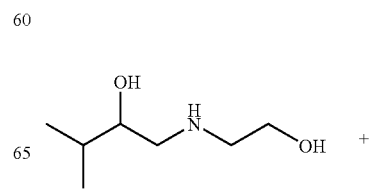

The above compound could be made in the same manner as Example 1 using the appropriate epoxide: 1 eq. of (2,3-Epoxypropyl)benzene oxide and 4 eq. ethanol amine The above compound could be made in the following manner: stirred at room temperature overnight. The solution could be poured into water and the water is extracted with dichloromethane. The combined dichloromethane layers could be washed with brine and concentrated.

(2-Hydroxy-ethyl)-(2-hydroxy-3-methyl-butyl)-carbamic acid tert-butyl ester

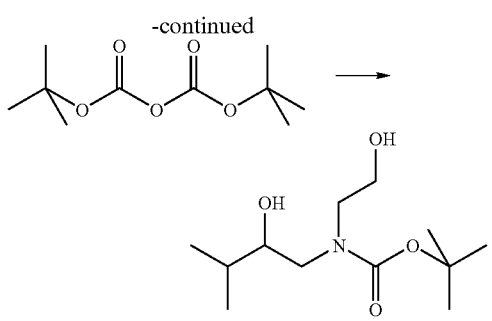

The above compound could be made in the following manner: 1 eq. 1-(2-Hydroxy-ethylamino)-3-methyl-butan-2-ol and 1.1 eq. di-t-butyl dicarbonate in methylene chloride could be stirred together at room temperature and 1.5 eq. triethylamine could be added. The solution could be stirred at room temperature overnight. The solution could be then poured into water and extracted with methylene chloride. The combined organics could be washed with brine and dried with sodium sulfate. After filtration, the crude material could be purified by flash chromatography.

2-Isopropyl-morpholine-4-carboxylic acid tert-butyl ester

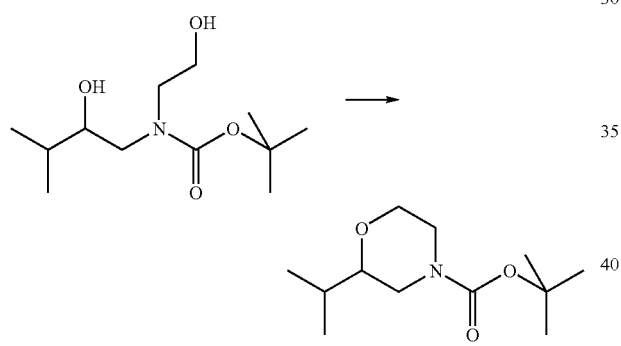

The above compound could be made in the following manner: 1 eq. of (2-Hydroxy-ethyl)-(2-hydroxy-3-methyl-butyl)-carbamic acid tert-butyl ester and 1.2 eq. of triphenylphosphine could be dissolved in toluene. 1.2 eq. of diethylazodicarboxylate in toluene could be added dropwise to the resulting solution at room temperature under argon atmosphere and the mixture could be stirred overnight. The solvent could be removed in vacuo and the material purified by column chromatography.

2-Isopropyl-morpholine

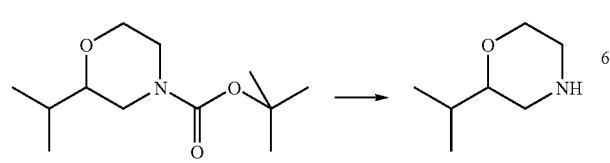

The above compound could be made in the following manner: 2-Isopropyl-morpholine-4-carboxylic acid tert-butyl ester in 4N solution of hydrogen chloride in dioxane could be stirred at 60° C. for 3 h. The solvent could be removed in vacuo and 1N aqueous hydrogen chloride solution could be added to the resulting residue, and the mixture could be washed with diethyl ether. The aqueous layer could be adjusted to pH 14 by addition of 2N NaOH solution and extracted with methylene chloride. The organic layer could be washed with brine and dried over sodium sulfate. After filtering, the material could be purified by column chromatography.

4-(4-Bromo-benzyl)-2-isopropyl-morpholine

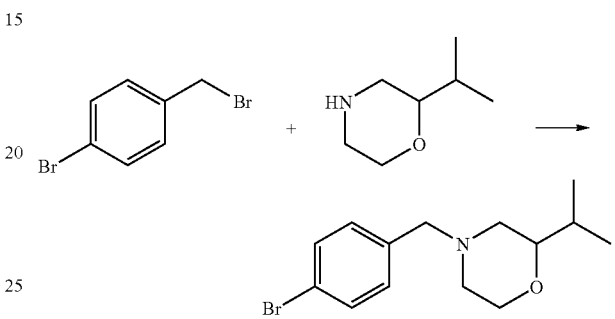

The above compound could be made in the following manner: 1.5 eq. of 4-Bromobenzyl bromide and 1 eq. of 2-Isopropyl-morpholine in acetonitrile could be stirred at room temperature and 3 eq. of potassium carbonate could be added. The reaction could be stirred at room temperature overnight. The solution could be filtered through Celite and concentrated in vacuo to afford a brown solid. Purification could be done by flash chromatography to afford product.

2-Isopropyl-4-(2'-trifluoromethyl-biphenyl-4-ylmethyl)-morpholine

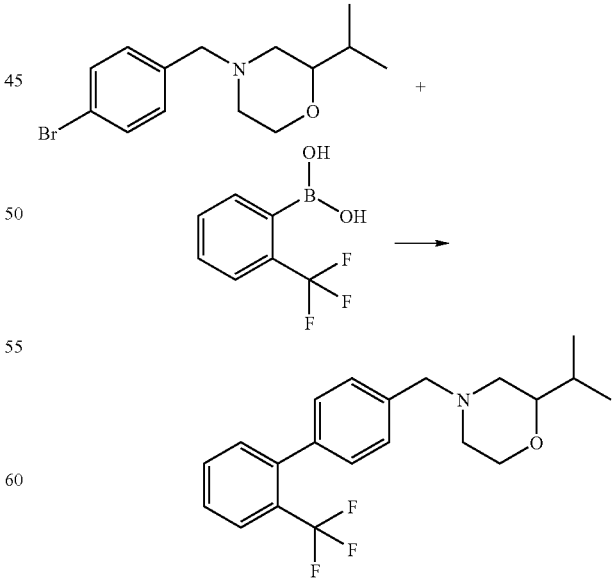

The above compound could be made in the following manner: 1 eq. of 4-(4-Bromo-benzyl)-2-isopropyl-morpholine could be combined with 1.5 eq. of 2-(Trifluoromethyl)phenyl boronic acid, 10 mol % of tetrakis(triphenylphosphine)palladium(0), 6.7 eq. of 2M sodium carbonate solution, toluene and ethanol. The reaction mixture could be heated in a sealed tube at 120° C. overnight in an oil bath. The reaction mixture is filtered through Celite and concentrated in vacuo. The residue could be diluted with water and extracted with ethyl acetate. The combined organic phases could be washed with brine, dried over sodium sulfate, filtered and concentrated in vacuo. The crude material could be purified by flash chromatography to afford product.

Example 60

1-(2'-Trifluoromethyl-biphenyl-4-ylmethyl)-piperazine 1-(4-Bromo-benzyl)-piperazine

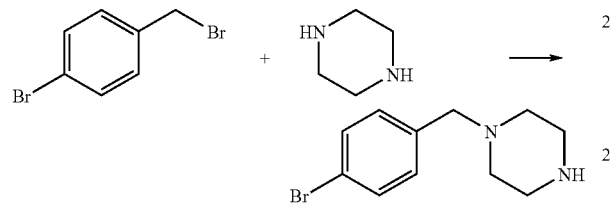

This compound could be made in the following manner: 2 g of 4-Bromobenzyl bromide and 1 equ. piperazine in acetonitrile would be stirred at room temperature and 1.1 g of potassium carbonate would be added. The reaction would be stirred at room temperature overnight. The solution would then be filtered through Celite and concentrated in vacuo to afford the crude product. Purification would be done by flash chromatography using a methylene chloride/methanol gradient.

1-(2'-Trifluoromethyl-biphenyl-4-ylmethyl)-piperazine

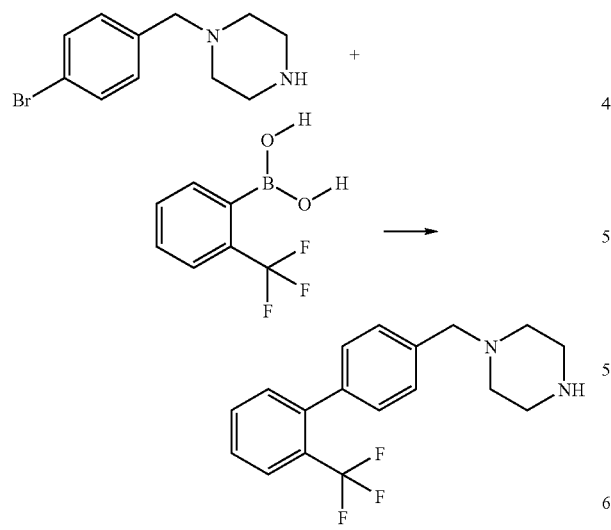

This compound could be made in the following manner: 1-(4-Bromo-benzyl)-piperazine would be combined with 1 equ of 2-(Trifluoromethyl)phenyl boronic acid, 10 mol % of tetrakis(triphenylphosphine)palladium(0), 2M sodium carbonate solution, toluene and ethanol. The reaction mixture would be heated in a sealed tube at 120° C. overnight in an oil bath. The reaction mixture would then be filtered through Celite and concentrated in vacuo. The residue would then be purified by flash chromatography.

Example 61

1-Methyl-2-phenyl-4-(2'-trifluoromethyl-biphenyl-4-ylmethyl)-piperazine

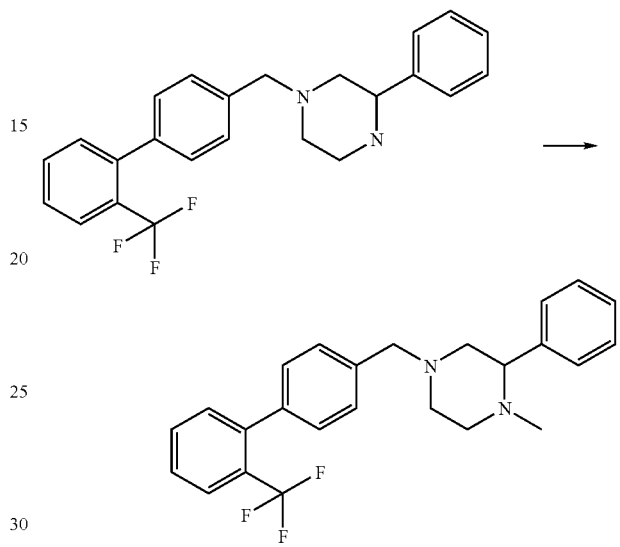

This compound could be made in the same manner as example 62 but with iodomethane as the appropriate alkylating agent.

Example 62

1-Ethyl-2-phenyl-4-(2'-trifluoromethyl-biphenyl-4-ylmethyl)-piperazine

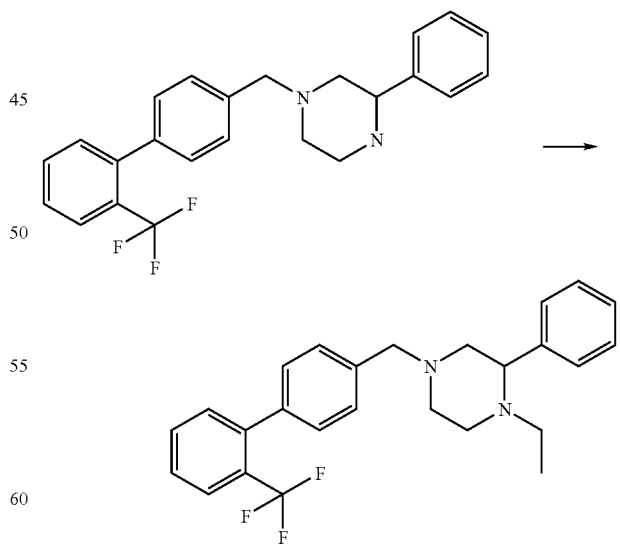

100 mg of 3-phenyl-1-(2'-trifluoromethyl-biphenyl-4-yl-methyl)-piperazine were dissolved in THF, 2 equiv. of N,N-diisopropylethylamine were added followed by 2 equiv. of bromoethane. The reaction was stirred at 80° C. overnight.

The reaction was diluted with dichloromethane and washed with 1N aqueous NaOH solution. The organic layers were dried over Na₂SO₄, filtered and concentrated in vacuo. The crude residue was purified by column chromatography to afford 1-ethyl-2-phenyl-4-(2'-trifluoromethyl-biphenyl-4-yl-methyl)-piperazine as the free base. Addition of 1 equiv. of 1M HCl in dioxane and drying in vacuo afforded the title compound as hydrochloride salt. Yield 35% ES MS m/z 425

Example 63

1-Isopropyl-2-phenyl-4-(2'-trifluoromethyl-biphenyl-4-ylmethyl)-piperazine

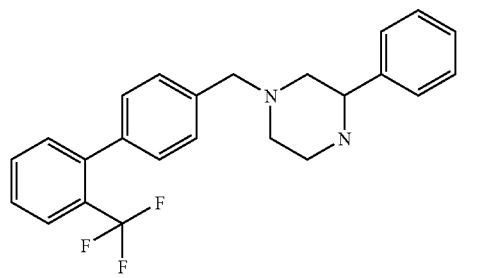

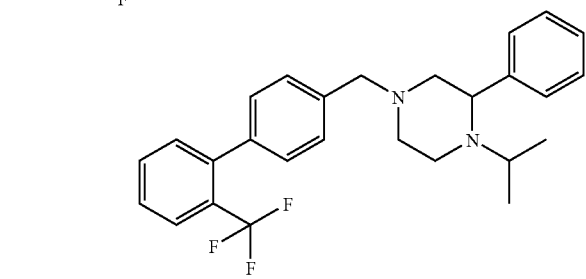

100 mg of 3-phenyl-1-(2'-trifluoromethyl-biphenyl-4-yl-methyl)-piperazine was dissolved in a 2:1 mixture of dichloroethane and acetone, 2 equiv. of sodium triacetoxyborohydride was added followed by 30 μL of acetic acid. The reaction was stirred at room temperature under nitrogen overnight. The reaction was diluted with 5 mL of dichloromethane. The reaction mixture was washed with 1M aqueous sodium hydroxide solution and brine, then dried over sodium sulfate, filtered and concentrated in vacuo. The crude residue was purified by column chromatography to afford the title compound. Yield 41% ES MS m/z 439.

Example 64

1-Cyclohexyl-2-phenyl-4-(2'-trifluoromethyl-biphenyl-4-ylmethyl)-piperazine

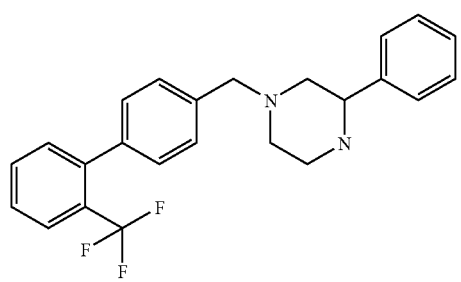

-continued

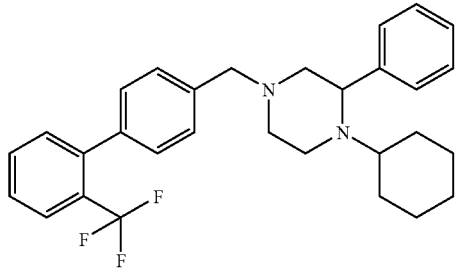

The above compound could be made in the same manner as example 62, but with bromo cyclohexane as the appropriate alkylating reagent.

Example 65

1-[2-Phenyl-4-(2'-trifluoromethyl-biphenyl-4-ylm-ethyl)-piperazin-1-yl]-ethanone

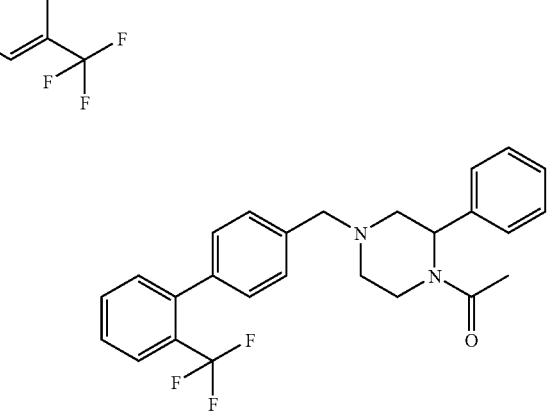

55 mg of 3-phenyl-1-(2'-trifluoromethyl-biphenyl-4-ylm-ethyl)-piperazine was dissolved in THF, 2 equiv. of acetyl-chloride and 2 equiv. of N,N-diisoproylethylamine were added. The reaction was shaken at room temperature overnight. The solvent was removed in vacuo, the residue was dissolved in DCM, washed with 1M aqueous sodium hydroxide solution, then dried over sodium sulfate, filtered and concentrated in vacuo. The crude residue was purified by column chromatography to afford the title compound as free base. Addition of 1 equiv. of 1M HCl in dioxane and concentration in vacuo afforded 27 mg of the title compound as hydrochloride salt. Yield 40% ES MS m/z 439

Example 66

Phenyl-[2-phenyl-4-(2'-trifluoromethyl-biphenyl-4-ylmethyl)-piperazin-1-yl]-methanone

Example 68

2-Phenyl-1-[2-phenyl-4-(2'-trifluoromethyl-biphenyl-4-ylmethyl)-piperazin-1-yl]-ethanone

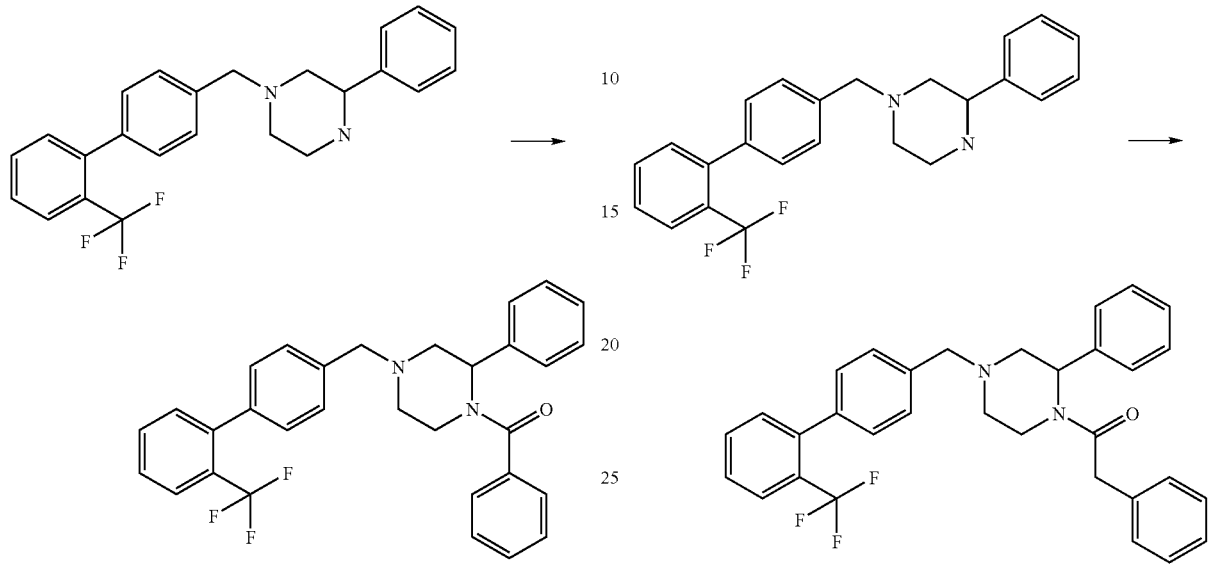

The hydrochloride salt of the above compound was made in the same manner as example 65, but with benzoylchloride as the appropriate acidchloride. Yield 54%, ES MS m/z 502

The hydrochloride salt of the above compound was made in the same manner as example 65, but with phenylacetyl chloride as the appropriate acidchloride. Yield 42%, ES MS m/z 515

Example 67

2,2-Dimethyl-1-[2-phenyl-4-(2'-trifluoromethyl-biphenyl-4-ylmethyl)-piperazin-1-yl]-propan-1-one

Example 69

2-Phenyl-4-(2'-trifluoromethyl-biphenyl-4-ylmethyl)-piperazine-1-carboxylic acid methylamide

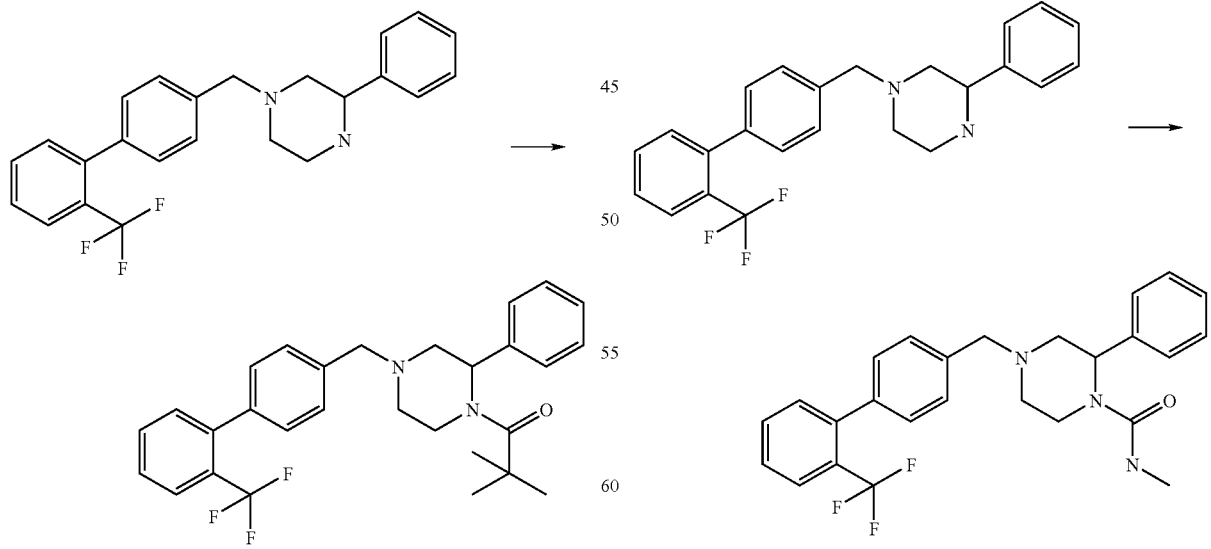

The hydrochloride salt of the above compound was made in the same manner as example 65, but with pivaloylchloride as the appropriate acidchloride. Yield 48%, ES MS m/z 481

This compound was made in the following manner: 55 mg of 3-phenyl-1-(2'-trifluoromethyl-biphenyl-4-ylmethyl)-piperazine was dissolved in THF, 2 equiv. methylisocyanate were added. The reaction was shaken at room temperature overnight. The solvent was removed in vacuo, the residue was dissolved in DCM, washed with 1M aqueous sodium hydroxide solution, then dried over sodium sulfate, filtered and concentrated in vacuo. The crude residue was purified by column chromatography to afford the title compound as free base. Addition of 1 equiv. of 1M HCl in dioxane and concentration in vacuo afforded 33 mg of the title compound as hydrochloride salt. Yield 48% ES MS m/z 454

Example 70

2-Phenyl-4-(2'-trifluoromethyl-biphenyl-4-ylmethyl)-piperazine-1-carboxylic acid dimethylamide

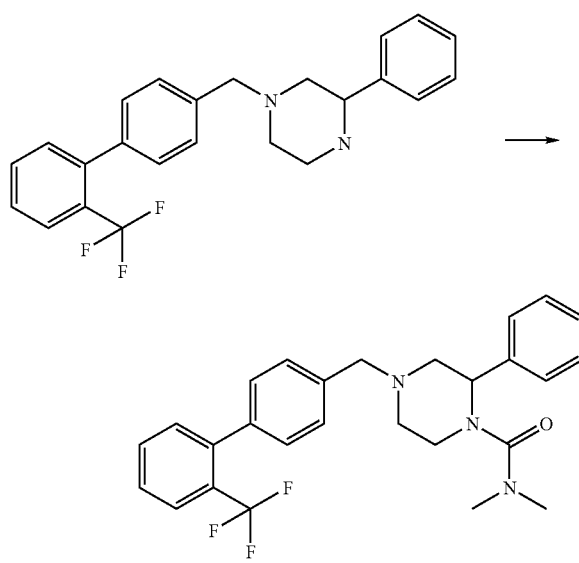

The hydrochloride salt of the above compound was made in the same manner as example 69, but with N,N-dimethylcarbamoyl chloride as the appropriate acidchloride. Yield 48%, ES MS m/z 468

Example 71

2-Phenyl-4-(2'-trifluoromethyl-biphenyl-4-ylmethyl)-piperazine-1-carboxylic acid phenylamide

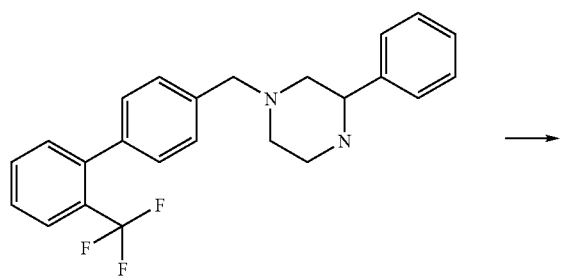

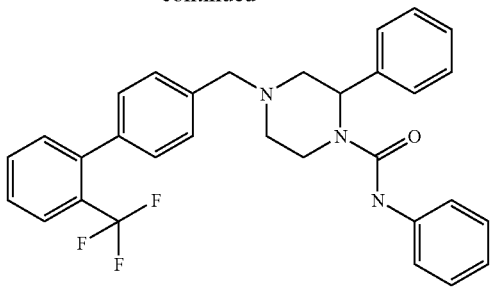

The hydrochloride salt of the above compound was made in the same manner as example 69, but with phenylisocyanate as the appropriate isocyanate. Yield 35%, ES MS m/z 516

Example 72

1-Methanesulfonyl-2-phenyl-4-(2'-trifluoromethyl-biphenyl-4-ylmethyl)-piperazine

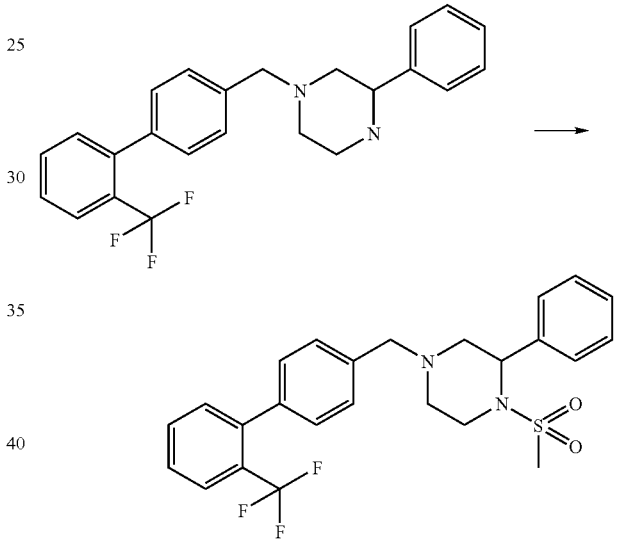

The hydrochloride salt of the above compound was made in the same manner as example 65, but with methanesulfonyl chloride as the appropriate acid chloride. Yield 44%, ES MS m/z 475.

Example 73

1-Benzenesulfonyl-2-phenyl-4-(2'-trifluoromethyl-biphenyl-4-ylmethyl)-piperazine

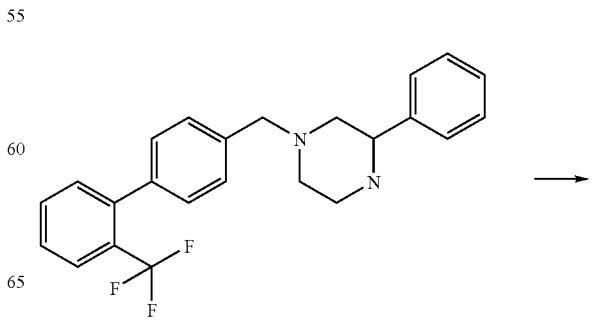

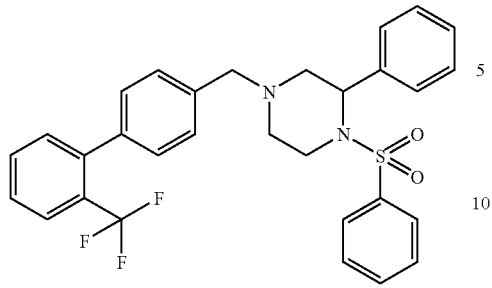

The above compound was made in the same manner as example 65, but with of benzenesulfonyl chloride as the appropriate acidchloride. Yield 59%, ES MS m/z 537

Example 74

1-Cyclohexanesulfonyl-2-phenyl-4-(2'-trifluoromethyl-biphenyl-4-ylmethyl)-piperazine

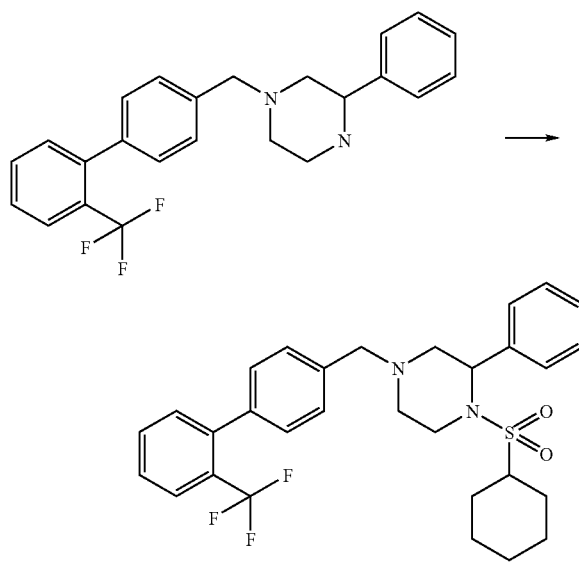

The above compound could be made in the same manner as example 65, but with of cyclohexanesulfonyl chloride as the appropriate acidchloride.

Example 75

1-Methyl-2-phenyl-4-(2'-chloro-biphenyl-4-ylmethyl)-piperazine

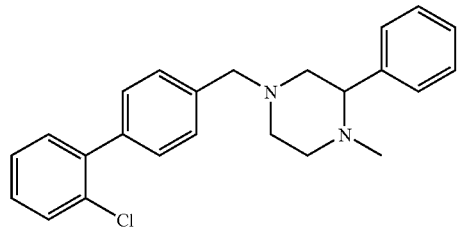

This compound could be made the following manner: 100 mg of 3-phenyl-1-(2'-trifluoromethyl-biphenyl-4-ylmethyl)-piperazine would be dissolved in acetonitrile, 3 equiv. of N,N-diisopropylethylamine would be added followed by 1.1 equiv. of iodomethane. The reaction would be stirred at 80° C. overnight. The reaction would be diluted with dichloromethane and washed with 1N aqueous NaOH solution. The organic layer would be dried over Na2SO4, filtered and concentrated in vacuo. The crude residue would be purified by column chromatography to afford 1-methyl-2-phenyl-4-(2'-chloro-biphenyl-4-ylmethyl)-piperazine.

Example 76

1-Ethyl-2-phenyl-4-(2'-chloro-biphenyl-4-ylmethyl)-piperazine

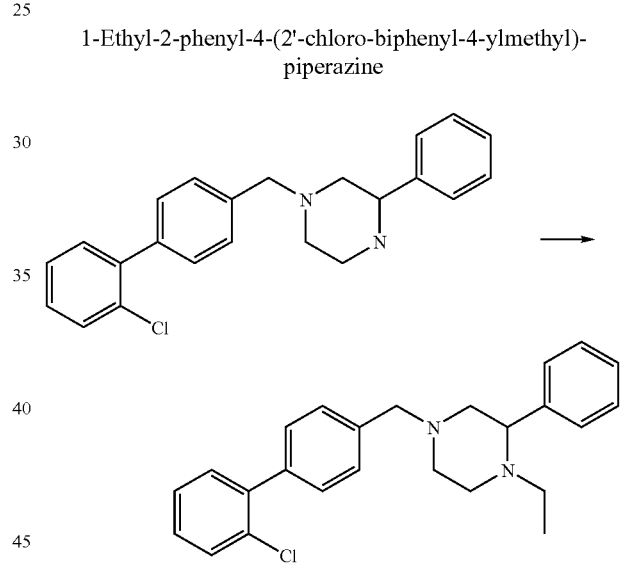

The above compound could be made in the same manner as example 75, but with iodoethane as the appropriate alkylating reagent.

Example 77

1-Isopropyl-2-phenyl-4-(2'chloro-biphenyl-4-ylmethyl)-piperazine

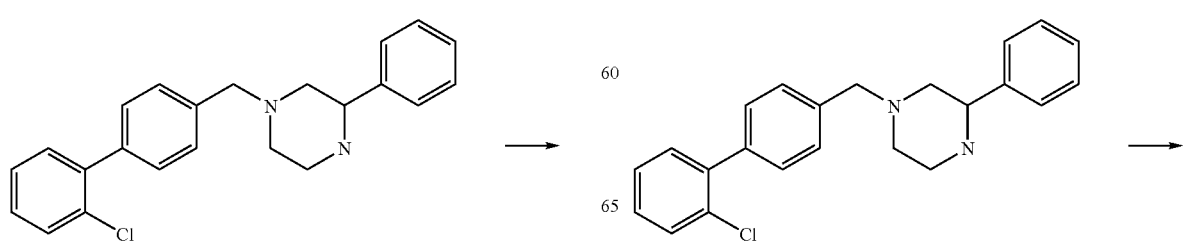

-continued

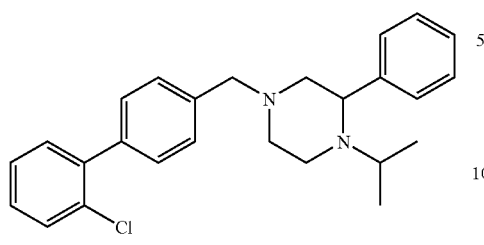

This compound could be made the following manner: 100 mg of 3-phenyl-1-(2'-chloro-biphenyl-4-ylmethyl)-piperazine would be dissolved in a 2:1 mixture of dichloroethane and acetone, 2 equiv. of sodium triacetoxyborohydride would be added followed by 30 µL of acetic acid. The reaction would be stirred at room temperature under nitrogen overnight. The reaction would be diluted with 5 mL of dichloromethane. The reaction mixture would be washed with 1M aqueous sodium hydroxide solution and brine, then dried over sodium sulfate, filtered and concentrated in vacuo. The crude residue would be purified by column chromatography to afford the title compound.

Example 78

1-Cyclohexyl-2-phenyl-4-(2'-chloro-biphenyl-4-ylmethyl)-piperazine

The above compound could be made in the same manner as example 75, but with cyclohexylbromide as the appropriate alkylating reagent.

Example 79

1-[2-Phenyl-4-(2'-chloro-biphenyl-4-ylmethyl)-piperazin-1-yl]-ethanone

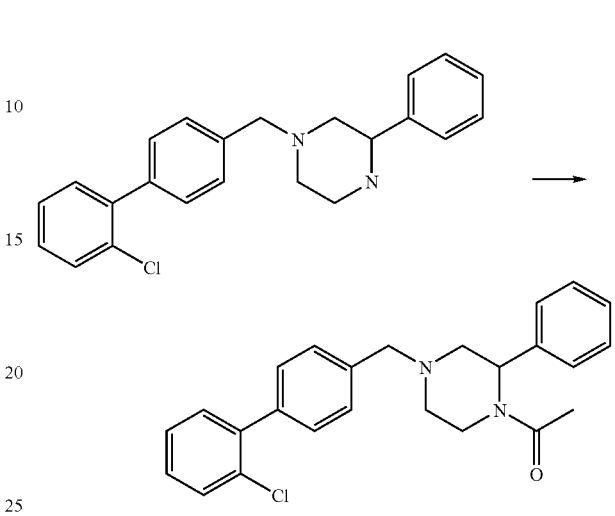

This compound could be made the following manner: 100 mg of 3-phenyl-1-(2'-chloro-biphenyl-4-ylmethyl)-piperazine would be dissolved in dichloromethane, 1.1 equiv. of acetylchloride and 2 equiv. of N,N-diisoproylethylamine would be added. The reaction would be stirred at room temperature under nitrogen overnight. The reaction would be diluted with DCM, washed with 1M aqueous sodium hydroxide solution, then dried over sodium sulfate, filtered and concentrated in vacuo. The crude residue would be purified by column chromatography to afford the title compound.

Example 80

Phenyl-[2-phenyl-4-(2'-chloro-biphenyl-4-ylmethyl)-piperazin-1-yl]-methanone

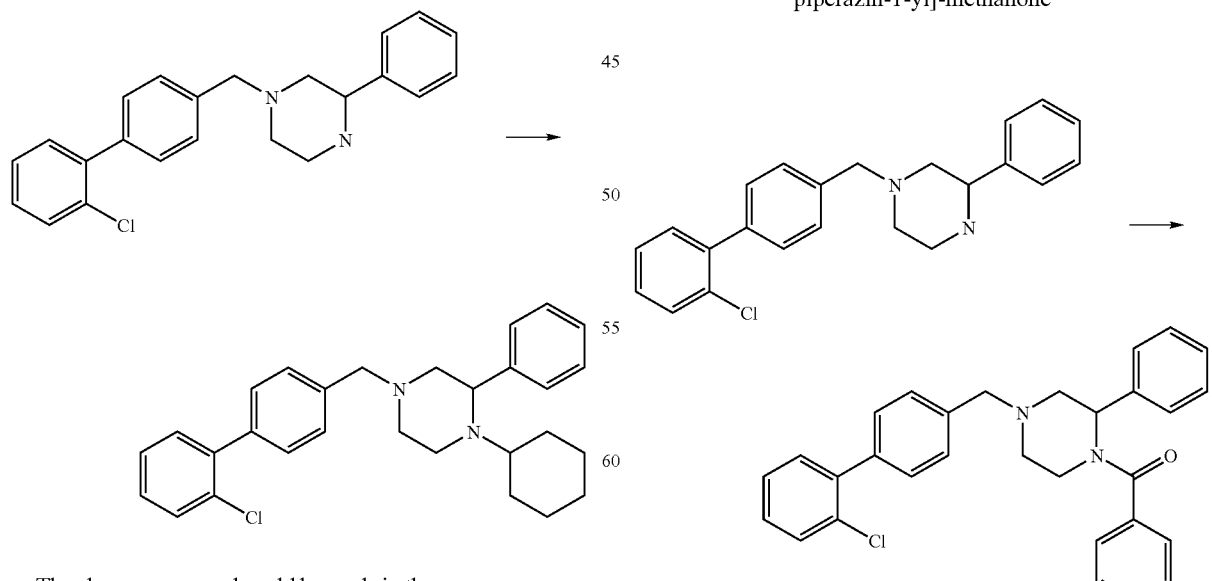

The above compound could be made in the same manner as example 84, but with benzoylchloride as the appropriate acidchloride.

Example 81

2,2-Dimethyl-1-[2-phenyl-4-(2'-chloro-biphenyl-4-ylmethyl)-piperazin-1-yl]-propan-1-one

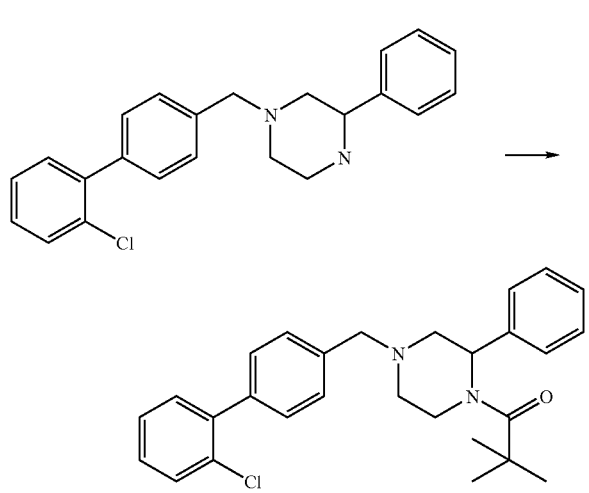

The above compound could be made in the same manner as example 79, but with pivaloylchloride as the appropriate acidchloride.

Example 82

2-Phenyl-1-[2-phenyl-4-(2'-chloro-biphenyl-4-ylmethyl)-piperazin-1-yl]-ethanone

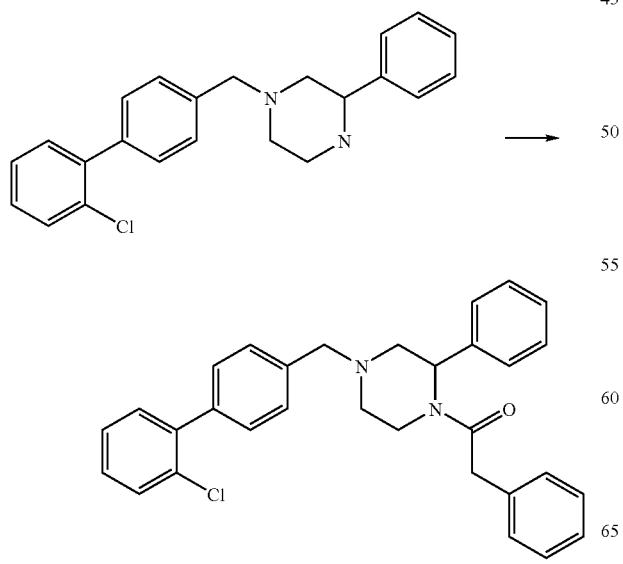

The above compound could be made in the same manner as example 79, but with phenylacetyl chloride as the appropriate acidchloride.

Example 83

2-Phenyl-4-(2'-chloro-biphenyl-4-ylmethyl)-piperazine-1-carboxylic acid methylamide

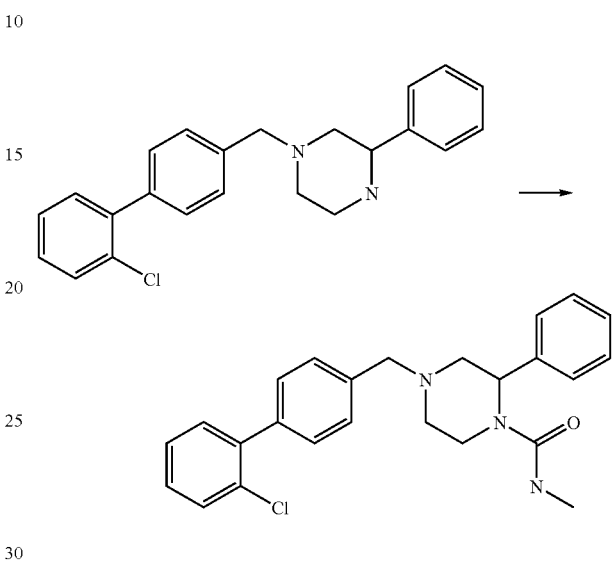

This compound could be made in the following manner: 100 mg of 3-phenyl-1-(2'-chloro-biphenyl-4-ylmethyl)-piperazine would be dissolved in dichloromethane, 1.1 equiv. methylisocyanate would be added. The reaction would be stirred at room temperature under nitrogen overnight. Aminomethylpolystyrene (loading 1.6 mmol/g) could be added and the reaction would be shaken for further 6 h. The polymer could be separated by filtration and rinsed with dichloromethane. The filtrate could be concentrated in vacuo to afford the title compound.

Example 84

2-Phenyl-4-(2'-chloromethyl-biphenyl-4-ylmethyl)-piperazine-1-carboxylic acid dimethylamide

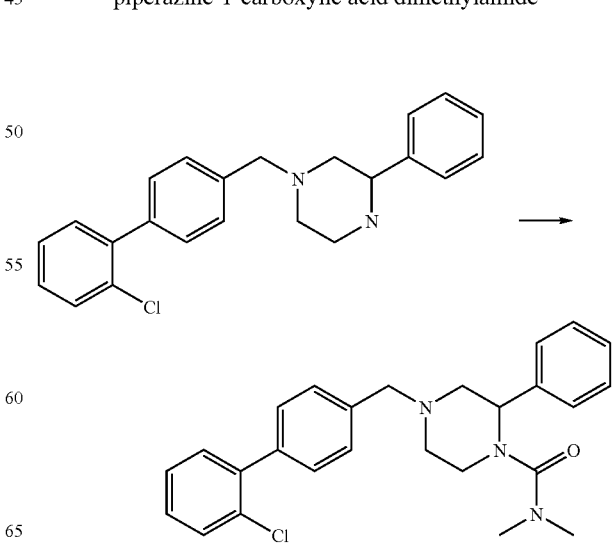

The above compound could be made in the same manner as example 79, but with N,N-dimethylcarbamoyl chloride as the appropriate acidchloride.

Example 85

2-Phenyl-4-(2'-chloro-biphenyl-4-ylmethyl)-piperazine-1-carboxylic acid phenylamide

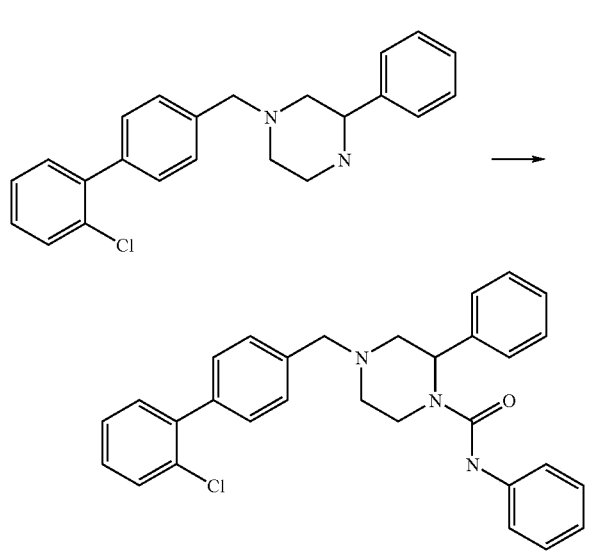

The above compound could be made in the same manner as example 83, but with phenylisocyanate as the appropriate isocyanate.

Example 86

1-Methanesulfonyl-2-phenyl-4-(2'-chloro-biphenyl-4-ylmethyl)-piperazine

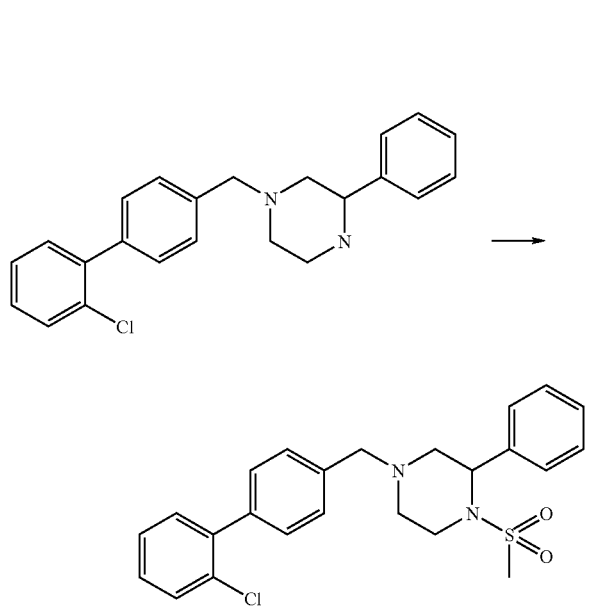

The above compound could be made in the same manner as example 79, but with of methanesulfonyl chloride as the appropriate acidchloride.

Example 87

1-Benzenesulfonyl-2-phenyl-4-(2'-chloro-biphenyl-4-ylmethyl)-piperazine

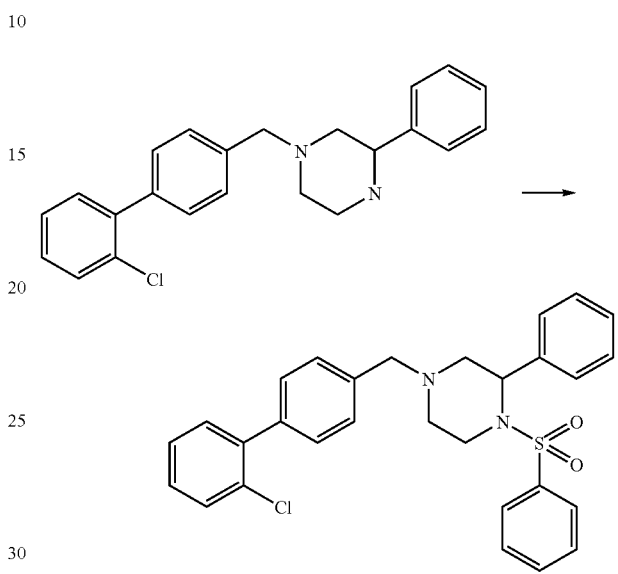

The above compound could be made in the same manner as example 79, but with of benzenesulfonyl chloride as the appropriate acidchloride.

Example 88

1-Cyclohexanesulfonyl-2-phenyl-4-(2'-chloro-biphenyl-4-ylmethyl)-piperazine

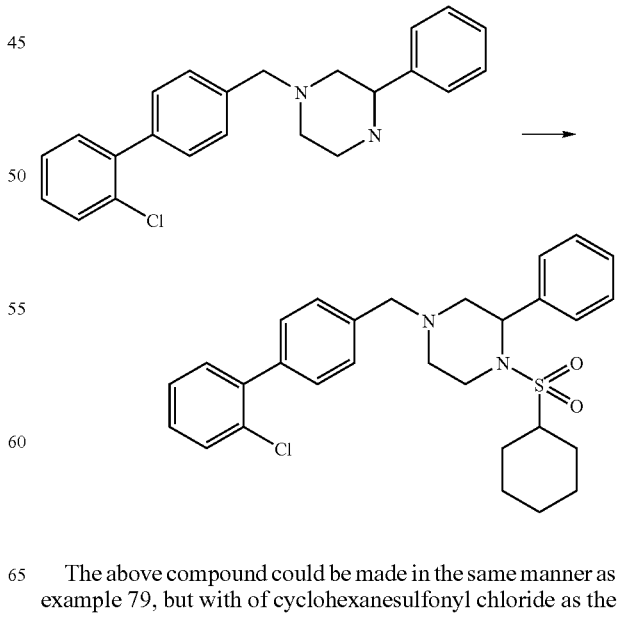

The above compound could be made in the same manner as example 79, but with of cyclohexanesulfonyl chloride as the appropriate acidchloride.

Example 89

1-Methyl-2-phenyl-4-(2'-chloro-5'-methyl-biphenyl-4-ylmethyl)-piperazine

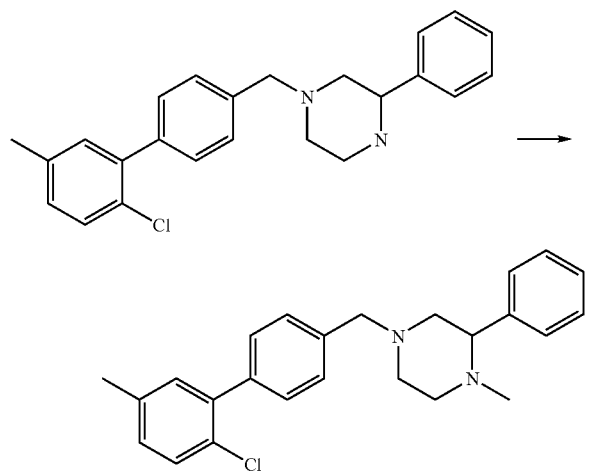

This compound could be made the following manner: 100 mg of 3-phenyl-1-(2'-trifluoromethyl-biphenyl-4-ylmethyl)-piperazine would be dissolved in acetonitrile, 3 equiv. of N,N-diisopropylethylamine would be added followed by 1.1 equiv. of iodomethane. The reaction would be stirred at 80° C. overnight. The reaction would be diluted with dichloromethane and washed with 1N aqueous NaOH solution. The organic layer would be dried over Na2SO4, filtered and concentrated in vacuo. The crude residue would be purified by column chromatography to afford 1-methyl-2-phenyl-4-(2'-chloro-5'-methyl-biphenyl-4-ylmethyl)-piperazine.

Example 90

1-Ethyl-2-phenyl-4-(2'-chloro-5'-methyl-biphenyl-4-ylmethyl)-piperazine

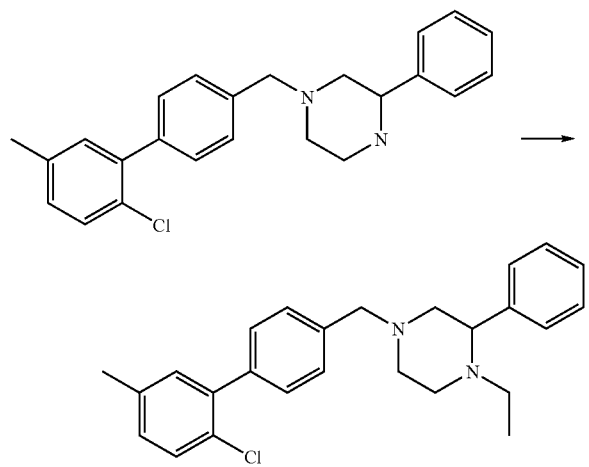

The above compound could be made in the same manner as Example 89, but with iodoethane as the appropriate alkylating reagent.

Example 91

1-Isopropyl-2-phenyl-4-(2'chloro-5'methyl-biphenyl-4-ylmethyl)-piperazine

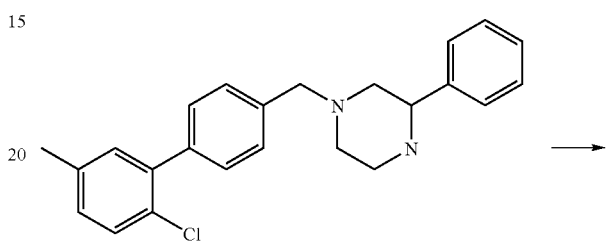

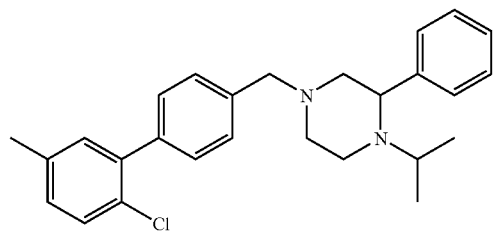

This compound could be made the following manner: 100 mg of 3-phenyl-1-(2'-chloro-5'-methyl-biphenyl-4-ylmethyl)-piperazine would be dissolved in a 2:1 mixture of dichloroethane and acetone, 2 equiv. of sodium triacetoxyborohydride would be added followed by 30 μL of acetic acid. The reaction would be stirred at room temperature under nitrogen overnight. The reaction would be diluted with 5 mL of dichloromethane. The reaction mixture would be washed with 1M aqueous sodium hydroxide solution and brine, then dried over sodium sulfate, filtered and concentrated in vacuo. The crude residue would be purified by column chromatography to afford the title compound.

Example 92

1-Cyclohexyl-2-phenyl-4-(2'-chloro-5'methyl-biphenyl-4-ylmethyl)-piperazine

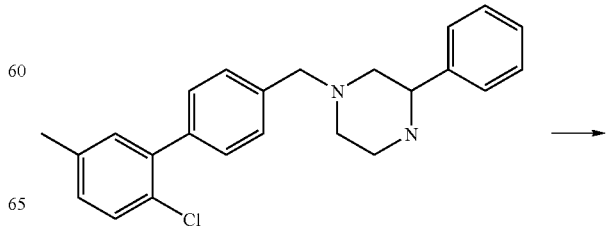

-continued

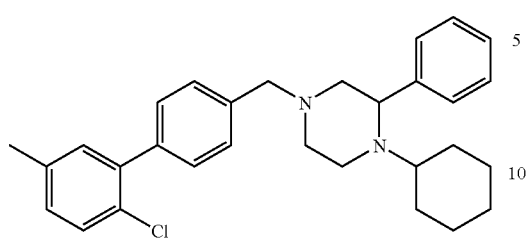

The above compound could be made in the same manner as example 90, but with cyclohexanone as the appropriate alkylating reagent.

Example 93

1-[2-Phenyl-4-(2'-chloro-5'methyl-biphenyl-4-ylmethyl)-piperazin-1-yl]-ethanone

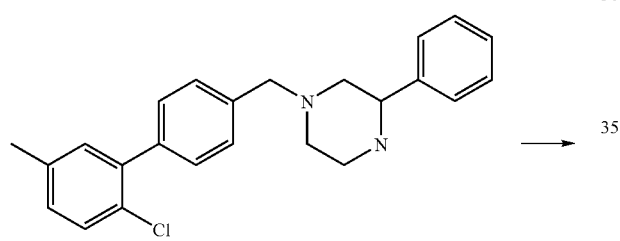

This compound was made the following manner: 55 mg of 3-phenyl-1-(2'-chloro-5'-methyl-biphenyl-4-ylmethyl)-piperazine were dissolved in THF, 2 equiv. of acetylchloride and 2 equiv. of N,N-diisoproylethylamine were added. The reaction was shaken at room temperature overnight. The reaction was concentrated in vacuo. The residue was diluted with DCM, washed with 1M aqueous sodium hydroxide solution, then dried over sodium sulfate, filtered and concentrated in vacuo. The crude residue was purified by column chromatography to afford the title compound as free base. Addition of 1 equiv. of 1M HCl in dioxane and concentratation in vacuo afforded 43 mg of the title compound as hydrochloride salt. Yield 67%, ES MS m/z 419

Example 94

Phenyl-[2-phenyl-4-(2'-chloro-5' methyl-biphenyl-4-ylmethyl)-piperazin-1-yl]-methanone

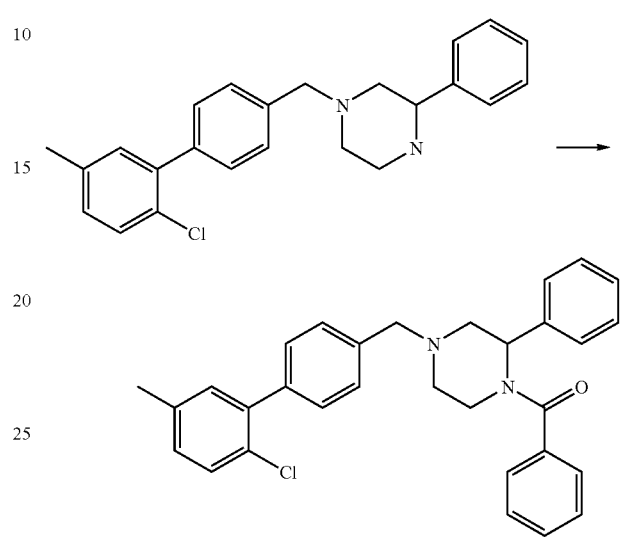

The hydrochloride salt of the above compound was made in the same manner as example 93, but with benzoylchloride as the appropriate acidchloride. Yield 44%, ES MS m/z 481

Example 95

2,2-Dimethyl-1-[2-phenyl-4-(2'-chloro-5'-methyl-biphenyl-4-ylmethyl)-piperazin-1-yl]-propan-1-one

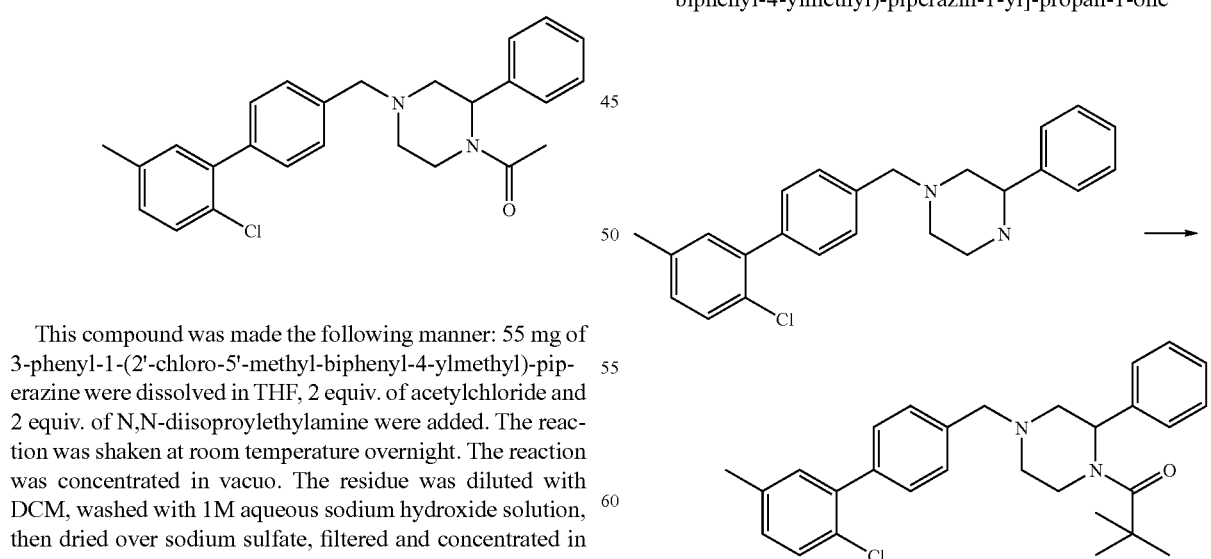

The above compound could be made in the same manner as example 93, but with pivaloylchloride as the appropriate acidchloride.

Example 96

2-Phenyl-1-[2-phenyl-4-(2'-chloro-5'-methyl-biphenyl-4-ylmethyl)-piperazin-1-yl]-ethanone

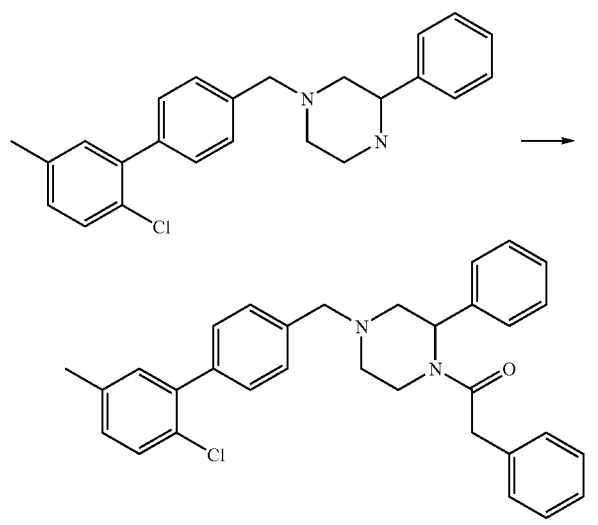

The above compound could be made in the same manner as example 93, but with phenylacetyl chloride as the appropriate acidchloride.

Example 97

2-Phenyl-4-(2'-chloro-5'methyl-biphenyl-4-ylmethyl)-piperazine-1-carboxylic acid methylamide

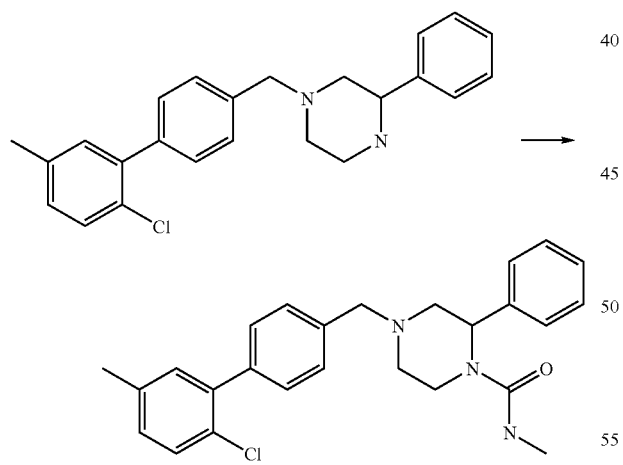

This compound could be made in the following manner: 55 mg of 3-phenyl-1-(2'-chloro-5'-methyl-biphenyl-4-ylmethyl)-piperazine would be dissolved in dichloromethane, 2 equiv. methylisocyanate would be added. The reaction would be shaken at room temperature overnight. The reaction would be concentrated in vacuo. The residue would be diluted with DCM, washed with 1M aqueous sodium hydroxide solution, then dried over sodium sulfate, filtered and concentrated in vacuo. The crude residue would be purified by column chromatography to afford the title compound as free base. Addition of 1 equiv. of 1M HCl in dioxane and concentratation in vacuo would afford the title compound as hydrochloride salt.

Example 98

2-Phenyl-4-(2'-chloro-5'-methyl-biphenyl-4-ylmethyl)-piperazine-1-carboxylic acid dimethylamide

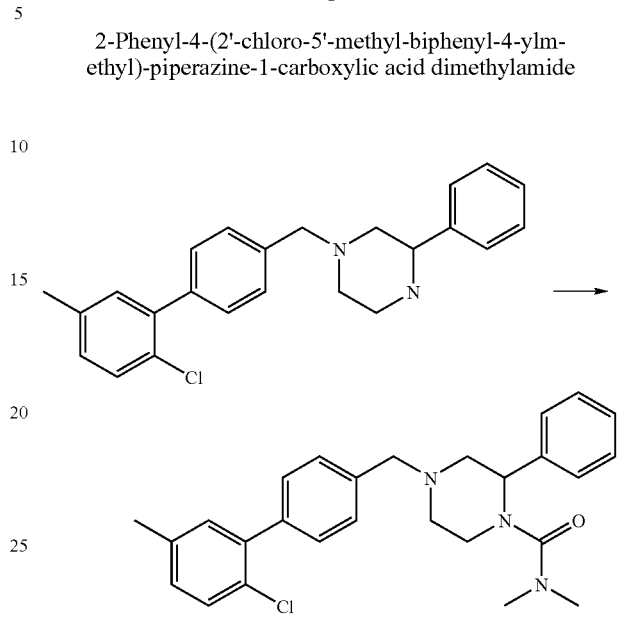

The above compound could be made in the same manner as example 93, but with N,N-dimethylcarbamoyl chloride as the appropriate acidchloride.

Example 99

2-Phenyl-4-(2'-chloro-5'-methyl-biphenyl-4-ylmethyl)-piperazine-1-carboxylic acid phenylamide

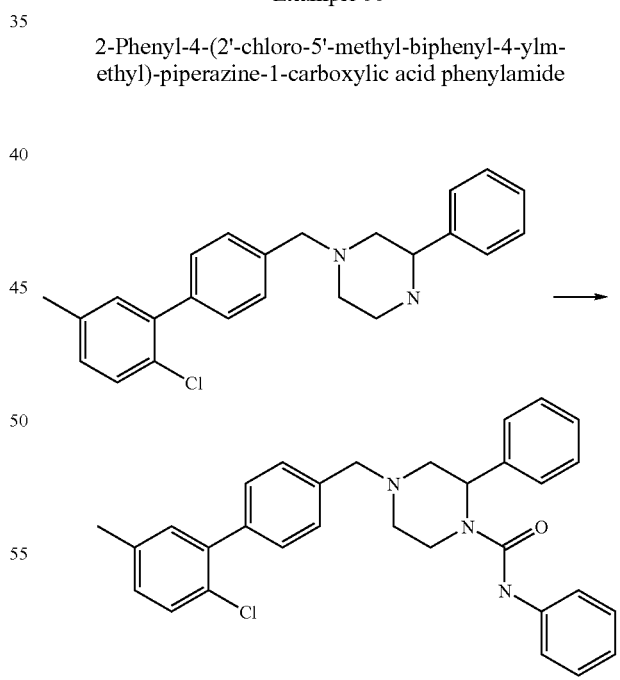

55 mg of 3-phenyl-1-(2'-chloro-5'-methyl-biphenyl-4-ylmethyl)-piperazine were dissolved in dichloromethane, 2 equiv. methylisocyanate were added. The reaction was shaken at room temperature overnight. The reaction was concentrated in vacuo. The residue was diluted with DCM, washed with 1M aqueous sodium hydroxide solution, then dried over sodium sulfate, filtered and concentrated in vacuo. The crude residue was purified by column chromatography to afford the title compound as free base. Addition of 1 equiv. of 1M HCl in dioxane and concentratation in vacuo afforded the title compound as hydrochloride salt. Yield 33%, ES MS m/z 496.

Example 100

1-Methanesulfonyl-2-phenyl-4-(2'-chloro-5'-methyl-biphenyl-4-ylmethyl)-piperazine

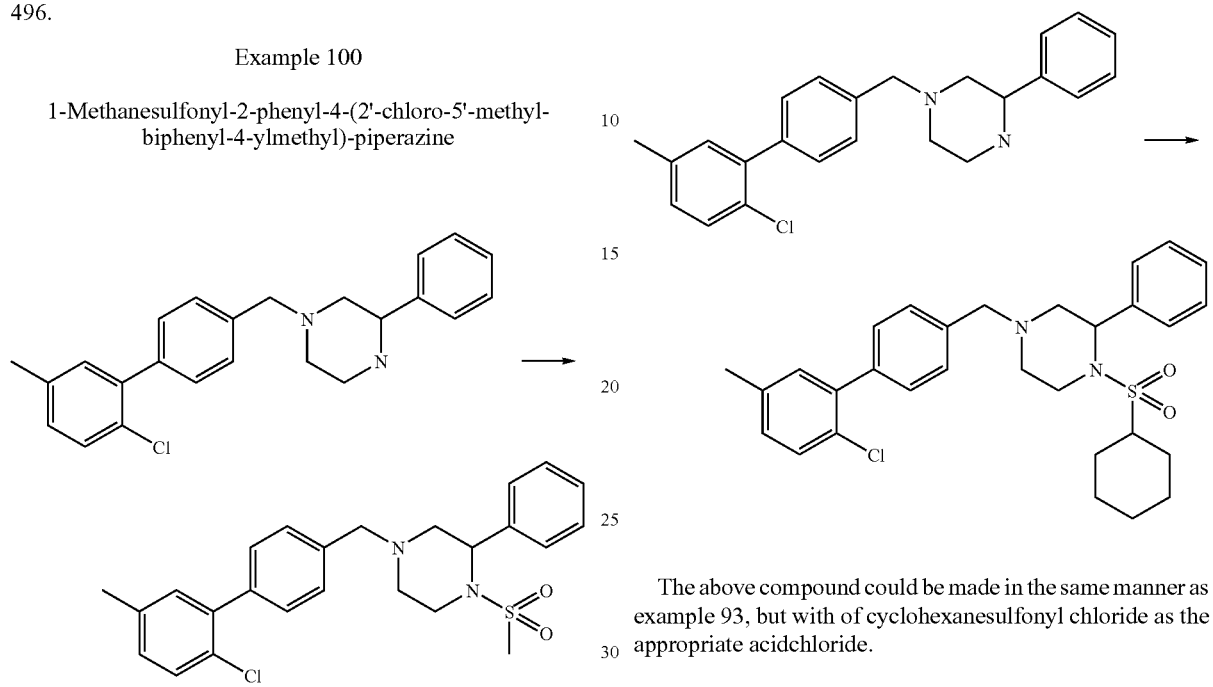

The hydrochloride salt of the above compound was made in the same manner as example 93, but with methanesulfonyl chloride as the appropriate acidchloride. Yield 49%, ES MS m/z 455

Example 101

1-Benzenesulfonyl-2-phenyl-4-(2'-chloro-5'-methyl-biphenyl-4-ylmethyl)-piperazine

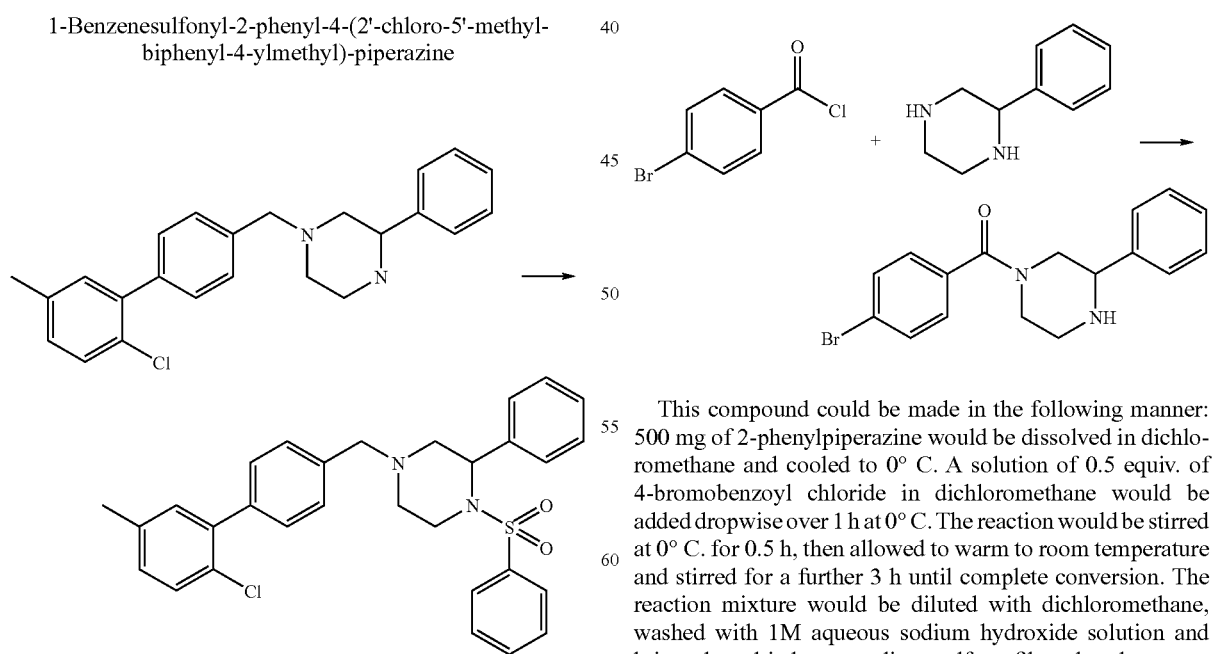

The above compound could be made in the same manner as example 93, but with of benzenesulfonyl chloride as the appropriate acidchloride.

Example 102

1-Cyclohexanesulfonyl-2-phenyl-4-(2'-chloro-5'-methyl-biphenyl-4-ylmethyl)-piperazine

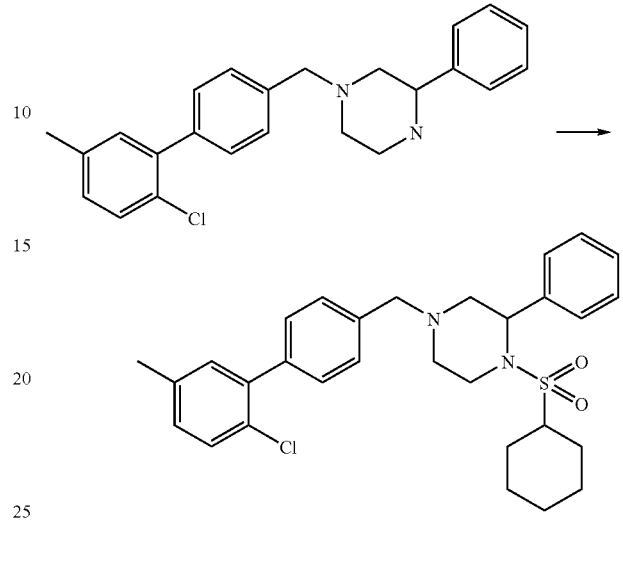

The above compound could be made in the same manner as example 93, but with of cyclohexanesulfonyl chloride as the appropriate acidchloride.

Example 103

(3-Phenyl-piperazin-1-yl)-(2'-trifluoromethyl-biphenyl-4-yl)-methanone (4-Bromo-phenyl)-(3-phenyl-piperazin-1-yl)-methanone

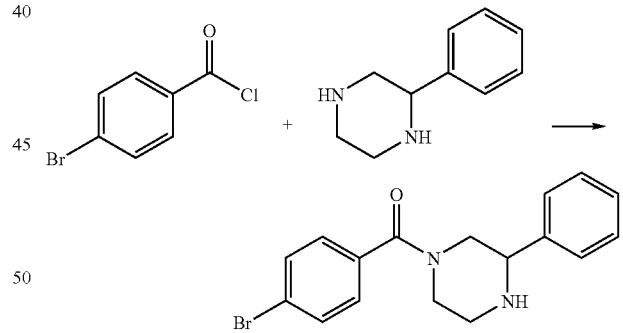

This compound could be made in the following manner: 500 mg of 2-phenylpiperazine would be dissolved in dichloromethane and cooled to 0° C. A solution of 0.5 equiv. of 4-bromobenzoyl chloride in dichloromethane would be added dropwise over 1 h at 0° C. The reaction would be stirred at 0° C. for 0.5 h, then allowed to warm to room temperature and stirred for a further 3 h until complete conversion. The reaction mixture would be diluted with dichloromethane, washed with 1M aqueous sodium hydroxide solution and brine, then dried over sodium sulfate, filtered and concentrated in vacuo. The crude residue would be purified by column chromatography to afford (4-bromo-phenyl)-(3-phenyl-piperazin-1-yl)-methanone.

(3-Phenyl-piperazin-1-yl)-(2'-trifluoromethyl-biphenyl-4-yl)-methanone

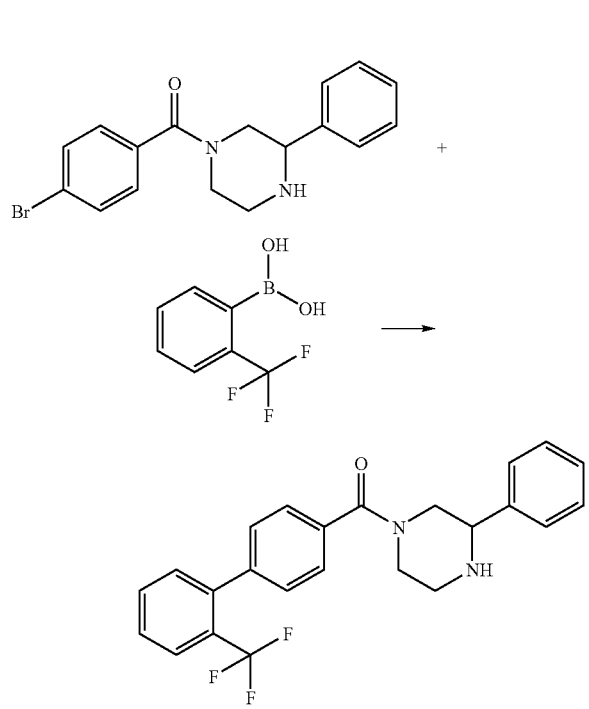

This compound could be made in the following manner: 100 mg of (4-bromo-phenyl)-(3-phenyl-piperazin-1-yl)-methanone would be combined with 1 equiv. of 2-trifluoromethylphenyl boronic acid, 10 mol % of tetrakis(triphenylphosphine) palladium(0), 2M aqueous sodium carbonate solution, toluene and ethanol. The reaction mixture would be heated in a sealed tube at 120° C. overnight. The reaction mixture would be filtered through Celite and concentrated in vacuo. The residue would be diluted with water and extracted with ethyl acetate. The combined organic phases would be washed with brine, dried over sodium sulfate, filtered and concentrated in vacuo. The crude material would be purified by flash chromatography to afford (3-phenyl-piperazin-1-yl)-(2'-trifluoromethyl-biphenyl-4-yl)-methanone.

Example 104

(4-Methyl-3-phenyl-piperazin-1-yl)-(2'-trifluoromethyl-biphenyl-4-yl)-methanone

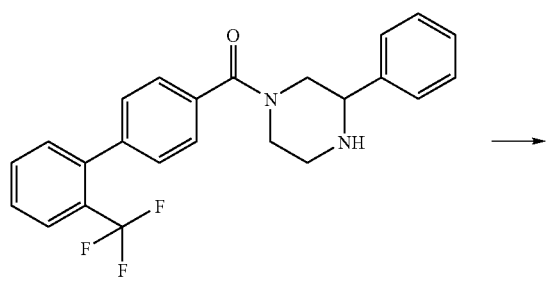

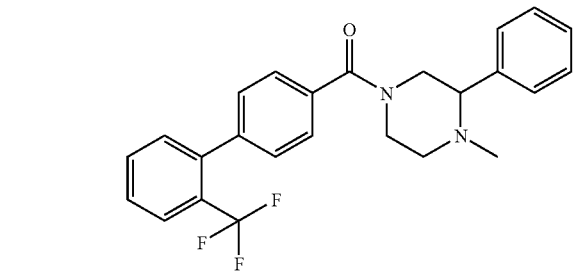

This compound could be made in the following manner: 100 mg of (3-phenyl-piperazin-1-yl)-(2'-trifluoromethyl-biphenyl-4-yl)-methanone would be dissolved in 3 mL of acetonitrile, 2 equiv. of N,N-diisopropylethylamine would be added followed by 1.1 equiv. of iodomethane. The reaction would be heated to 80° C. overnight. After cooling to room temperature, the reaction would be diluted with dichloromethane and washed with 1M aqueous sodium hydroxide solution, dried over sodium sulfate and concentrated in vacuo. The crude residue would be purified by column chromatography to afford the title compound.

Example 105

(S) 3-Benzyl-1-(2'-trifluoromethyl-biphenyl-4-ylmethyl)-piperazine

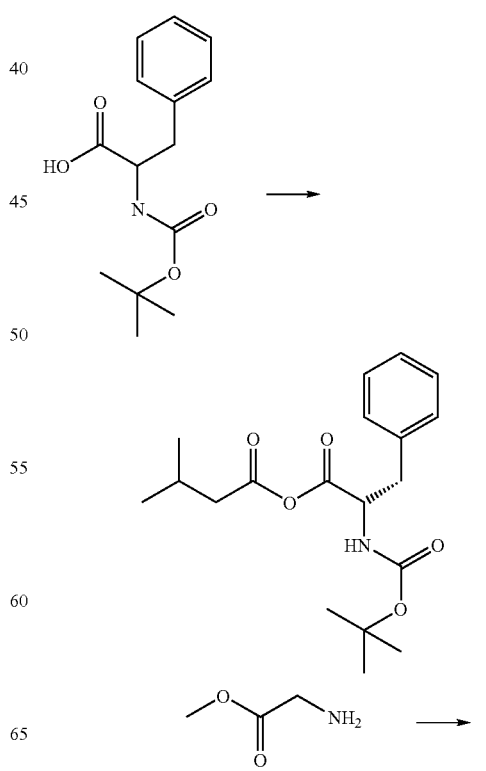

-continued

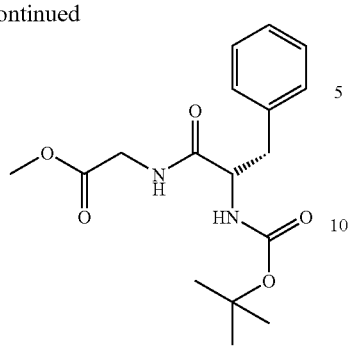

4 g of N-tert-butoxycarbonyl (L)-phenylalanine were dissolved in THF under nitrogen atmosphere and cooled to 0° C. 1.1 equiv. of triethylamine were added, followed by 1.1 equiv. of isobutylchloroformate to form the mixed anhydride solution. The reaction was stirred at room temperature for 1 h. 1.1 equiv. of the HCl salt of glycine methyl ester were dissolved in anhydrous dichloromethane, 1 eqiv. triethylamine were added. This solution was then added dropwise to the cooled, mixed anhydride solution. The reaction was stirred for 3 h at 0° C. The reaction was filtered and the filtrate concentrated in vacuo. The residue was taken up into ethyl acetate, washed with 5% aqueous citric acid solution, 5% aqueous sodium bicarbonate solution, water and brine. The organic phase was dried over sodium sulfate, filtered and concentrated in vacuo to afford in a quantitative yield (S)-(2-tert-Butoxycarbonylamino-3-phenyl-propionylamino)-acetic acid methyl ester as colorless oil. ES MS(+) m/z 337

3-(S)-Benzyl-piperazine-2,5-dione

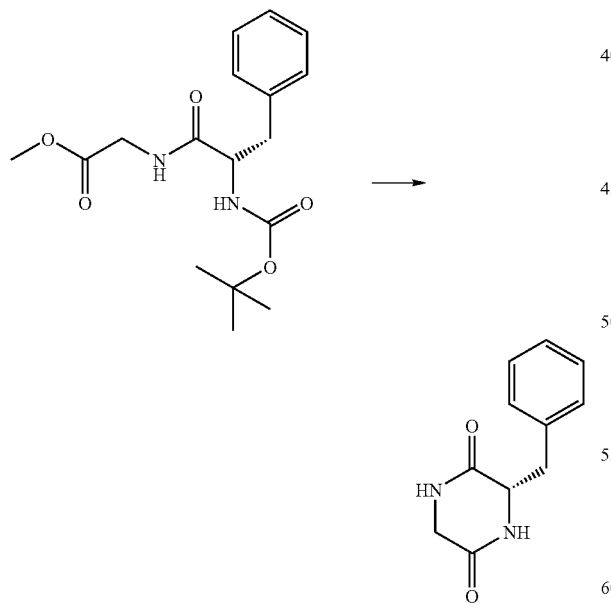

5 g of (S)-(2-tert-Butoxycarbonylamino-3-phenyl-propionylamino)-acetic acid methyl ester were dissolved in dichloromethane and trifluoroacetic acid was added.

The reaction was stirred at room temperature for 2.5 h. The reaction was concentrated in vacuo to give a yellow oil which was re-dissolved in 5% aqueous sodium bicarbonate solution. The reaction was stirred at room temperature for 20 min, then methanol was added. The reaction was heated to 80° C. for 3 h. After cooling to room temperature, the basic aqueous phase was extracted with ethyl acetate. The combined organic extracts were dried over sodium sulfate, filtered and concentrated in vacuo to give 2.3 g of 3-(S)-benzyl-piperazine-2,5-dione as an orange solid. ES MS (+) m/z 205

2-(S)-Benzylpiperazine

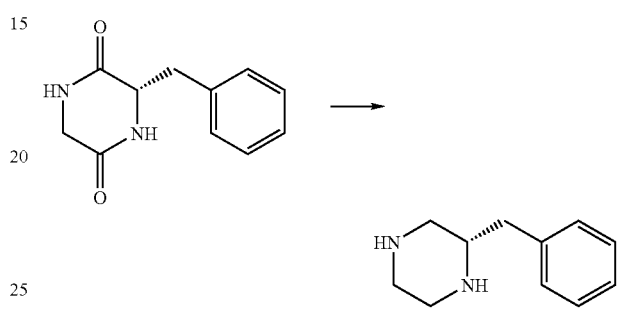

2.3 g of 3-(S)-benzyl-piperazine-2,5-dione were suspended in anhydrous THF under nitrogen and cooled in an ice-bath. 4 equiv. of lithium aluminium hydride were added. The reaction was stirred at 0° C. for 0.5 h, then heated to reflux overnight. The reaction was quenched by the subsequent addition of 1 mL/gLiAlH$_4$ of water, 1 mL/gLiAlH$_4$ of 5% aqueous sodium hydroxide solution and 3 mL/gLiAlH$_4$ of water. The resulting solid were separated by filtration through Celite and rinsed with ethyl acetate. The filtrate was concentrated in vacuo to afford 1.6 g of 2-(S)-benzylpiperazine as yellow oil. ES MS (+) m/z 177

3-(S)-benzyl-1-(4-bromo-benzyl)-piperazine

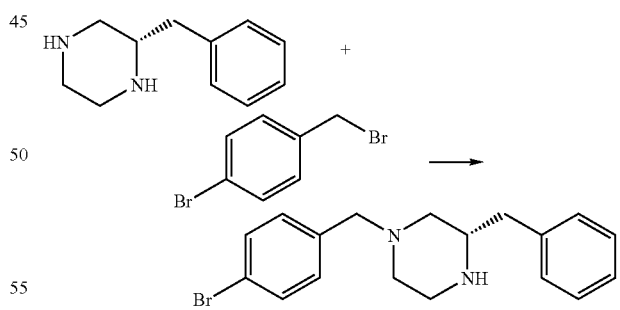

0.7 g of 2-(S) benzylpiperazine were dissolved in acetonitrile and cooled to 0° C. A solution of 0.5 quiv. 4-bromobenzylbromide in acetonitrile was added dropwise over 1 h. The reaction was stirred at room temperature for 2 h. The reaction mixture was concentrated and the residue was purified by column chromatography (silica, eluent dichloromethane, 0-5% methanol, 0-0.5% dimethylethylamine) to afford 0.6 g of 3-(S)-benzyl-1-(4-bromo-benzyl)-piperazine. ES MS (+) m/z 346.

3-(S)-benzyl-1-(2'-trifluoromethyl-biphenyl-4-ylm-ethyl)-piperazine

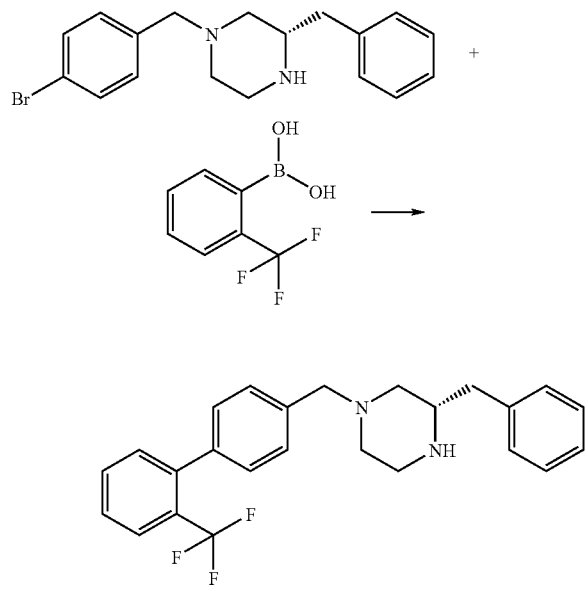

0.13 g of 3-(S)-benzyl-1-(4-bromo-benzyl)-piperazine were combined with 1.5 equiv. of 2-trifluoromethylphenyl boronic acid, 0.05 equiv. of tetrakis(triphenylphosphine)palladium(0), 2M aqueous sodium carbonate solution, toluene and ethanol. The reaction mixture was heated in a sealed tube at 120° C. overnight. The reaction mixture was filtered through Celite and concentrated in vacuo. The residue was diluted with water and extracted with ethyl acetate. The combined organic phases were washed with brine, dried over sodium sulfate, filtered and concentrated in vacuo. The crude material was purified by flash chromatography to afford 0.18 g of the title compound. ES MS (+) m/z 411.

Example 106

(R) 3-Benzyl-1-(2'-trifluoromethyl-biphenyl-4-ylm-ethyl)-piperazine

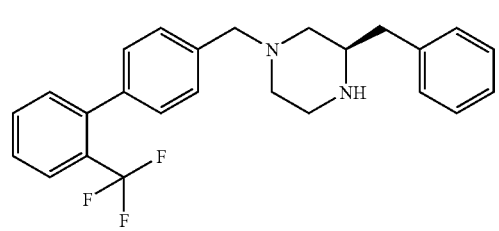

The above compound was made in the same manner as example 105, but with N-tert-butoxycarbonyl (D)-phenylalanine as the appropriate starting reagent. Yield (for Suzuki coupling): 68%; ES MS(+) m/z 411

Example 107

(S) 3-Benzyl-1-(2'-trifluoromethyl-biphenyl-4-ylm-ethyl)-piperazine

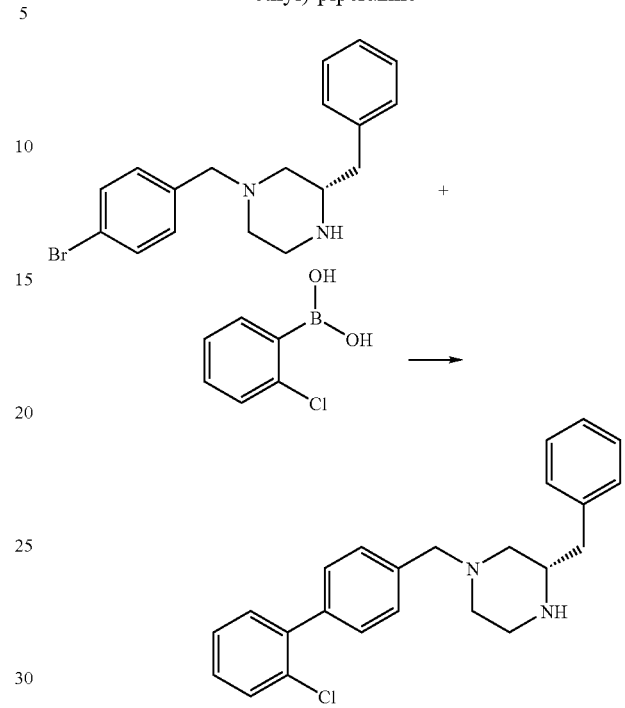

1 g of 3-(S)-benzyl-1-(4-bromo-benzyl)-piperazine were combined with 1.5 equiv. of 2-chlorophenyl boronic acid, 0.05 equiv. of tetrakis(triphenylphosphine)palladium(0), 6 equiv. of 2M aqueous sodium carbonate solution, toluene and ethanol. The reaction mixture was heated at 85° C. under nitrogen overnight. The reaction mixture was concentrated in vacuo. The residue was diluted with water and extracted with ethyl acetate. The combined organic phases were washed with brine, dried over sodium sulfate, filtered and concentrated in vacuo. The crude material was purified by flash chromatography to afford 0.98 g of the title compound. Yield 91% ES MS (+) m/z 377.

Example 108

(R) 3-Benzyl-1-(2'-trifluoromethyl-biphenyl-4-ylm-ethyl)-piperazine

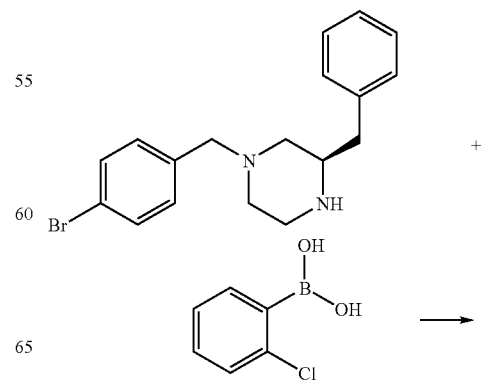

-continued

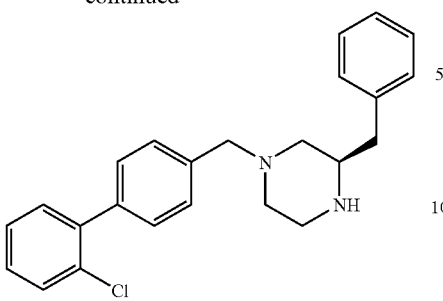

0.28 g of 3-(S)-benzyl-1-(4-bromo-benzyl)-piperazine were combined with 1.5 equiv. of 2-chlorophenyl boronic acid, 0.05 equiv. of tetrakis(triphenylphosphine)palladium (0), 6 equiv. of 2M aqueous sodium carbonate solution, toluene and ethanol. The reaction mixture was heated at 85° C. under nitrogen overnight. The reaction mixture was concentrated in vacuo. The residue was diluted with water and extracted with ethyl acetate. The combined organic phases were washed with brine, dried over sodium sulfate, filtered and concentrated in vacuo. The crude material was purified by flash chromatography to afford 0.26 g of the title compound. Yield 84% ES MS (+) m/z 377.

Example 109

(S) 3-Benzyl-1-(2'-chloro-5'-methyl-biphenyl-4-ylmethyl)-piperazine

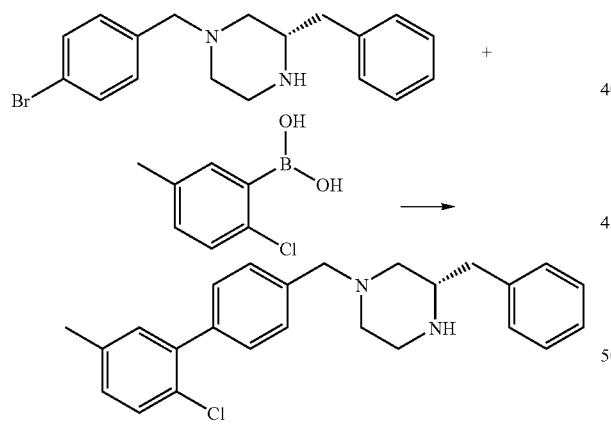

1 g of 3-(S)-benzyl-1-(4-bromo-benzyl)-piperazine were combined with 1.5 equiv. of 2-chloro-5-methylphenyl boronic acid, 0.05 equiv. of tetrakis(triphenylphosphine)palladium(0), 6 equiv. of 2M aqueous sodium carbonate solution, toluene and ethanol. The reaction mixture was heated at 85° C. under nitrogen overnight. The reaction mixture was concentrated in vacuo. The residue was diluted with water and extracted with ethyl acetate. The combined organic phases were washed with brine, dried over sodium sulfate, filtered and concentrated in vacuo. The crude material was purified by flash chromatography to afford 1.1 g of the title compound. Yield 99% ES MS (+) m/z 391.

Example 110

(R) 3-Benzyl-1-(2'-chloro-5'-methyl-biphenyl-4-ylmethyl)-piperazine

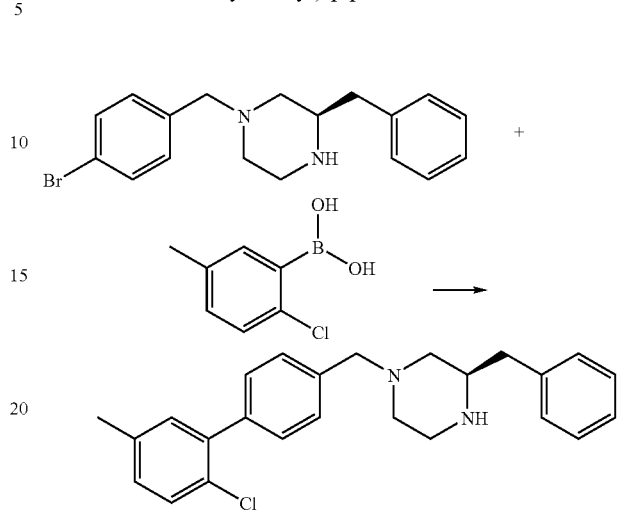

This compound could be made in the same manner as example 109, but with 3-(R)-benzyl-1-(4-bromo-benzyl)-piperazine as the corresponding starting material.

Example 111

(S) 3-Benzyl-1-(5'-chloro-2'-methyl-biphenyl-4-ylmethyl)-piperazine

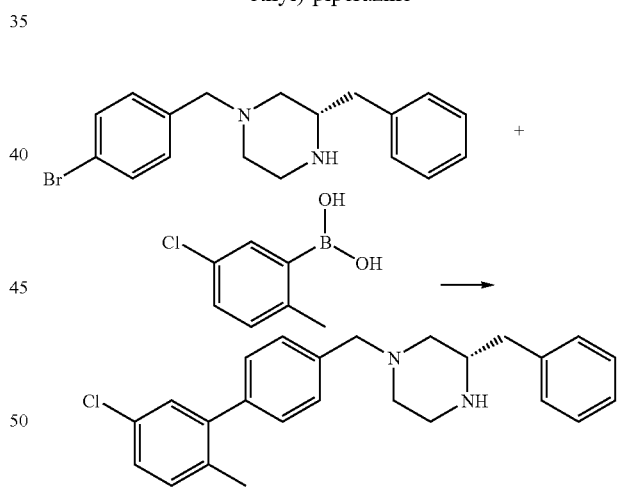

0.1 g of 3-(S)-benzyl-1-(4-bromo-benzyl)-piperazine were combined with 1.5 equiv. of 5-chloro-2-methylphenyl boronic acid, 0.05 equiv. of tetrakis(triphenylphosphine)palladium(0), 6 equiv. of 2M aqueous sodium carbonate solution, toluene and ethanol. The reaction mixture was heated at 85° C. under nitrogen overnight. The reaction mixture was concentrated in vacuo. The residue was diluted with water and extracted with ethyl acetate. The combined organic phases were washed with brine, dried over sodium sulfate, filtered and concentrated in vacuo. The crude material was purified by flash chromatography to afford 0.077 g of the title compound. Yield 68% ES MS (+) m/z 391.

Example 112

(R) 3-Benzyl-1-(2'-chloro-5'-methyl-biphenyl-4-ylmethyl)-piperazine

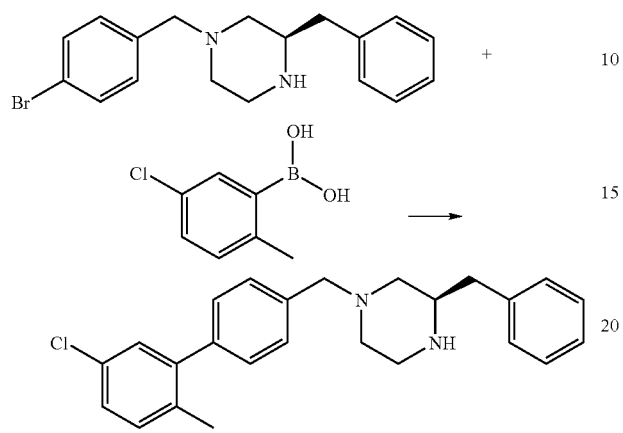

This compound could be made in the same manner as example 111, but with 3-(R)-benzyl-1-(4-bromo-benzyl)-piperazine as the corresponding starting material.

Example 113

(S)-3-Benzyl-1-(2',5'-dimethyl-biphenyl-4-ylmethyl)-piperazine

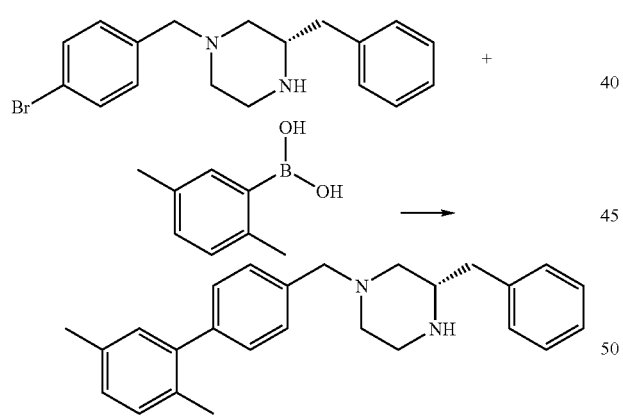

0.1 g of 3-(S)-benzyl-1-(4-bromo-benzyl)-piperazine were combined with 1.5 equiv. of 2,5-dimethylphenyl boronic acid, 0.05 equiv. of tetrakis(triphenylphosphine)palladium (0), 6 equiv. of 2M aqueous sodium carbonate solution, toluene and ethanol. The reaction mixture was heated at 85° C. under nitrogen overnight. The reaction mixture was concentrated in vacuo. The residue was diluted with water and extracted with ethyl acetate. The combined organic phases were washed with brine, dried over sodium sulfate, filtered and concentrated in vacuo. The crude material was purified by flash chromatography to afford 0.04 g of the title compound. Yield 37% ES MS (+) m/z 371.

Example 114

(R) 3-Benzyl-1-(2',5'-dimethyl-biphenyl-4-ylmethyl)-piperazine

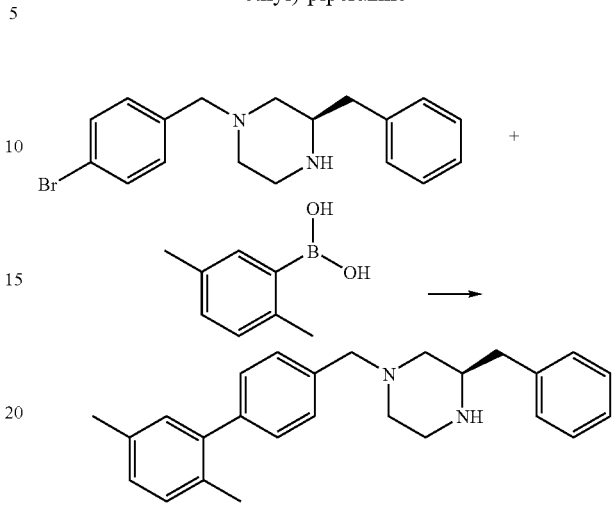

This compound could be made in the same manner as example 113, but with 3-(R)-benzyl-1-(4-bromo-benzyl)-piperazine as the corresponding starting material.

Example 115

(S) 3-Benzyl-1-(2',5'-dichloro-biphenyl-4-ylmethyl)-piperazine

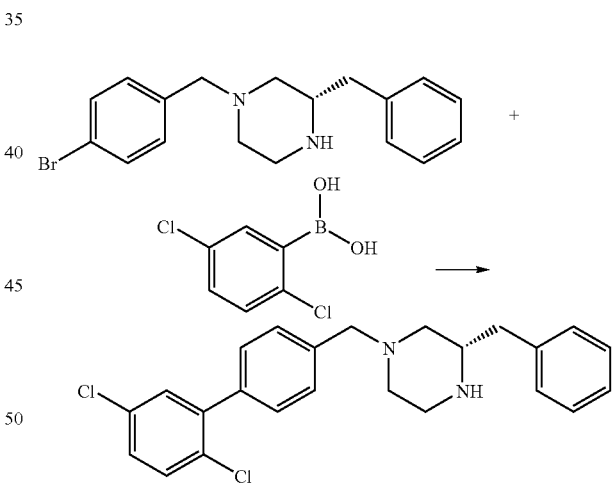

0.1 g of 3-(S)-benzyl-1-(4-bromo-benzyl)-piperazine were combined with 1.5 equiv. of 2,5-dichlorophenyl boronic acid, 0.05 equiv. of tetrakis(triphenylphosphine)palladium(0), 6 equiv. of 2M aqueous sodium carbonate solution, toluene and ethanol. The reaction mixture was heated at 85° C. under nitrogen overnight. The reaction mixture was concentrated in vacuo. The residue was diluted with water and extracted with ethyl acetate. The combined organic phases were washed with brine, dried over sodium sulfate, filtered and concentrated in vacuo. The crude material was purified by flash chromatography to afford 0.07 g of the title compound. Yield 59% ES MS (+) m/z 411.

Example 116

(R) 3-Benzyl-1-(2',5'-dichloro-biphenyl-4-ylmethyl)-piperazine

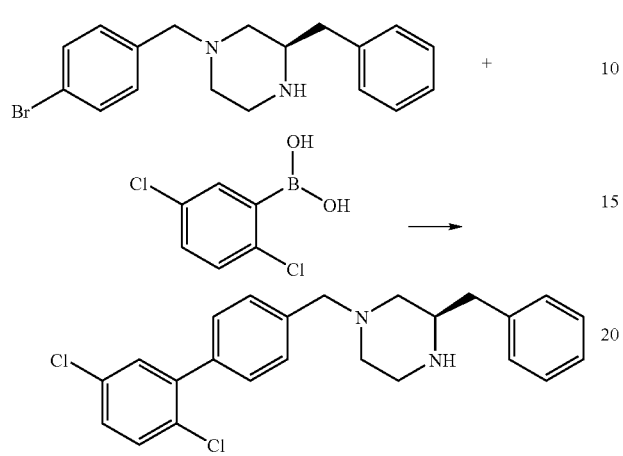

This compound could be made in the same manner as example 115, but with 3-(R)-benzyl-1-(4-bromo-benzyl)-piperazine as the corresponding starting material.

Example 117

1-Methyl-2-benzyl-4-(2'-trifluoromethyl-biphenyl-4-ylmethyl)-piperazine

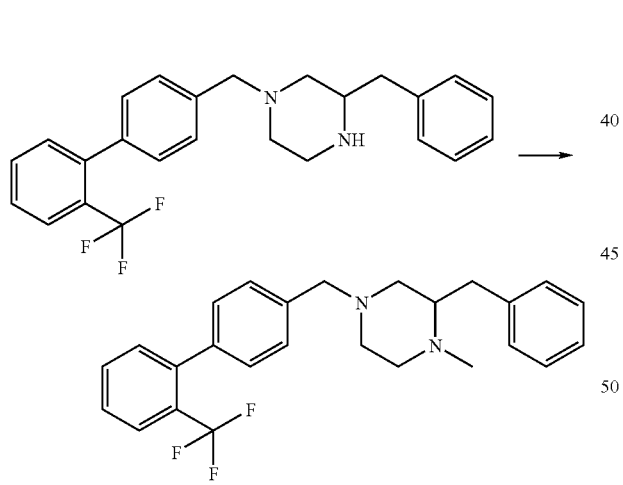

This compound could be made the following manner: 100 mg of 3-benzyl-1-(2'-trifluoromethyl-biphenyl-4-ylmethyl)-piperazine would be dissolved in acetonitrile, 3 equiv. of N,N-diisopropylethylamine would be added followed by 1.1 equiv. of iodomethane. The reaction would be stirred at 80° C. overnight. The reaction would be diluted with dichloromethane and washed with 1N aqueous NaOH solution. The organic layer would be dried over Na2SO4, filtered and concentrated in vacuo. The crude residue would be purified by column chromatography to afford 1-methyl-2-phenyl-4-(2'-trifluoromethyl-biphenyl-4-ylmethyl)-piperazine.

Example 118

1-Ethyl-2-benzyl-4-(2'-trifluoromethyl-biphenyl-4-ylmethyl)-piperazine

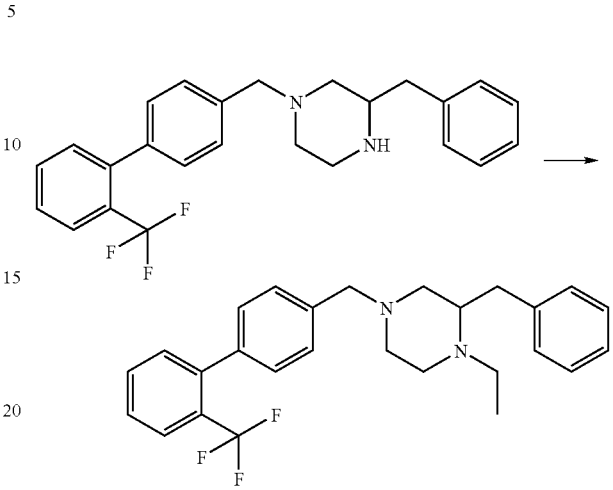

The above compound could be made in the same manner as example 117, but with bromoethane as the appropriate alkylating reagent.

Example 119

1-Isopropyl-2-benzyl-4-(2'-trifluoromethyl-biphenyl-4-ylmethyl)-piperazine

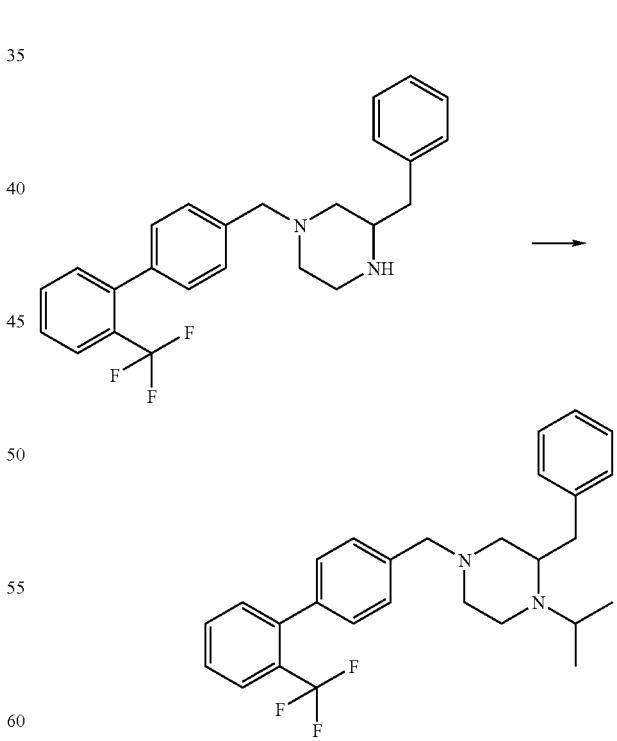

This compound could be made in the following manner: 100 mg of 3-phenyl-1-(2'-trifluoromethyl-biphenyl-4-ylmethyl)-piperazine would be dissolved in a 2:1 mixture of dichloroethane and acetone, 2 equiv. of sodium triacetoxyborohydride would be added followed by 30 μL of acetic acid.

The reaction would be stirred at room temperature under nitrogen overnight. The reaction would be diluted with 5 mL of dichloromethane. The reaction mixture would be washed with 1M aqueous sodium hydroxide solution and brine, then dried over sodium sulfate, filtered and concentrated in vacuo. The crude residue would be purified by column chromatography to afford the title compound.

Example 120

1-Cyclohexyl-2-benzyl-4-(2'-trifluoromethyl-biphenyl-4-ylmethyl)-piperazine

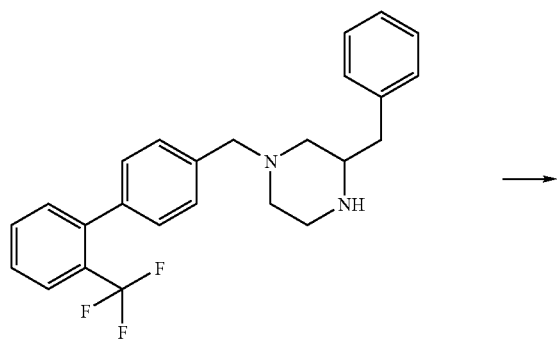

The above compound could be made in the same manner as example 117, but with cyclohexylbromide as the appropriate alkylating reagent.

Example 121

1-[2-(S)-Benzyl-4-(2'-trifluoromethyl-biphenyl-4-ylmethyl)-piperazin-1-yl]-ethanone

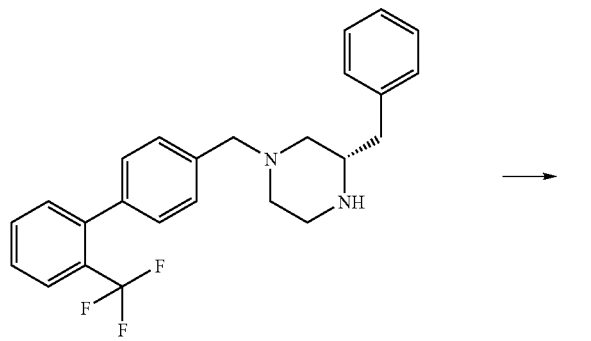

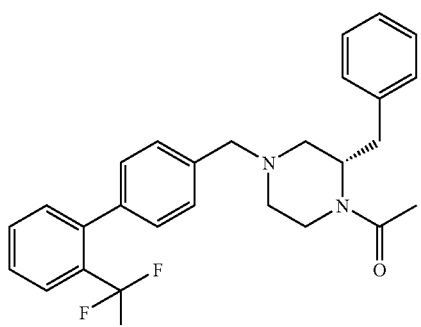

45 mg of 3-(S)-benzyl-1-(2'-trifluoromethyl-biphenyl-4-ylmethyl)-piperazine was dissolved in dichloromethane, 1.1 equiv. of acetylchloride and 1.5 equiv. of N,N-diisopropylethylamine were added. The reaction was stirred at room temperature under nitrogen overnight. The reaction was diluted with DCM, washed with saturated aqueous sodium bicarbonate solution, then dried over sodium sulfate, filtered and concentrated in vacuo. The crude residue was purified by column chromatography to afford 51 mg of the title compound as free base. Yield 84%, Treatment with 1 equiv. of 1M HCl in dioxane gave the HCl salt. ES MS(+) m/z 453

Example 122

1-[2-(R)-Benzyl-4-(2'-trifluoromethyl-biphenyl-4-ylmethyl)-piperazin-1-yl]-ethanone

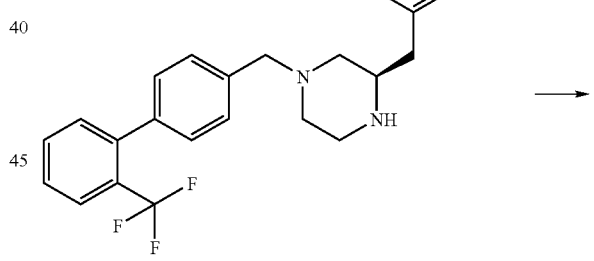

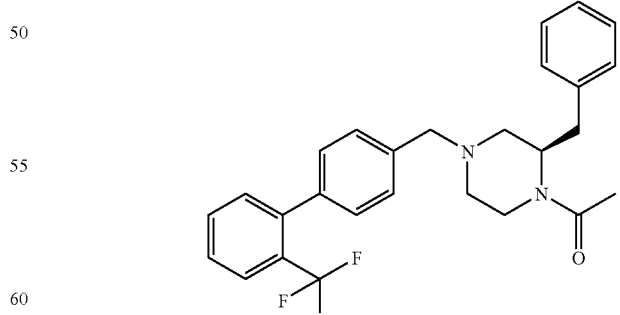

The HCl salt of the above compound was made in the same manner as example 121, but with 3-(R)-benzyl-1-(2'-trifluoromethyl-biphenyl-4-ylmethyl)-piperazine as the appropriate starting material. Yield 61%, ES MS(+) m/z 453

Example 123

Phenyl-[2-(S)-benzyl-4-(2'-trifluoromethyl-biphenyl-4-ylmethyl)-piperazin-1-yl]-methanone

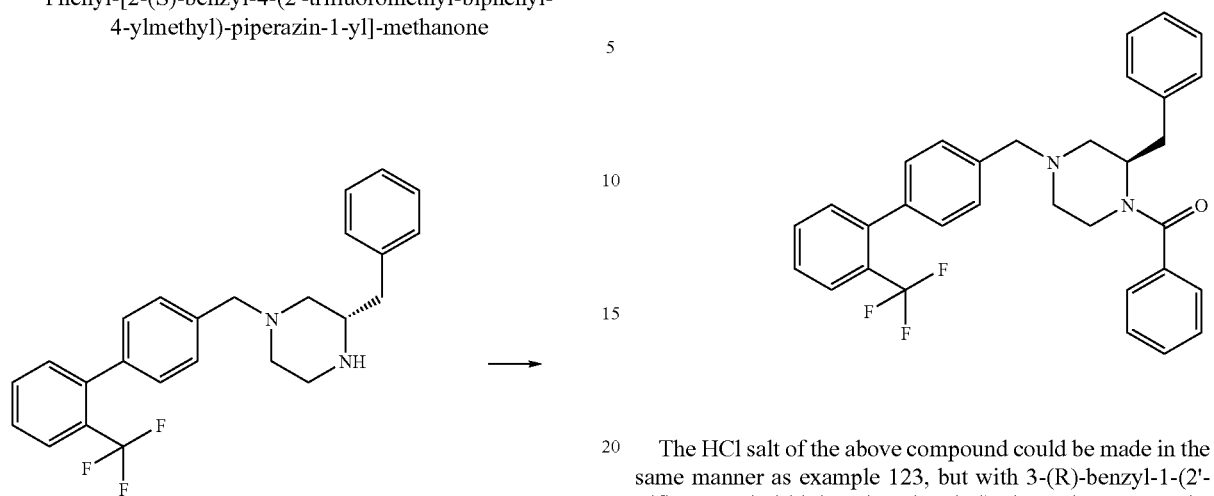

The HCl salt of the above compound was made in the same manner as example 121, but with benzoylchloride as the appropriate acidchloride. Yield 65%, ES MS(+) m/z 515

Example 124

Phenyl-[2-(R)-benzyl-4-(2'-trifluoromethyl-biphenyl-4-ylmethyl)-piperazin-1-yl]-methanone

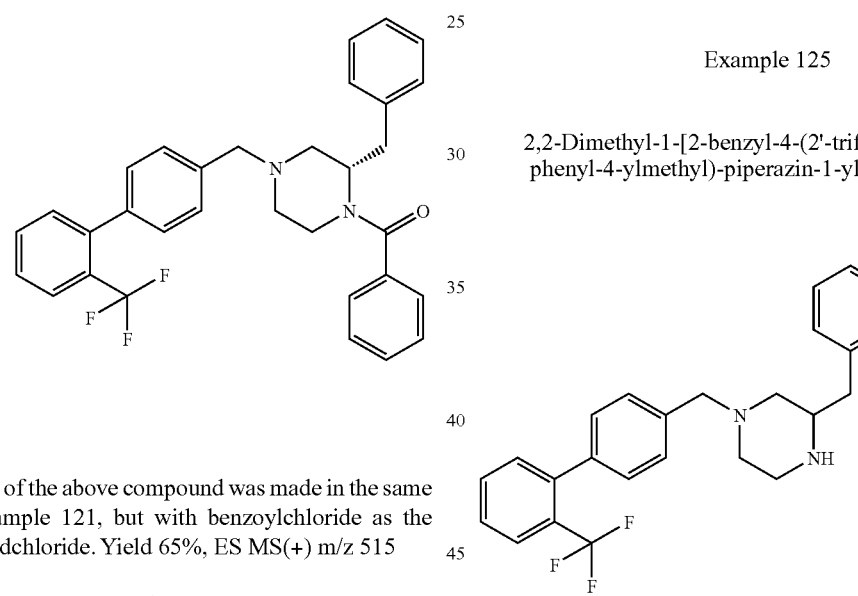

The HCl salt of the above compound could be made in the same manner as example 123, but with 3-(R)-benzyl-1-(2'-trifluoromethyl-biphenyl-4-ylmethyl)-piperazine as the appropriate starting material

Example 125

2,2-Dimethyl-1-[2-benzyl-4-(2'-trifluoromethyl-biphenyl-4-ylmethyl)-piperazin-1-yl]-propan-1-one

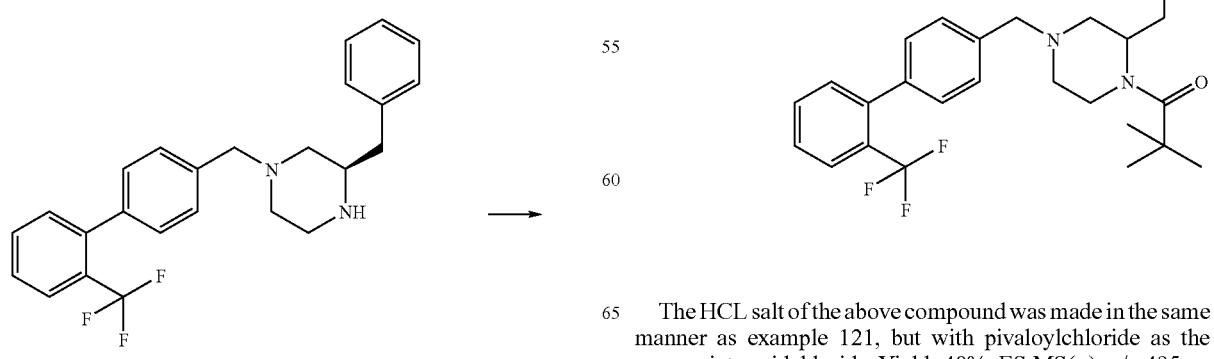

The HCL salt of the above compound was made in the same manner as example 121, but with pivaloylchloride as the appropriate acidchloride. Yield: 40%, ES MS(+) m/z 495

Example 126

2-Phenyl-1-[2-(S)-benzyl-4-(2'-trifluoromethyl-bi-
phenyl-4-ylmethyl)-piperazin-1-yl]-ethanone

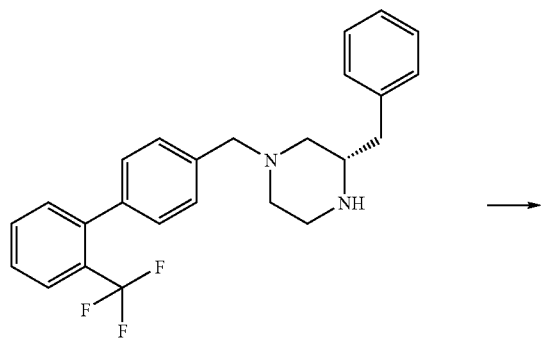

→

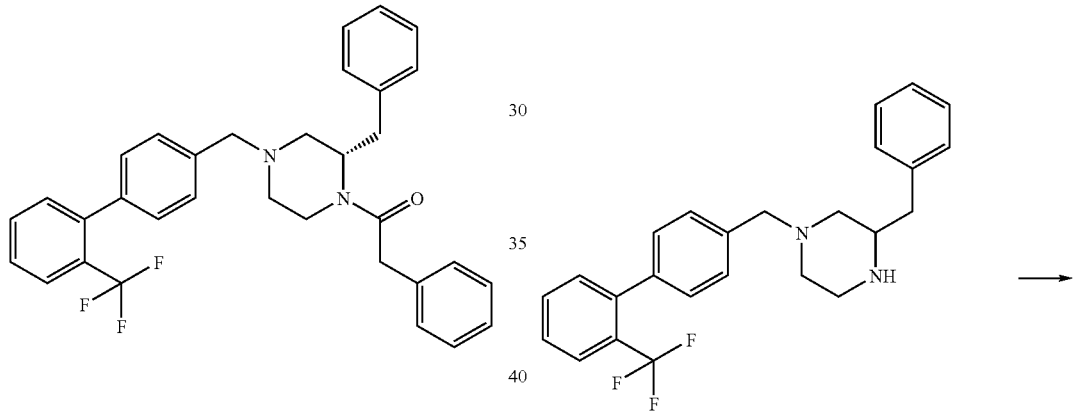

The HCl salt of the above compound could be made in the same manner as example 121, but with phenylacetyl chloride as the appropriate acidchloride.

Example 127

2-Phenyl-1-[2-(R)-benzyl-4-(2'-trifluoromethyl-bi-
phenyl-4-ylmethyl)-piperazin-1-yl]-ethanone

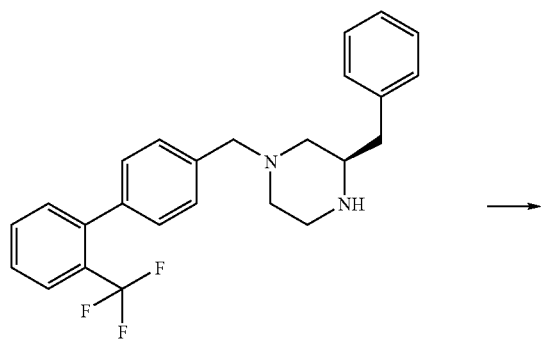

→

-continued

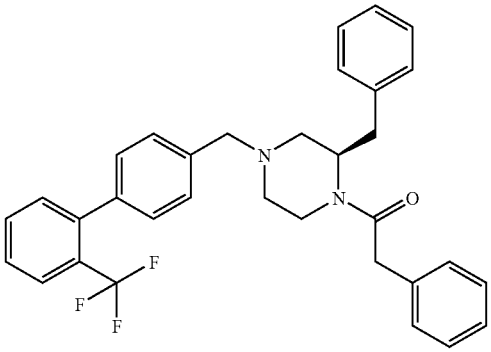

The HCl salt of the above compound was made in the same manner as example 126, but with 3-(R)-benzyl-1-(2'-trifluoromethyl-biphenyl-4-ylmethyl)-piperazine as the appropriate starting material. Yield: 63%, ES MS(+) m/z 529

Example 128

2-Benzyl-4-(2'-trifluoromethyl-biphenyl-4-ylm-
ethyl)-piperazine-1-carboxylic acid methylamide

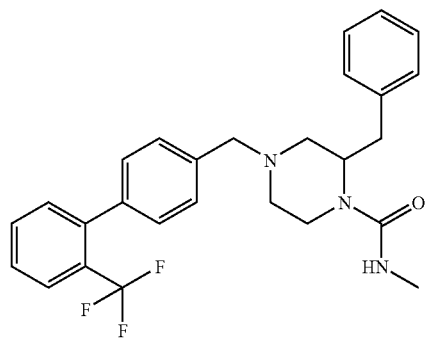

This compound could be made in the following manner: 100 mg of 3-benzyl-1-(2'-trifluoromethyl-biphenyl-4-ylmethyl)-piperazine would be dissolved in dichloromethane, 1.1 equiv. methylisocyanate would be added. The reaction would be shaken at room temperature overnight. The reaction would be concentrated in vacuo. The residue would be diluted with DCM, washed with 1M aqueous sodium hydroxide solution, then dried over sodium sulfate, filtered and concentrated in vacuo. The crude residue would be purified by column chromatography to afford the title compound as free base. Addition of 1 equiv. of 1M HCl in dioxane and concentratation in vacuo would afford the title compound as hydrochloride salt.

Example 129

2-Benzyl-4-(2'-trifluoromethyl-biphenyl-4-ylmethyl)-piperazine-1-carboxylic acid dimethylamide

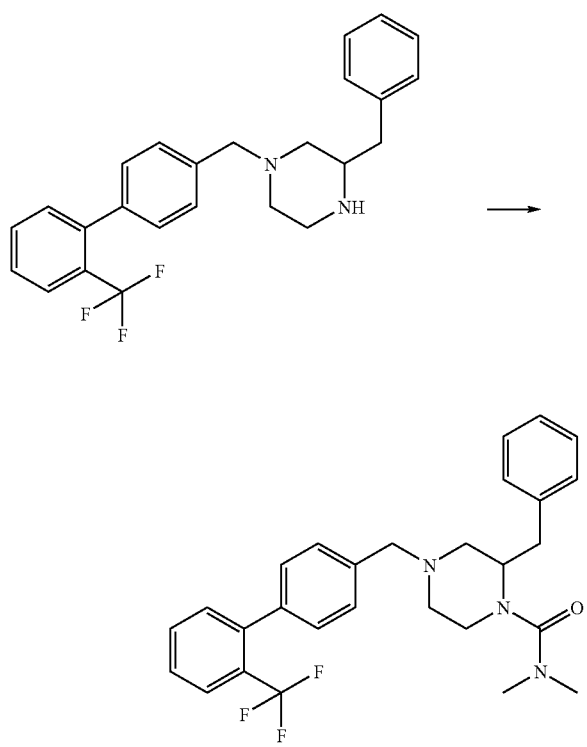

The above compound could be made in the same manner as example 121, but with N,N-dimethylcarbamoyl chloride as the appropriate acidchloride.

Example 130

2-Benzyl-4-(2'-trifluoromethyl-biphenyl-4-ylmethyl)-piperazine-1-carboxylic acid phenylamide

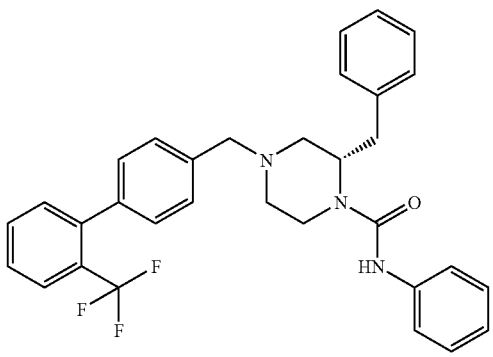

The above compound was made in the following manner: 100 mg of 3-benzyl-1-(2'-trifluoromethyl-biphenyl-4-ylmethyl)-piperazine dissolved in dichloromethane, 1.1 equiv. methylisocyanate added. The reaction was shaken at room temperature overnight. The reaction was concentrated in vacuo. The residue was diluted with DCM, washed with 1M aqueous sodium hydroxide solution, then dried over sodium sulfate, filtered and concentrated in vacuo. The crude product was identified by ES MS(+) (m/z 530).

Example 131

1-Methanesulfonyl-2-benzyl-4-(2'-trifluoromethyl-biphenyl-4-ylmethyl)-piperazine

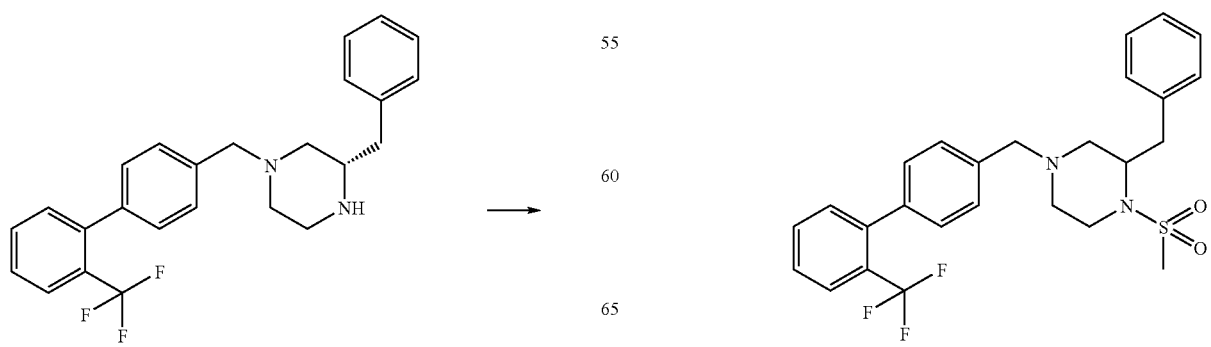

The above compound was made in the same manner as example 121, but with methanesulfonyl chloride as the appropriate acidchloride. The crude product was identified by ES MS(+) (m/z 489).

Example 132

1-Benzenesulfonyl-2-phenyl-4-(2'-trifluoromethyl-biphenyl-4-ylmethyl)-piperazine

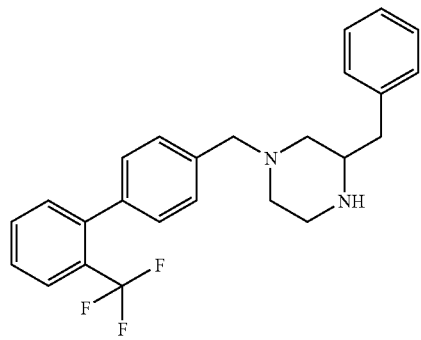

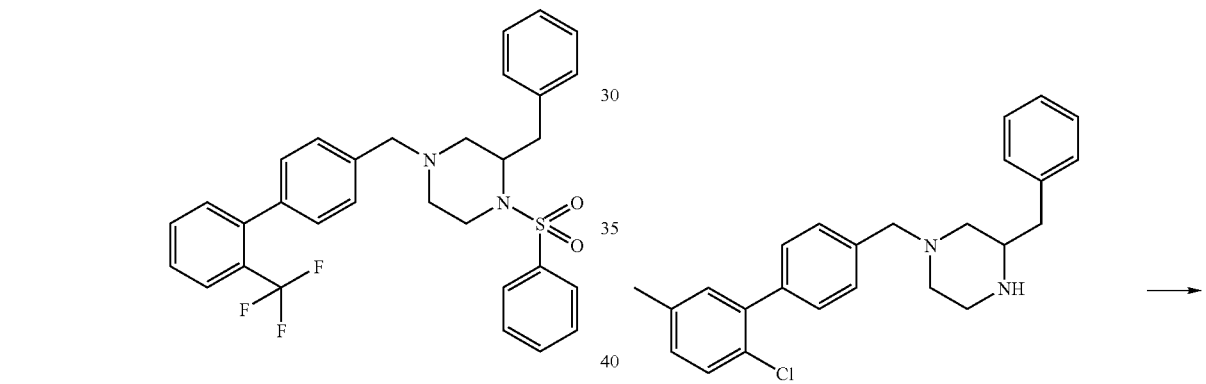

The above compound was made in the same manner as example 121, but with benzenesulfonyl chloride as the appropriate acidchloride. The crude product was identified by ES MS(+) (m/z 551).

Example 133

1-Cyclohexanesulfonyl-2-phenyl-4-(2'-trifluoromethyl-biphenyl-4-ylmethyl)-piperazine

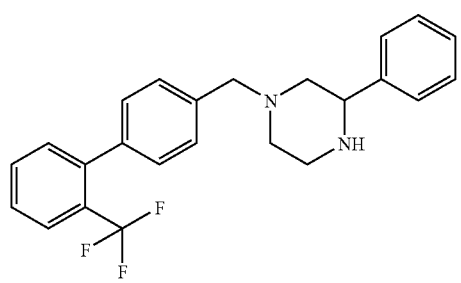

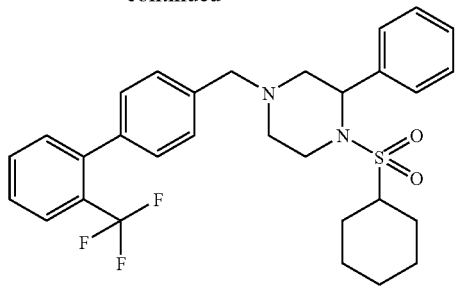

The above compound could be made in the same manner as example 121, but with of cyclohexanesulfonyl chloride as the appropriate acidchloride.

Example 134

1-Methyl-2-benzyl-4-(2'-chloro-5'-methyl-biphenyl-4-ylmethyl)-piperazine

This compound could be made the following manner: 100 mg of 3-benzyl-1-(2'-chloro-5'-methyl-biphenyl-4-ylmethyl)-piperazine would be dissolved in acetonitrile, 3 equiv. of N,N-diisopropylethylamine would be added followed by 1.1 equiv. of iodomethane. The reaction would be stirred at 80° C. overnight. The reaction would be diluted with dichloromethane and washed with 1N aqueous NaOH solution. The organic layer would be dried over $Na_2SO_4$, filtered and concentrated in vacuo. The crude residue would be purified by column chromatography to afford 1-methyl-2-phenyl-4-(2'-chloro-5'-methyl-biphenyl-4-ylmethyl)-piperazine.

Example 135

1-Ethyl-2-(S)-benzyl-4-(2'-chloro-5'-methyl-biphenyl-4-ylmethyl)-piperazine

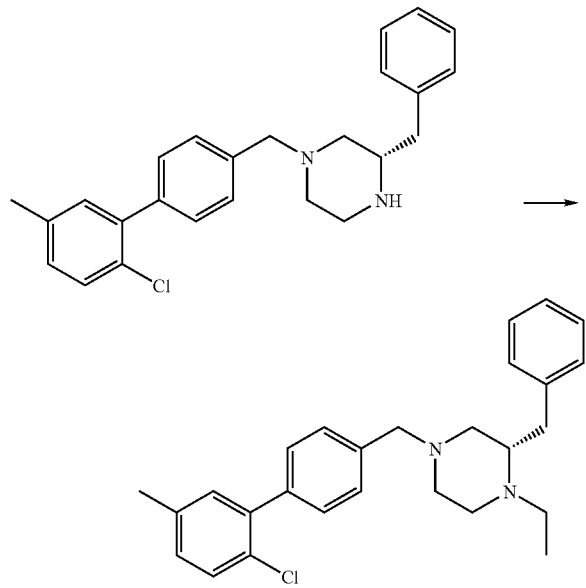

This compound was made in the following manner: 50 mg of 3-(S)-benzyl-1-(2'-chloro-5'-methyl-biphenyl-4-ylmethyl)-piperazine was dissolved in THF, 2 equ. of bromoethane and 2 equ. of N,N-diisopropylethylamine were added. The reaction was stirred at room temperature overnight. The reaction mixture was concentrated under reduced pressure. The residue was diluted with DCM, washed with saturated aqueous sodium bicarbonate solution, then dried over sodium sulfate, filtered and concentrated in vacuo. The crude residue was purified by column chromatography to afford the title compound as the free base. Treatment with 1 equ. 1M HCl in dioxane and concentration in vacuo afforded 29.5 mg of the corresponding hydrochloride salt. Yield 51%, ES MS m/z 419/421.

Example 136

1-Isopropyl-2-benzyl-4-(2'-chloro-5'-methyl-biphenyl-4-ylmethyl)-piperazine

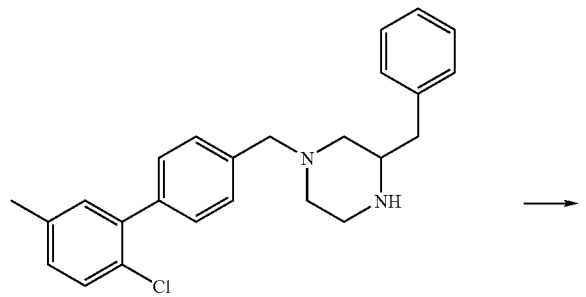

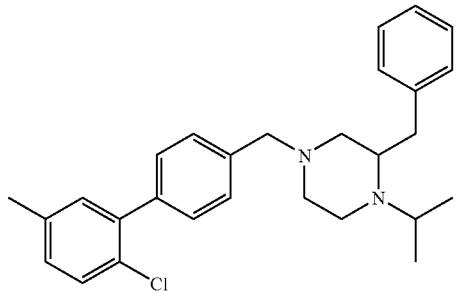

This compound could be made the following manner: 100 mg of 3-phenyl-1-(2'-chloro-5'-methyl-biphenyl-4-ylmethyl)-piperazine would be dissolved in a 2:1 mixture of dichloroethane and acetone, 2 equiv. of sodium triacetoxyborohydride would be added followed by 30 µL of acetic acid. The reaction would be stirred at room temperature under nitrogen overnight. The reaction would be diluted with 5 mL of dichloromethane. The reaction mixture would be washed with 1M aqueous sodium hydroxide solution and brine, then dried over sodium sulfate, filtered and concentrated in vacuo. The crude residue would be purified by column chromatography to afford the title compound.

Example 137

1-Cyclohexyl-2-benzyl-4-(2'-chloro-5'-methyl-biphenyl-4-ylmethyl)-piperazine

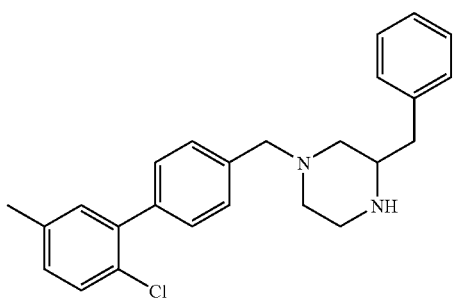

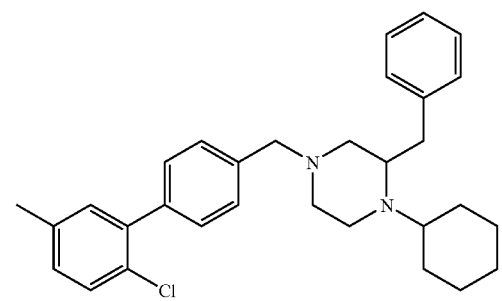

The above compound could be made in the same manner as example 134, but with cyclohexylbromide as the appropriate alkylating reagent.

Example 138

1-[2-(S)-Benzyl-4-(2'-chloro-5'-methyl-biphenyl-4-ylmethyl)-piperazin-1-yl]-ethanone

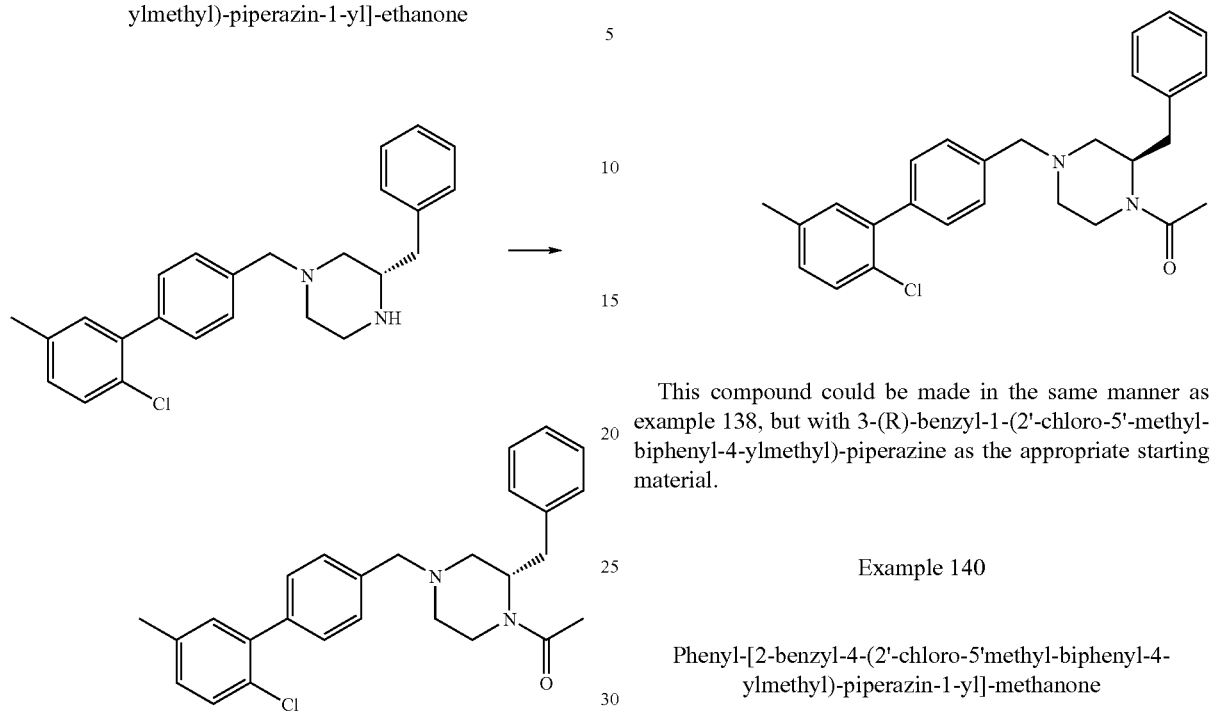

This compound was made in the following manner: 50 mg of 3-(S)-benzyl-1-(2'-chloro-5'-methyl-biphenyl-4-ylmethyl)-piperazine was dissolved in THF, 2 equiv. of acetylchloride and 2 equiv. of N,N-diisopropylethylamine were added. The reaction was stirred at room temperature overnight. The reaction was diluted with DCM, washed with saturated aqueous sodium bicarbonate solution, then dried over sodium sulfate, filtered and concentrated in vacuo. The crude residue was purified by column chromatography to afford the title compound as the free base. Treatment with 1 equiv 1M HCl in dioxane and concentration in vacuo afforded 46 mg of the corresponding hydrochloride salt. Yield 77%, ES MS m/z 433

Example 139

1-[2-(R)-Benzyl-4-(2'-chloro-5'-methyl-biphenyl-4-ylmethyl)-piperazin-1-yl]-ethanone This compound could be made in the same manner as example 138, but with 3-(R)-benzyl-1-(2'-chloro-5'-methyl-biphenyl-4-ylmethyl)-piperazine as the appropriate starting material.

Example 140

Phenyl-[2-benzyl-4-(2'-chloro-5'methyl-biphenyl-4-ylmethyl)-piperazin-1-yl]-methanone

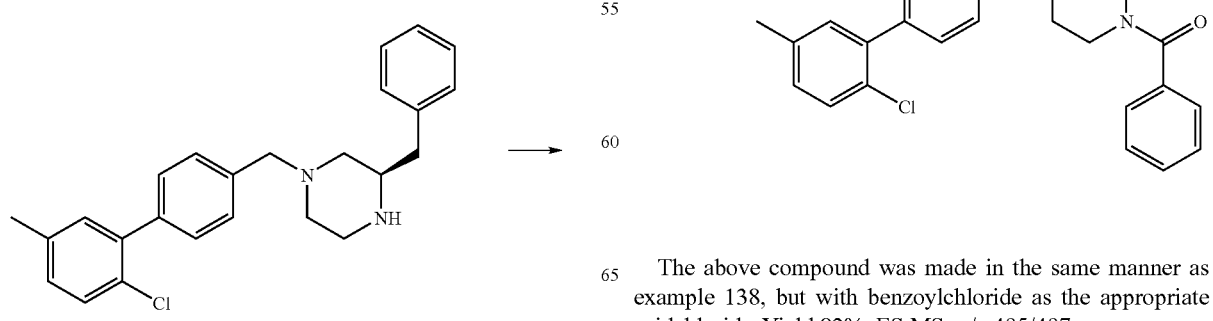

The above compound was made in the same manner as example 138, but with benzoylchloride as the appropriate acidchloride. Yield 82%, ES MS m/z 495/497

Example 141

2,2-Dimethyl-1-[2-benzyl-4-(2'-chloro-5'-methyl-biphenyl-4-ylmethyl)-piperazin-1-yl]-propan-1-one

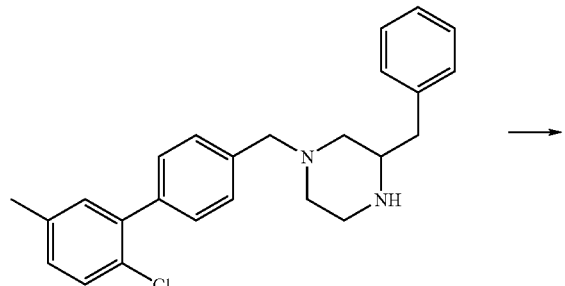

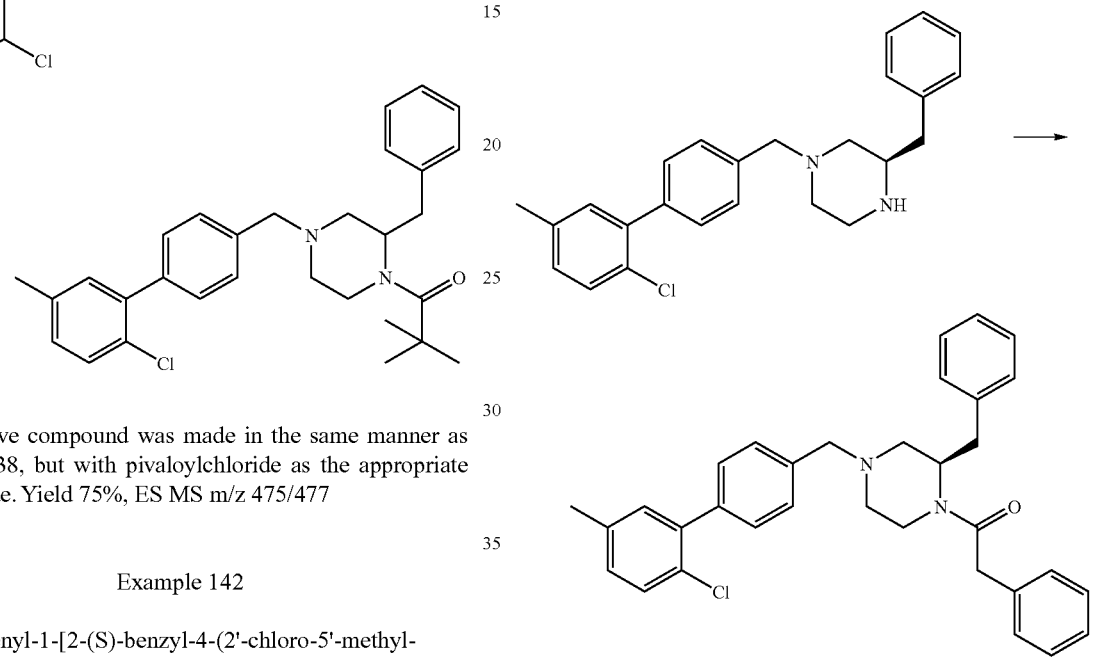

The above compound was made in the same manner as example 138, but with pivaloylchloride as the appropriate acidchloride. Yield 75%, ES MS m/z 475/477

Example 142

2-Phenyl-1-[2-(S)-benzyl-4-(2'-chloro-5'-methyl-biphenyl-4-ylmethyl)-piperazin-1-yl]-ethanone

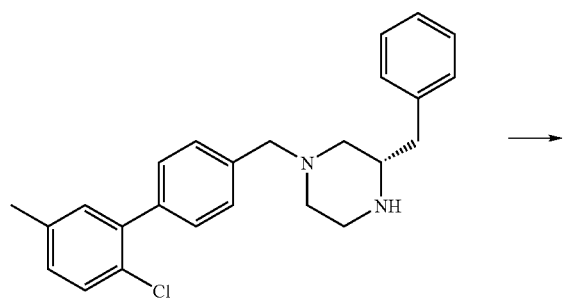

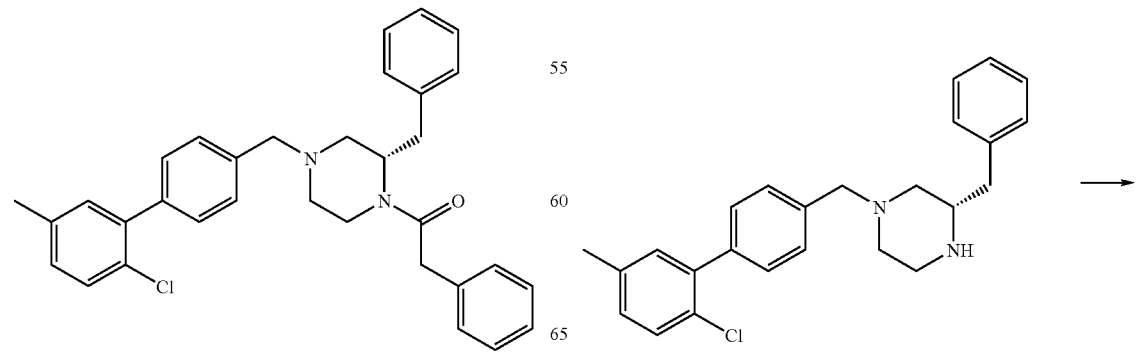

The HCl salt of the above compound was made in the same manner as example 138, but with phenylacetyl chloride as the appropriate acidchloride. Yield 62% ES MS m/z 509

Example 143

2-Phenyl-1-[2-(S)-benzyl-4-(2'-chloro-5'-methyl-biphenyl-4-ylmethyl)-piperazin-1-yl]-ethanone The HCl salt of the above compound could be made in the same manner as example 142, but with 3-(R)-benzyl-1-(2'-chloro-5'-methyl-biphenyl-4-ylmethyl)-piperazine as the appropriate starting material.

Example 144

2-(S)-Benzyl-4-(2'-chloro-5'-methyl-biphenyl-4-ylmethyl)-piperazine-1-carboxylic acid methylamide -continued

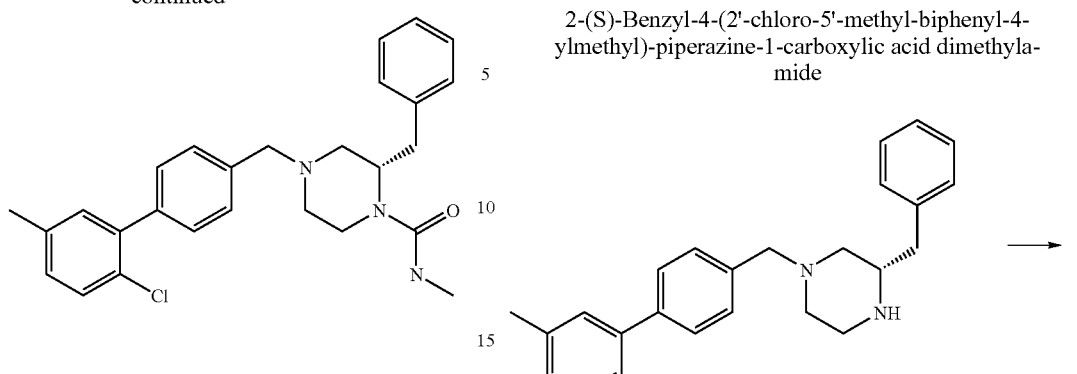

This compound was made in the following manner: 50 mg of 3-(S)-benzyl-1-(2'-chloro-5'-methyl-biphenyl-4-ylmethyl)-piperazine was dissolved in THF, 2 equiv. methylisocyanate was added. The reaction was stirred at room temperature overnight. The reaction was diluted with DCM, washed with saturated aqueous sodium bicarbonate solution, then dried over sodium sulfate, filtered and concentrated in vacuo. The crude residue was purified by column chromatography to afford the title compound as the free base. Treatment with 1 equiv 1M HCl in dioxane an concentration in vacuo afforded 52 mg of the corresponding hydrochloride salt. Yield 84%, ES MS m/z 448

Example 145

2-(R)-Benzyl-4-(2'-chloro-5'-methyl-biphenyl-4-ylmethyl)-piperazine-1-carboxylic acid methylamide

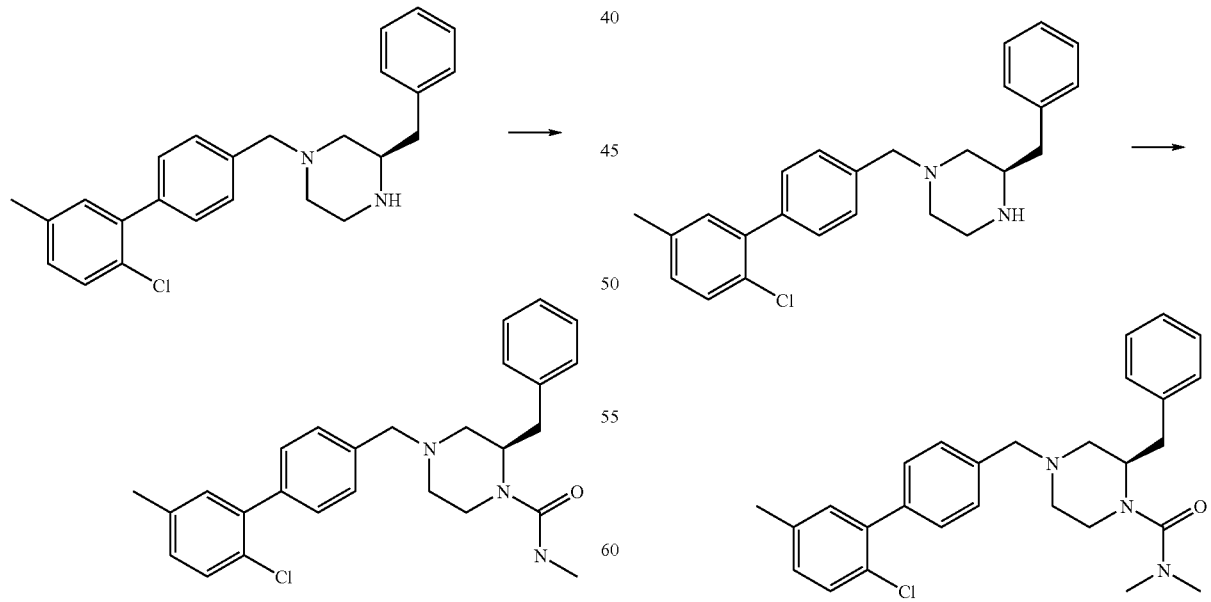

The HCl salt of the above compound could be made in the same manner as example 143, but with 3-(R)-benzyl-1-(2'-chloro-5'-methyl-biphenyl-4-ylmethyl)-piperazine as the appropriate starting material.

Example 146

2-(S)-Benzyl-4-(2'-chloro-5'-methyl-biphenyl-4-ylmethyl)-piperazine-1-carboxylic acid dimethylamide

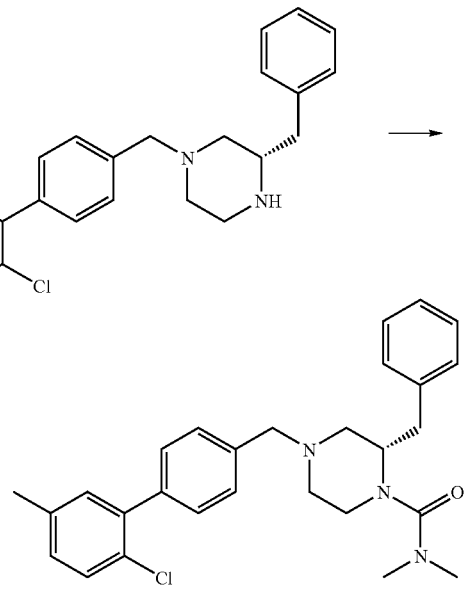

The above compound was made in the same manner as example 138, but with N,N-dimethylcarbamoyl chloride as the appropriate acidchloride. Yield 71%, ES MS m/z 462

Example 147

2-(R)-Benzyl-4-(2'-chloro-5'-methyl-biphenyl-4-ylmethyl)-piperazine-1-carboxylic acid dimethylamide

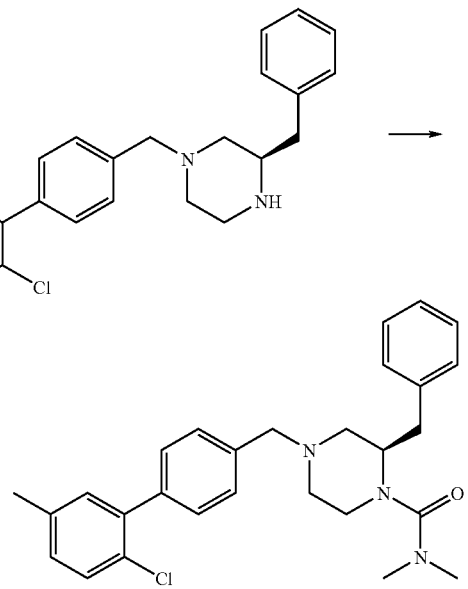

The above compound could be made in the same manner as example 138, but with 3-(R)-benzyl-1-(2'-chloro-5'-methyl-biphenyl-4-ylmethyl)-piperazine as the appropriate starting material.

Example 148

2-Benzyl-4-(2'-chloro-5'-methyl-biphenyl-4-ylmethyl)-piperazine-1-carboxylic acid phenylamide

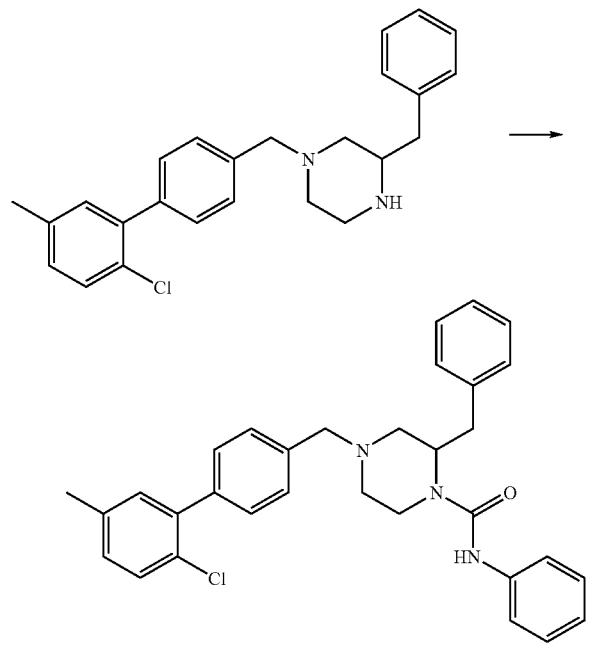

The above compound was made in the same manner as example 144, but with phenylisocyanate as the appropriate isocyanate. Yield 88%, ES MS m/z 510/512

Example 149

1-Methanesulfonyl-2-(S)-benzyl-4-(2'-chloro-5'-methyl-biphenyl-4-ylmethyl)-piperazine

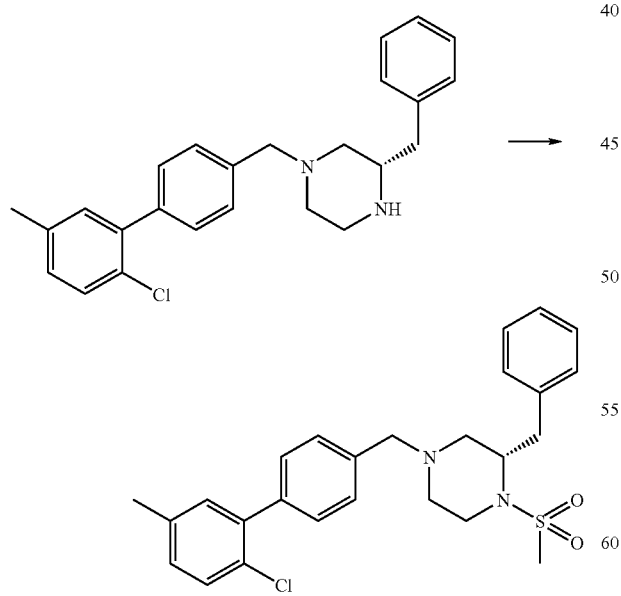

The hydrochloride salt of the above compound was made in the same manner as example 138, but with methanesulfonyl chloride as the appropriate acidchloride. Yield 67%, ES MS m/z 469

Example 150

1-Methanesulfonyl-2-(R)-benzyl-4-(2'-chloro-5'-methyl-biphenyl-4-ylmethyl)-piperazine

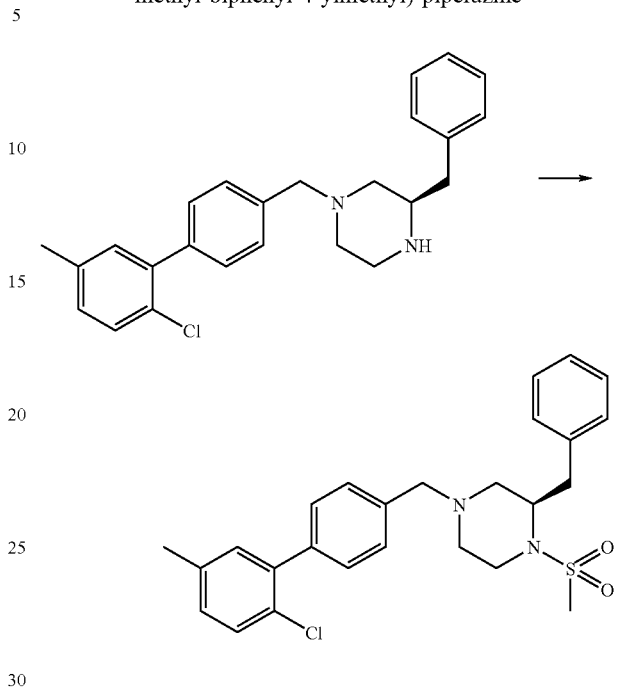

The hydrochloride salt of the above compound could be made in the same manner as example 149, but with 3-(R)-benzyl-1-(2'-chloro-5'-methyl-biphenyl-4-ylmethyl)-piperazine as the appropriate starting material.

Example 151

1-Benzenesulfonyl-2-(S)-benzyl-4-(2'-chloro-5'-methyl-biphenyl-4-ylmethyl)-piperazine

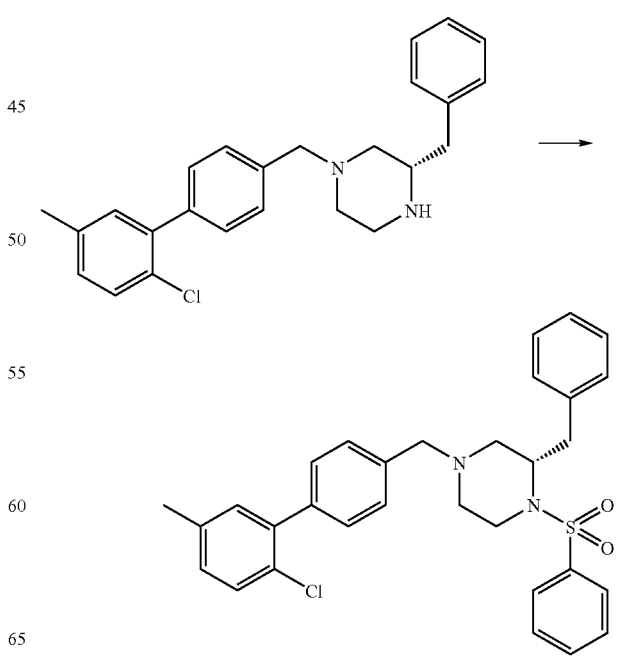

The hydrochloride salt of the above compound was made in the same manner as example 138, but with benzenesulfonyl chloride as the appropriate acidchloride. Yield 77%, ES MS m/z 531

Example 152

1-Benzenesulfonyl-2-(S)-benzyl-4-(2'-chloro-5'-methyl-biphenyl-4-ylmethyl)-piperazine

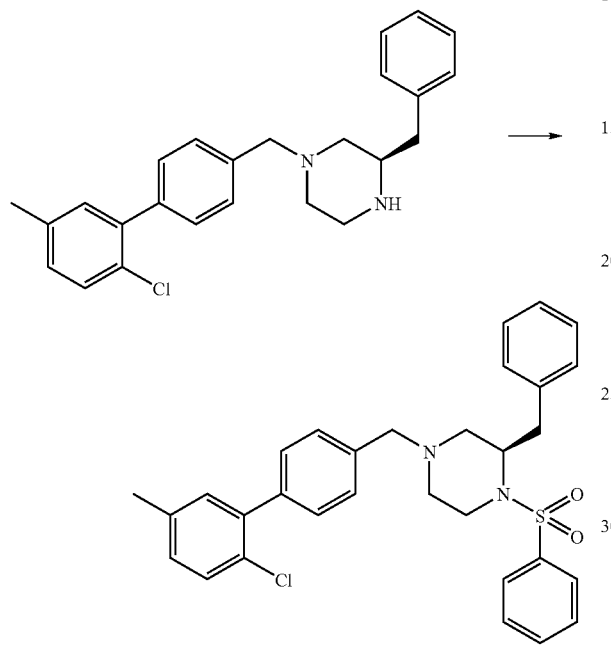

The hydrochloride salt of the above compound could be made in the same manner as example 151, but with 3-(R)-benzyl-1-(2'-chloro-5'-methyl-biphenyl-4-ylmethyl)-piperazine as the appropriate starting material.

Example 153

1-Cyclohexanesulfonyl-2-benzyl-4-(2'-chloro-5'-methyl-biphenyl-4-ylmethyl)-piperazine

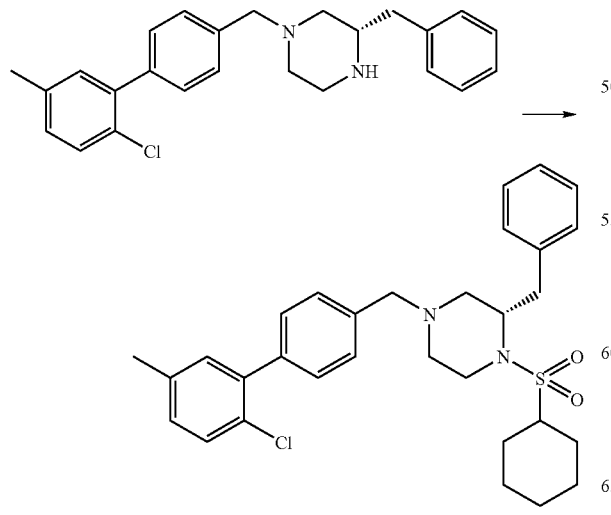

The above compound was made in the same manner as example 138, but with cyclohexanesulfonyl chloride as the appropriate acidchloride. Yield 8%, ES MS m/z 473/475

Example 154

1-[2-(S)Benzyl-4-(2'-chloro-biphenyl-4-ylmethyl)-piperazin-1-yl]-ethanone

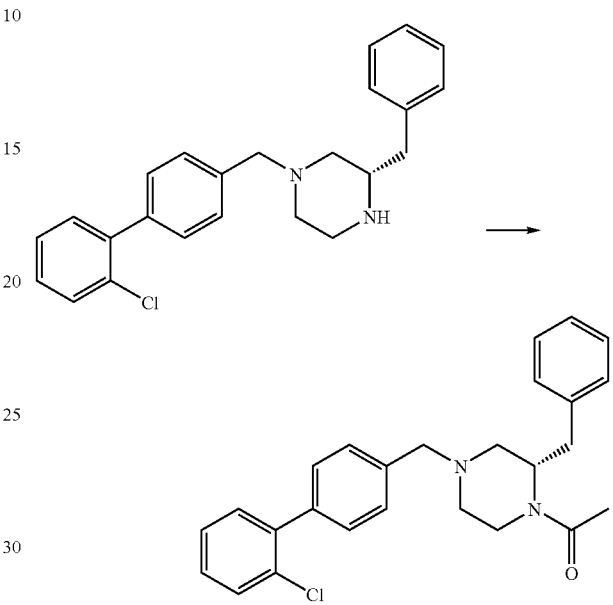

50 mg of 3-(S)-benzyl-1-(2'-chloro-5'-methyl-biphenyl-4-ylmethyl)-piperazine were dissolved in THF, 2 equiv. of acetylchloride and 2 equiv. of N,N-diisopropylethylamine were added. The reaction was stirred at room temperature under nitrogen overnight. The reaction was concentrated, the residue redissolved in DCM, washed with saturated aqueous sodium bicarbonate solution, then dried over sodium sulfate, filtered and concentrated in vacuo. The crude residue was purified by column chromatography to afford the title compound as its freebase. Treatment with 1M HCl in dioxane gave 38 mg of the title compound as its hydrochloride salt Yield: 63%, ES MS (+) m/z 419.

Example 155

1-[2-(R) Benzyl-4-(2'-chloro-biphenyl-4-ylmethyl)-piperazin-1-yl]-ethanone

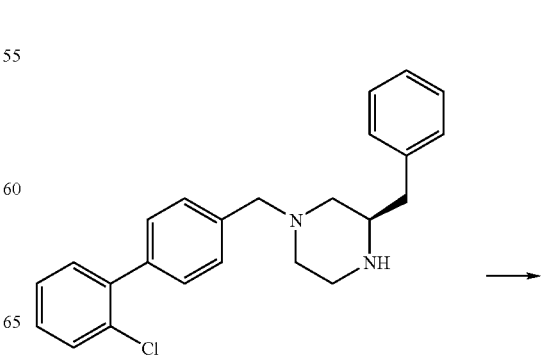

-continued

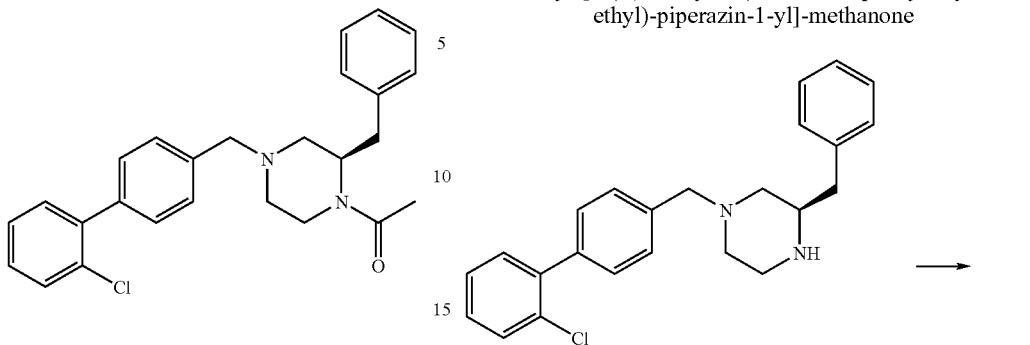

The hydrochloride salt of the above compound was made in the same manner as example 154, but with 3-(R)-benzyl-1-(2'-chloro-5'-methyl-biphenyl-4-ylmethyl)-piperazine as the appropriate starting material. Yield 39%, ES MS (+) m/z 419

Example 156

Phenyl-[2-(S)-benzyl-4-(2'-chloro-biphenyl-4-ylmethyl)-piperazin-1-yl]-methanone The hydrochloride salt of the above compound was made in the same manner as example 154, but with benzoylchloride as the appropriate acidchloride. Yield: 79%, ES MS (+) m/z 481

Example 157

Phenyl-[2-(R)-benzyl-4-(2'-chloro-biphenyl-4-ylmethyl)-piperazin-1-yl]-methanone

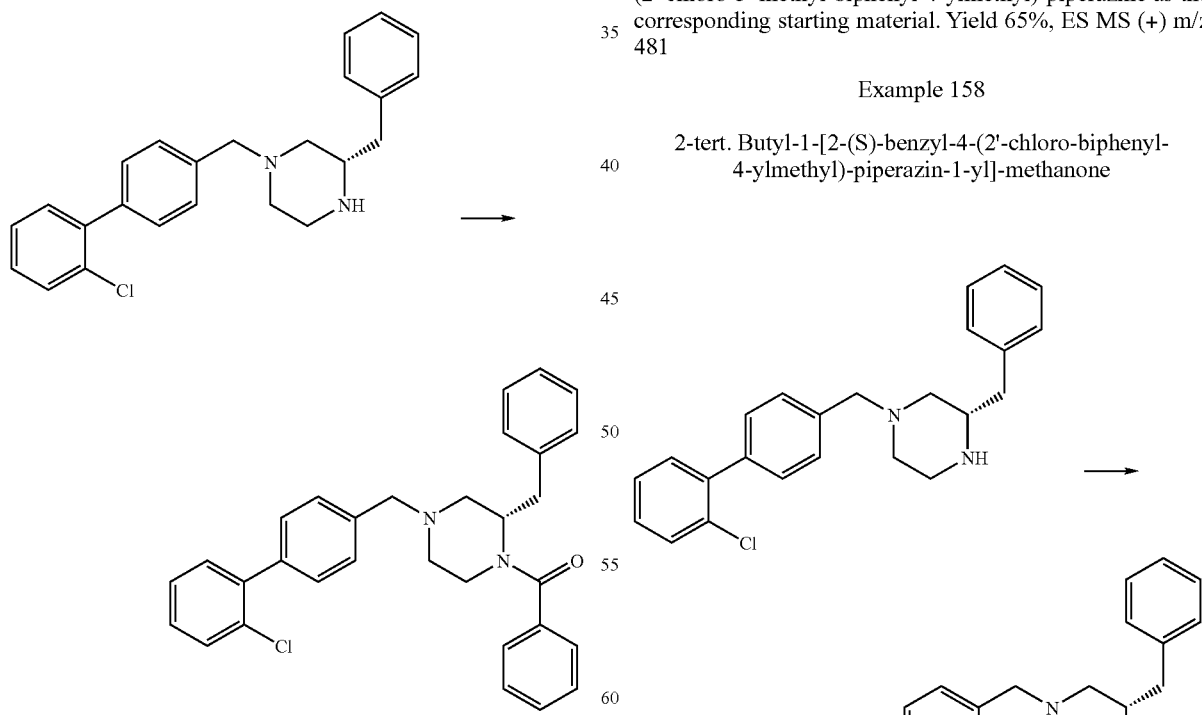

The hydrochloride salt of the above compound was made in the same manner as example 156 but with 3-(R)-benzyl-1-(2'-chloro-5'-methyl-biphenyl-4-ylmethyl)-piperazine as the corresponding starting material. Yield 65%, ES MS (+) m/z 481

Example 158

2-tert. Butyl-1-[2-(S)-benzyl-4-(2'-chloro-biphenyl-4-ylmethyl)-piperazin-1-yl]-methanone The hydrochloride salt of the above compound was made in the same manner as example 154, but with pivaloyl chloride as the appropriate acidchloride. Yield: 42%, ES MS (+) m/z 461

Example 159

2-tert. Butyl-1-[2-(R)-benzyl-4-(2'-chloro-biphenyl-4-ylmethyl)-piperazin-1-yl]-methanone

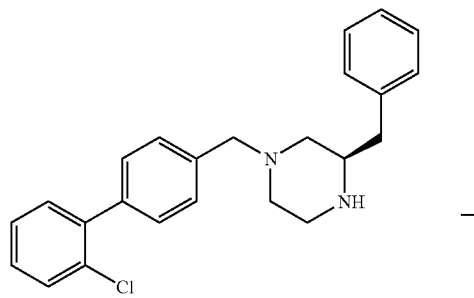

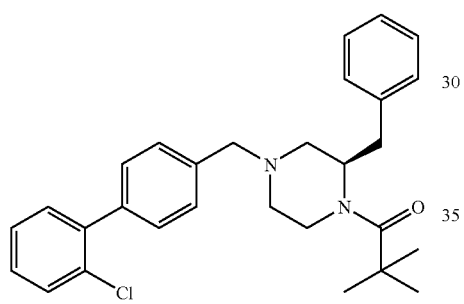

The hydrochloride salt of the above compound could be made in the same manner as example 158, but with 3-(R)-benzyl-1-(2'-chloro-biphenyl-4-ylmethyl)-piperazine as the corresponding starting material.

Example 160

2-Phenyl-1-[2-(S)-benzyl-4-(2'-chloro-biphenyl-4-ylmethyl)-piperazin-1-yl]-ethanone

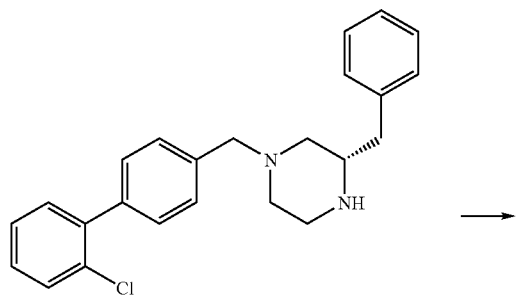

-continued

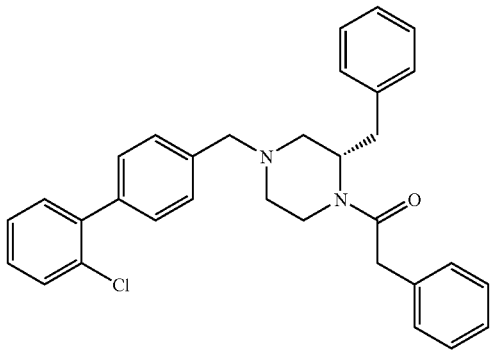

The hydrochloride salt of the above compound was made in the same manner as example 154, but with phenylacetyl chloride as the appropriate acidchloride. Yield: 58%, ES MS (+) m/z 495

Example 161

2-Phenyl-1-[2-(R)-benzyl-4-(2'-chloro-biphenyl-4-ylmethyl)-piperazin-1-yl]-ethanone

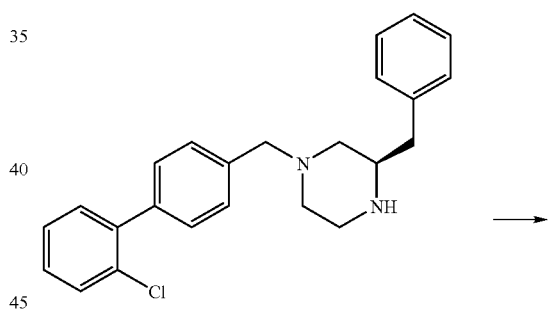

The hydrochloride salt of the above compound was made in the same manner as example 160, but with 3-(R)-benzyl-1-(2'-chloro-biphenyl-4-ylmethyl)-piperazine as the corresponding starting material. Yield: 65%, ES MS (+) m/z 495

Example 162

2-(S)-Benzyl-4-(2'-chloro-biphenyl-4-ylmethyl)-piperazine-1-carboxylic acid phenylamide

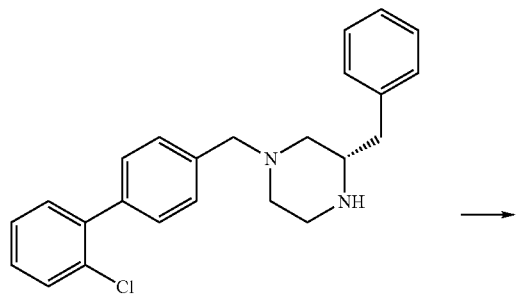

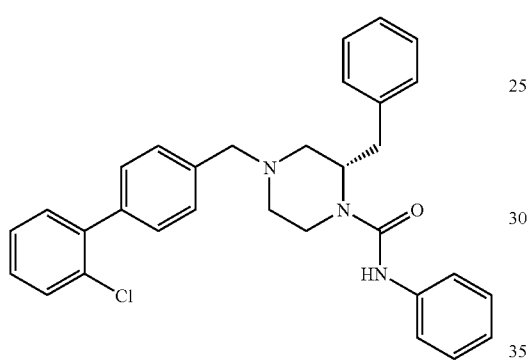

50 mg of 3-(S)-benzyl-1-(2'-chloro-biphenyl-4-ylmethyl)-piperazine were dissolved in dichloromethane, 2 equiv. phenylisocyanate was be added. The reaction was shaken at room temperature overnight. The reaction was concentrated in vacuo and the crude purified by column chromatography to afford 50 mg of the title compound as the free base. Treatment with 1 equiv. 2 M HCl in dioxane afforded 44 mg of its hydrochloride salt. Yield: 62%, ES MS (+) m/z 496.

Example 163

2-(R)-Benzyl-4-(2'-chloro-biphenyl-4-ylmethyl)-piperazine-1-carboxylic acid phenylamide

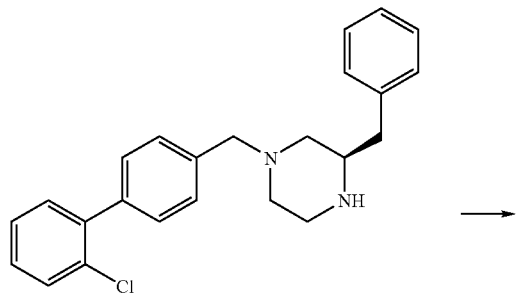

-continued

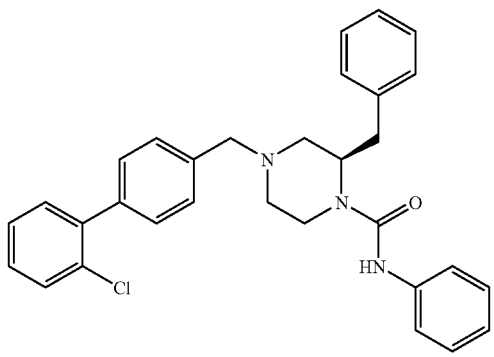

The hydrochloride salt of the above compound was prepared as in example 162, but with 3-(R)-benzyl-1-(2'-chloro-5'-methyl-biphenyl-4-ylmethyl)-piperazine as the corresponding starting material. Yield: 63%, ES MS (+) m/z 496.

Example 164

1-Methanesulfonyl-2-(S)-benzyl-4-(2'-chloro-biphenyl-4-ylmethyl)-piperazine

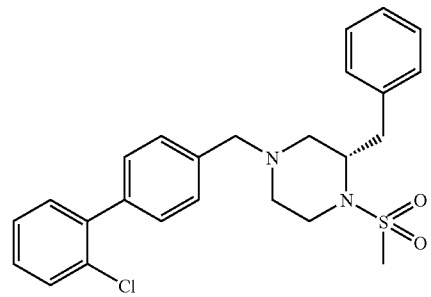

The above hydrochloride salt of the compound was made in the same manner as example 154, but with methanesulfonyl chloride as the appropriate acidchloride. Yield: 59%, ES MS (+) m/z 455.

Example 165

1-Methanesulfonyl-2-(R)-benzyl-4-(2'-chloro-biphenyl-4-ylmethyl)-piperazine

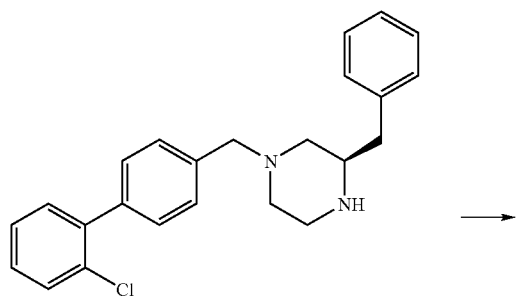

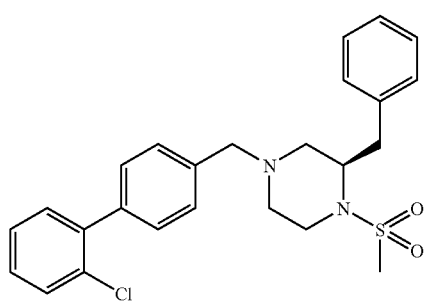

The hydrochloride salt of the above compound was made in the same manner as example 164, but with 3-(R)-benzyl-1-(2'-chloro-5'-methyl-biphenyl-4-ylmethyl)-piperazine as the corresponding starting material. Yield: 33%, ES MS (+) m/z 455

Example 166

(S)-1-Benzenesulfonyl-4-(2'-chloro-biphenyl-4-ylmethyl)-2-[(Z)-((Z)-2-propenyl)-penta-2,4-dienyl]-piperazine

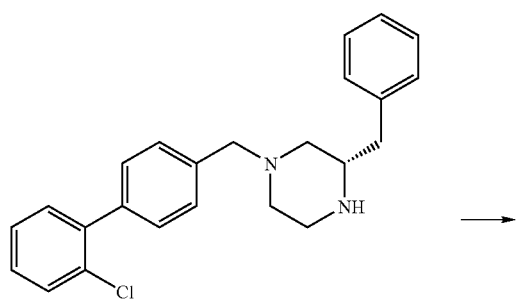

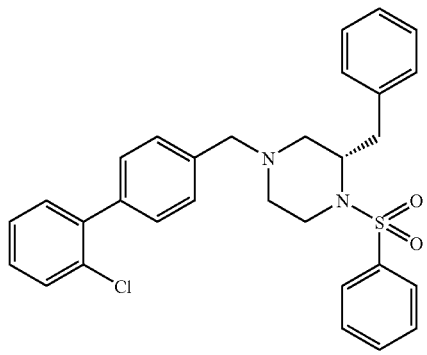

The hydrochloride salt of the above compound was made in the same manner as example 154, but with benzenesulfonyl chloride as the appropriate acidchloride. Yield: 52%, ES MS (+) m/z 517

Example 167

(R)-1-Benzenesulfonyl-4-(2'-chloro-biphenyl-4-ylmethyl)-2-[(Z)-((Z)-2-propenyl)-penta-2,4-dienyl]-piperazine

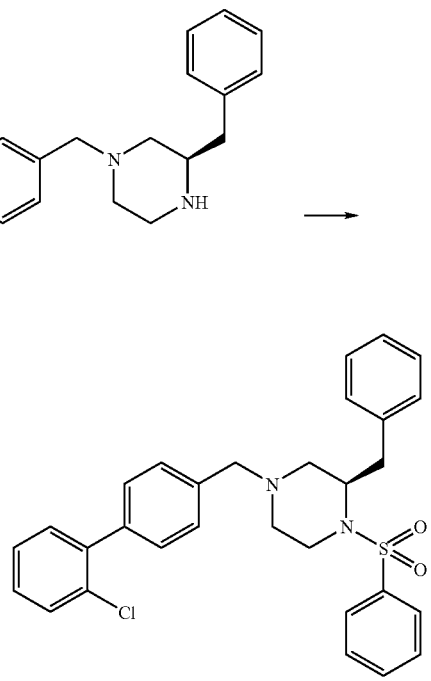

The hydrochloride salt of the above compound was made in the same manner as example 167, but with 3-(R)-benzyl-1-(2'-chloro-5'-methyl-biphenyl-4-ylmethyl)-piperazine as the corresponding starting material. Yield 33% ES MS (+) m/z 455

Example 168

1-Ethyl-2-(S)-benzyl-4-(2'-chloro-biphenyl-4-ylmethyl)-piperazine

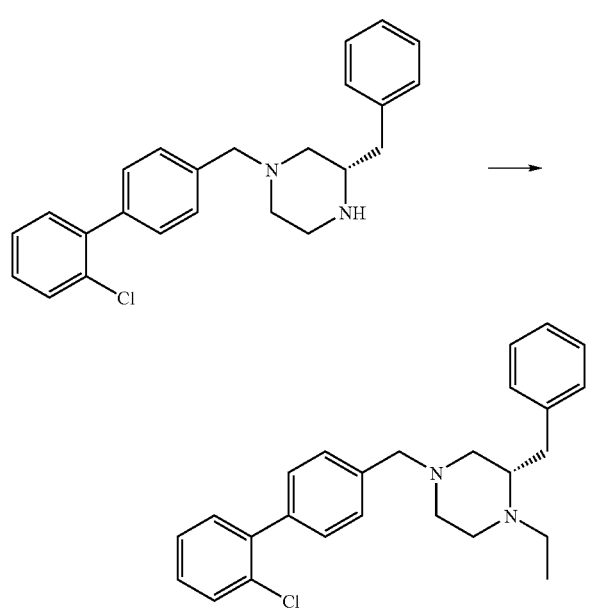

This compound was made in the following manner: 100 mg of 3-(S)-benzyl-1-(2'-chloro-biphenyl-4-ylmethyl)-piperazine was dissolved in THF, 3 equiv. of N,N-diisopropylethylamine were added followed by 2 equiv. of bromoethane. The reaction was be shaken at room temperature overnight. The reaction was concentrated in vacuo. The residue was diluted with DCM and washed with 1N aqueous NaOH solution. The organic layer was dried over $Na_2SO_4$, filtered and concentrated in vacuo. The crude residue was purified by column chromatography to afford the title compound as free base. Treatment with 1 equiv. 2M HCl in dioxane and concentration in vacuo gave 16 mg of its hydrochloride salt. Yield 27%, ES MS (+) m/z 405

Example 169

1-Ethyl-2-(R)-benzyl-4-(2'-chloro-biphenyl-4-ylmethyl)-piperazine

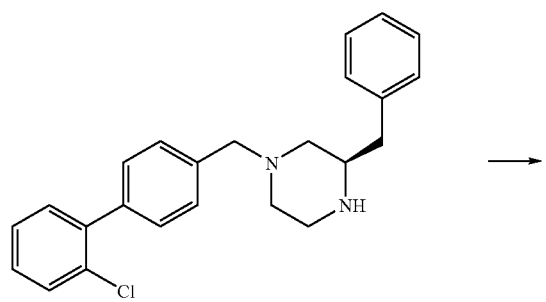

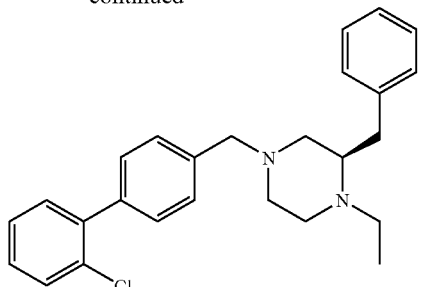

The hydrochloride salt of the above compound could be made in the same manner as example 168, but with 3-(R)-benzyl-1-(2'-chloro-5'-methyl-biphenyl-4-ylmethyl)-piperazine as the corresponding starting material.

Example 170

2-(S)-Benzyl-4-(2'-chloro-biphenyl-4-ylmethyl)-piperazine-1-carboxylic acid dimethylamide

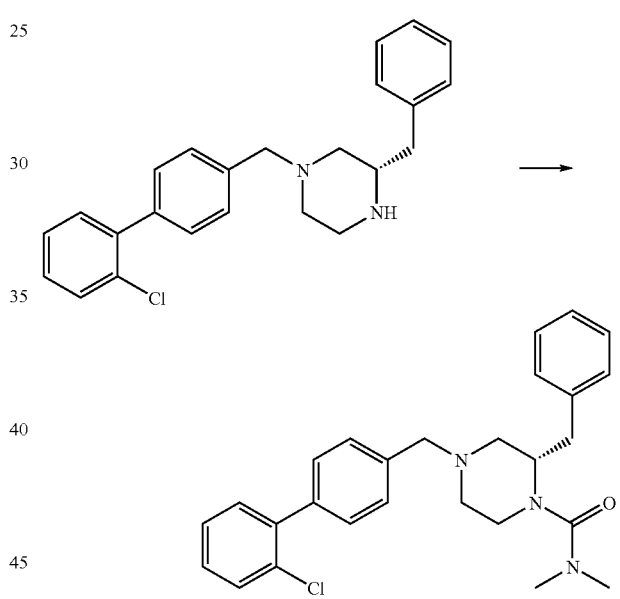

The above compound was made in the same manner as example 154, but with N,N-dimethylcarbamoyl chloride as the appropriate acidchloride. Yield 37%, ES MS (+) m/z 448

Example 171

2-(R)-Benzyl-4-(2'-chloro-biphenyl-4-ylmethyl)-piperazine-1-carboxylic acid dimethylamide

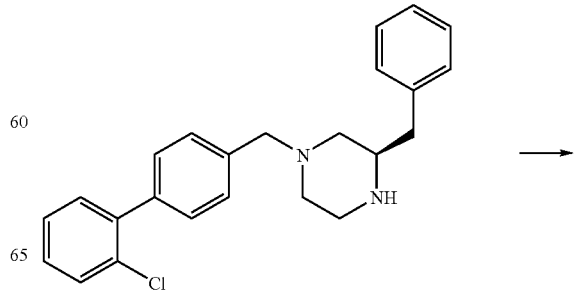

Example 173

2-(R)-Benzyl-4-(2'-chloro-biphenyl-4-ylmethyl)-piperazine-1-carboxylic acid methylamide

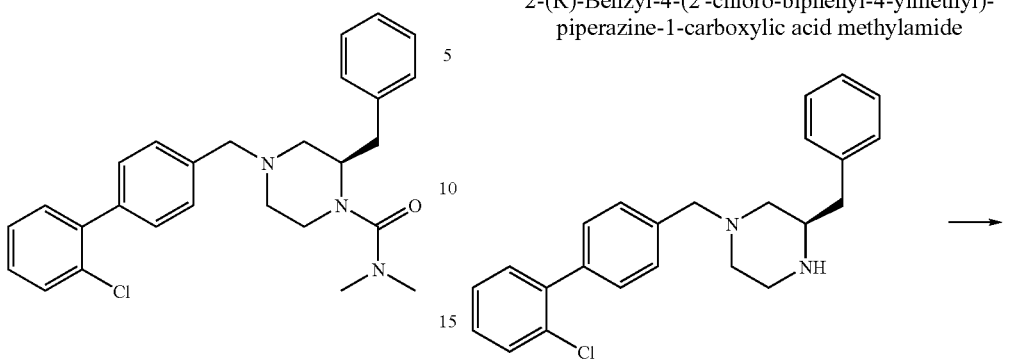

The above compound could be made in the same manner as example 170, but with 3-(R)-benzyl-1-(2'-chloro-biphenyl-4-ylmethyl)-piperazine as the appropriate starting material.

Example 172

2-(S)-Benzyl-4-(2'-chloro-biphenyl-4-ylmethyl)-piperazine-1-carboxylic acid methylamide

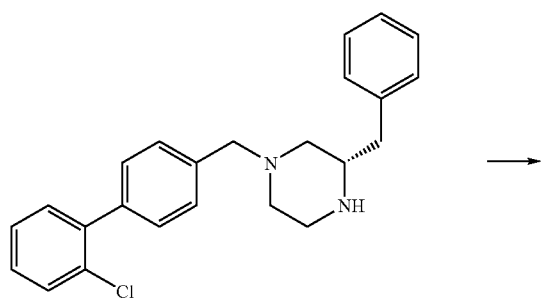

The hydrochloride salt of the above compound could be made in the same manner as example 172, but with 3-(R)-benzyl-1-(2'-chloro-biphenyl-4-ylmethyl)-piperazine as the appropriate starting material.

Example 174

3-Isopropyl-1-(2'-trifluoromethyl-biphenyl-4-ylmethyl)-piperazine

This compound could be made in the same manner as Example 33 or 105:

(2-tert-butoxycarbonylamino-3-methyl-butyrylamino)-acetic acid methyl ester

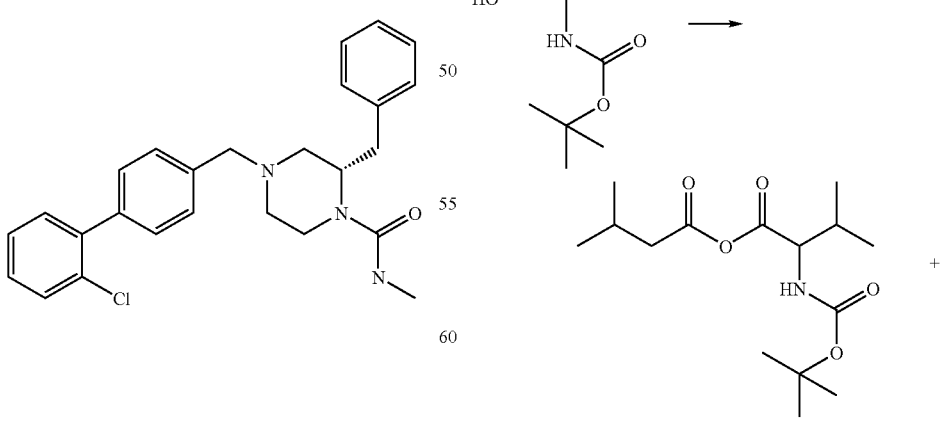

The hydrochloride salt of the above compound was made in the same manner as example 162, but with methyl isocyante as the appropriate isocyanate. Yield 70%, ES MS (+) m/z 434

121

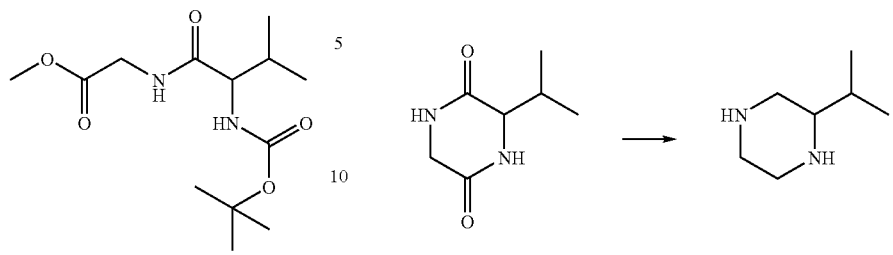

4 g of N-tert-butoxycarbonyl valine could be dissolved in THF under nitrogen atmosphere and cooled to 0° C. 1.1 equiv. of triethylamine could be added, followed by 1.1 equiv. of isobutylchloroformate to form the mixed anhydride solution. The reaction could be stirred at room temperature for 1 h. 1.1 equiv. of the HCl salt of glycine methyl ester could be dissolved in anhydrous dichloromethane, 1 eqiv. of triethylamine would be added. This solution would then be added dropwise to the cooled, mixed anhydride solution. The reaction could be stirred for 3 h at 0° C. The reaction could be filtered and the filtrate could be concentrated in vacuo. The residue could be taken up into ethyl acetate, washed with 5% aqueous citric acid solution, 5% aqueous sodium bicarbonate solution, water and brine. The organic phase could be dried over sodium sulfate, filtered and concentrated in vacuo to afford in a quantitative yield (2-tert-butoxycarbonylamino-3-methyl-butyrylamino)-acetic acid methyl ester.

3-Isopropyl-piperazine-2,5-dione

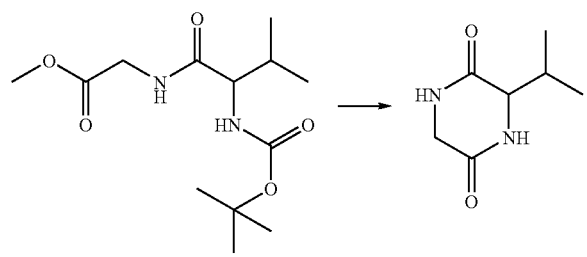

5 g of (2-tert-butoxycarbonylamino-3-methyl-butyrylamino)-acetic acid methyl ester could be dissolved in dichloromethane and trifluoroacetic acid could be added.

The reaction could be stirred at room temperature for 2.5 h. The reaction could be concentrated in vacuo and then be redissolved in 5% aqueous sodium bicarbonate solution. The reaction could be stirred at room temperature for 20 min, then methanol could be added. The reaction could be heated to 80° C. for 3 h. After cooling to room temperature, the basic aqueous phase could be extracted with ethyl acetate. The combined organic extracts could be dried over sodium sulfate, filtered and concentrated in vacuo to give 3-isopropyl-piperazine-2,5-dione.

122

2-Isopropyl-piperazine

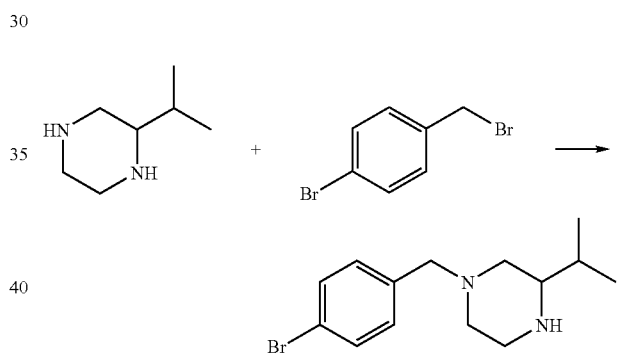

2 g of 3-isopropyl-piperazine-2,5-dione could be suspended in anhydrous THF under nitrogen and cooled in an ice-bath. 4 equiv. of lithium aluminium hydride could be added. The reaction could be stirred at 0° C. for 0.5 h, then heated to reflux overnight. The reaction could be quenched by the subsequent addition of 1 mL/gLiAlH$_4$ of water, 1 mL/gLiAlH$_4$ of 5% aqueous sodium hydroxide solution and 3 mL/gLiAlH$_4$ of water. The resulting solid could be separated by filtration through Celite and rinsed with ethyl acetate. The filtrate could be concentrated in vacuo to afford 2-isopropyl-piperazine.

1-(4-Bromo-benzyl)-3-isopropyl-piperazine 0.7 g of 2-isopropyl-piperazine could be dissolved in acetonitrile and cooled to 0° C. A solution of 0.5 quiv. 4-bromobenzylbromide in acetonitrile could be added dropwise over 1 h. The reaction would be stirred at room temperature for 2 h. The reaction mixture could be concentrated and the residue could be purified by column chromatography (silica, eluent dichloromethane, 0-5% methanol, 0-0.5% dimethylethylamine) to afford 1-(4-bromo-benzyl)-3-isopropyl-piperazine.

3-Isopropyl-1-(2'-trifluoromethyl-biphenyl-4-ylmethyl)-piperazine

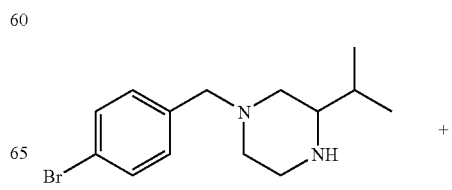
+

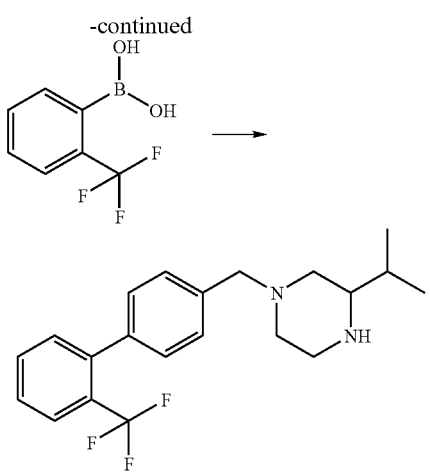

100 mg of 1-(4-bromo-benzyl)-3-isopropyl-piperazine could be combined with 1 equiv. of 2-trifluoromethylphenyl boronic acid, 10 mol % of tetrakis(triphenylphosphine)palladium(0), 2M sodium carbonate solution, toluene and ethanol. The reaction mixture could be heated in a sealed tube at 120° C. overnight. The reaction mixture could be filtered through Celite and concentrated in vacuo. The residue could be diluted with water and extracted with ethyl acetate. The combined organic phases could be washed with brine, dried over sodium sulfate, filtered and concentrated in vacuo. The crude material could be purified by flash chromatography to afford 3-isopropyl-1-(2'-trifluoromethyl-biphenyl-4-ylmethyl)-piperazine.

Example 175

2-Phenyl-4-[1-(2'-trifluoromethyl-biphenyl-4-yl)-ethyl]-morpholine

4-[1-(4-Bromo-phenyl)-ethyl]-2-phenyl-morpholine

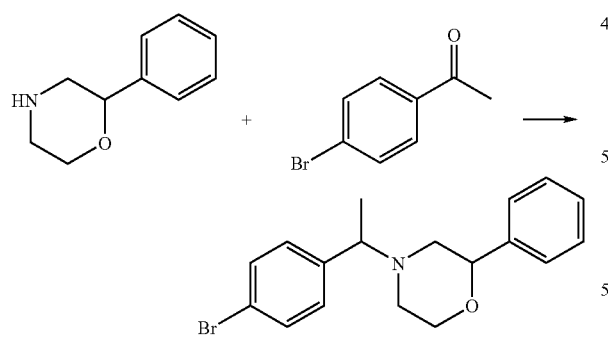

The above compound could be made the following way: 1 eq. of 2-Phenylmorpholine (Array) in dichloroethane could be combined with 1.2 eq. 4'-Bromoacetophenone (Aldrich) and stirred overnight at room temperature. 1.5 eq. borane-pyridine complex could be added and the reaction stirred for several hours. The reaction mixture could be diluted with methylene chloride and washed with water and brine. The organics could be dried over sodium sulfate and purified by column chromatography.

2-Phenyl-4-[1-(2'-trifluoromethyl-biphenyl-4-yl)-ethyl]-morpholine

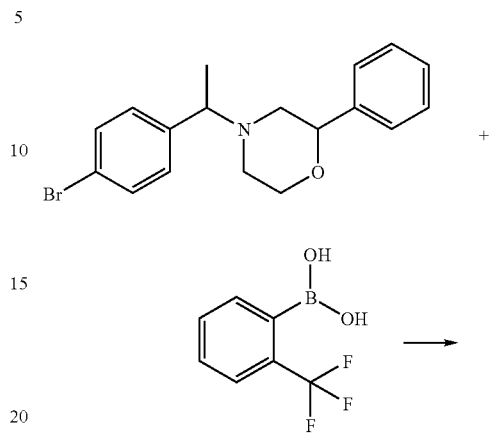

The above compound could be made in an analogous fashion to Example 2, but with 2-Trifluoromethylboronic acid as the boronic acid.

Example 176

2-Phenyl-4-[6-(2-trifluoromethyl-phenyl)-pyridin-3-ylmethyl]-morpholine 4-(6-Bromo-pyridin-3-ylmethyl)-2-phenyl-morpholine

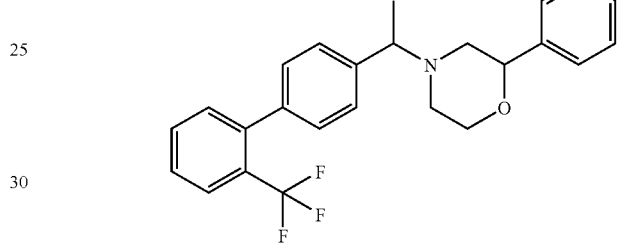

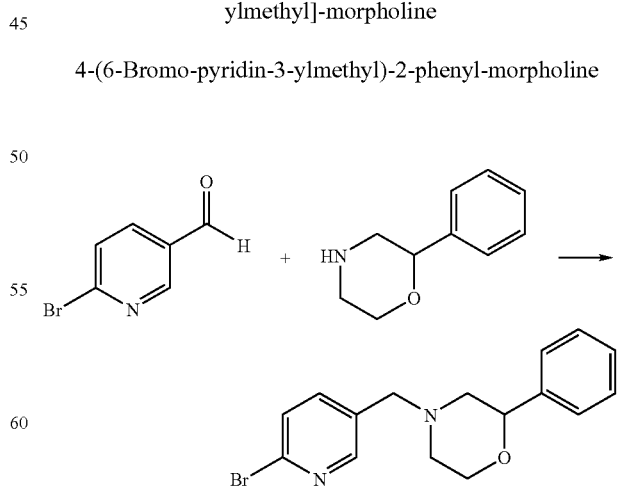

The above compound was made in the same manner as Example 1 but with the appropriate aldehyde and morpholine. 20% yield. ES MS (+)m/z 333

125

2-Phenyl-4-[6-(2-trifluoromethyl-phenyl)-pyridin-3-ylmethyl]-morpholine

126

3-Phenyl-1-[6-(2-trifluoromethyl-phenyl)-pyridin-3-ylmethyl]-piperazine

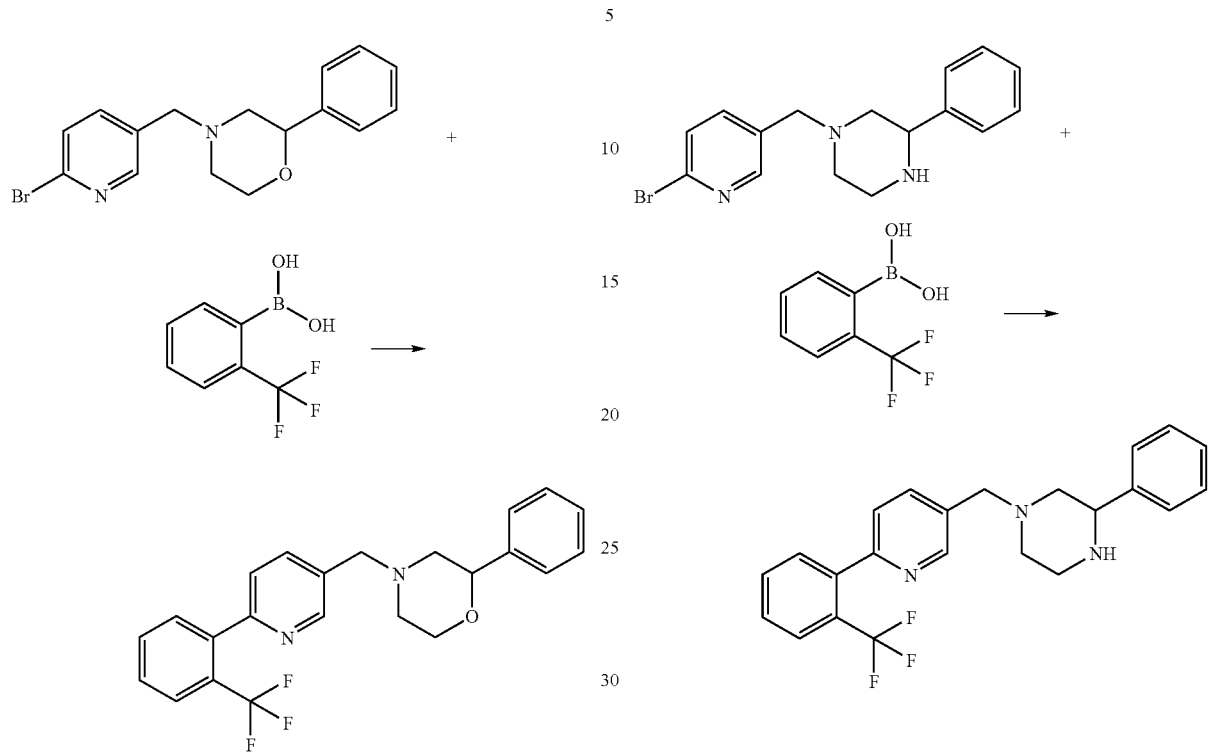

above compound was made in the same manner as Example 1 but with the appropriate aryl halide and boronic acid. 97% yield. ES MS (+)m/z 399

Example 177

3-Phenyl-1-[6-(2-trifluoromethyl-phenyl)-pyridin-3-ylmethyl]-piperazine 1-(6-Bromo-pyridin-3-ylmethyl)-3-phenyl-piperazine The above compound could be made in an analogous fashion to Example 7, but with 2-Trifluoromethylboronic acid as the boronic acid.

Example 178

2-Phenyl-4-[2-(2-trifluoromethyl-phenyl)-pyrimidin-5-ylmethyl]-morpholine 4-(2-Chloro-pyrimidin-5-ylmethyl)-2-phenyl-morpholine

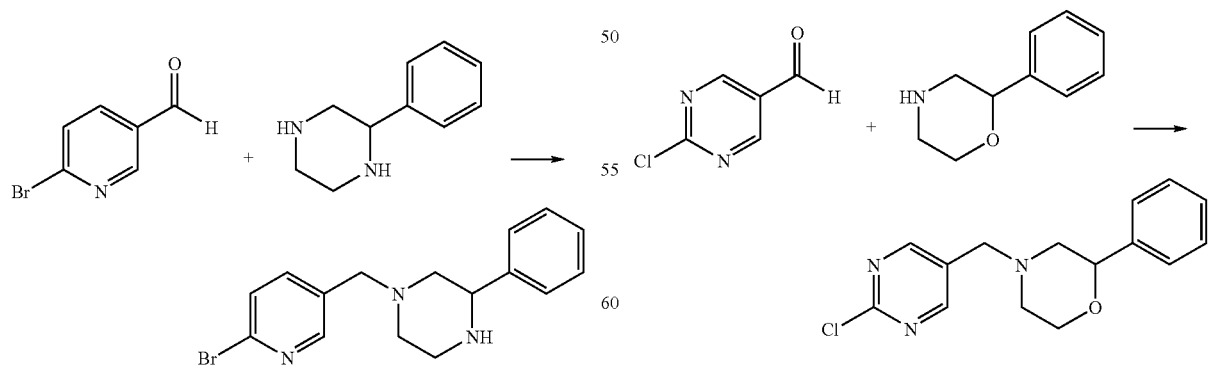

The above compound could be made in an analogous fashion to example 33, but with 6-Bromo-3-pyridinecarboxaldehyde as the aldehyde.

The above compound could be made in an analogous fashion to Example 1 but with 2-Chloro-pyrimidine-5-carbaldehyde, which is made by methods known in the literature (J. Med. Chem. 2000, 43, 3995-4004).

127

2-Phenyl-4-[2-(2-trifluoromethyl-phenyl)-pyrimidin-5-ylmethyl]-morpholine

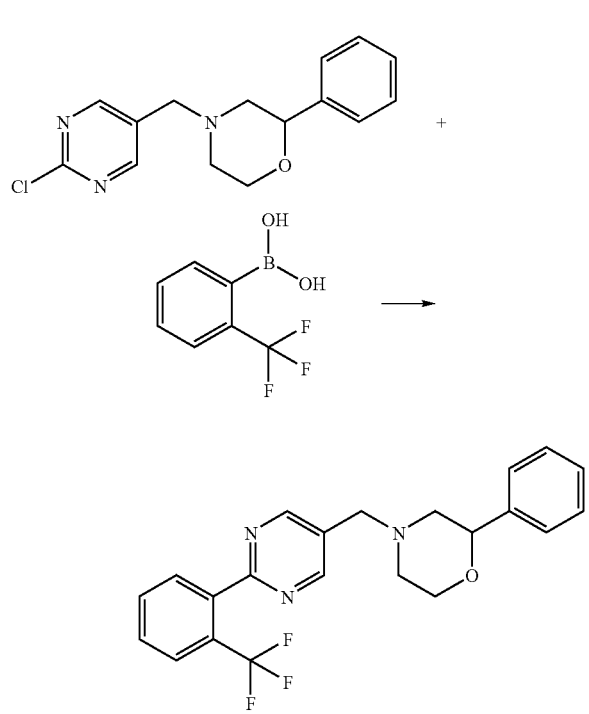

The above compound could be made in an analogous fashion to Example 2, but with 2-Trifluoromethylboronic acid as the boronic acid.

Example 179

5-(3-Phenyl-piperazin-1-ylmethyl)-2-(2-trifluoromethyl-phenyl)-pyrimidine

2-Chloro-5-(3-phenyl-piperazin-1-ylmethyl)-pyrimidine

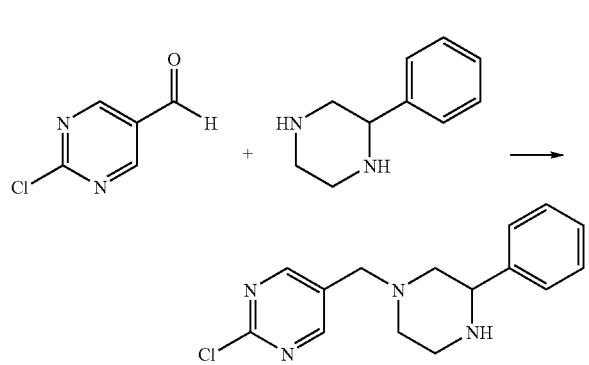

The above compound could be made in an analogous fashion to Example 33 but with 2-Chloro-pyrimidine-5-carbaldehyde, which is made by methods known in the literature (J. Med. Chem. 2000, 43, 3995-4004).

128

5-(3-Phenyl-piperazin-1-ylmethyl)-2-(2-trifluoromethyl-phenyl)-pyrimidine

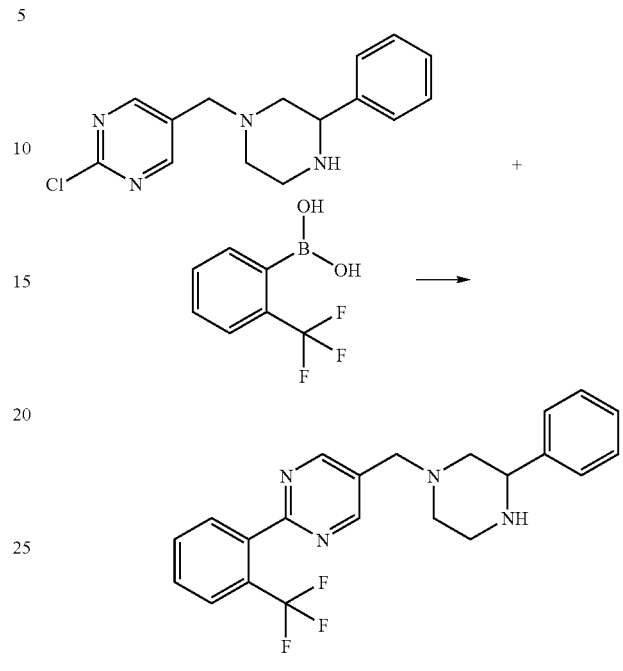

above compound could be made in an analogous fashion to Example 2, but with 2-Trifluoromethylboronic acid as the boronic acid.

Example 180

((S)-3-Benzyl-piperazin-1-yl)-(2',3'-dichloro-biphenyl-4-yl)-methanone ((S)-3-Benzyl-piperazin-1-yl)-(4-chloro-phenyl)-methanone

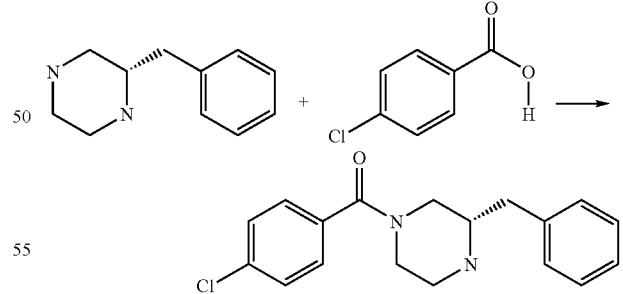

1.0 g of 2-(S) benzylpiperazine were dissolved in DCM and cooled to 0° C. A solution of 0.75 equiv. 4-bromobenzyl-bromide in acetonitrile was added dropwise over 1 h. The reaction was stirred at room temperature for 2 h. The reaction mixture was concentrated and the residue was purified by column chromatography (silica, eluent dichloromethane, 0-5% methanol, 0-0.5% dimethylethylamine) to afford 0.88 g of (3-(S)-benzyl-piperazin-1-yl)-(4-chloro-phenyl)-methanone. ES MS (+) m/z 315/317.

((S)-3-Benzyl-piperazin-1-yl)-(2',3'-dichloro-biphenyl-4-yl)-methanone

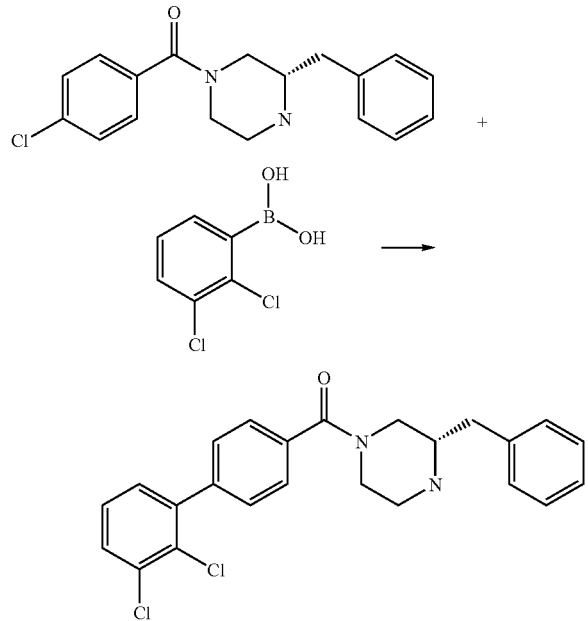

The above compound was made in the same manner as Example 1 but with the appropriate aryl bromide and boronic acid. 3% yield. ES MS (+)m/z 426.

Example 181

(S)-3-Benzyl-1-[4-(2-chloro-thiophen-3-yl)-benzyl]-piperazine

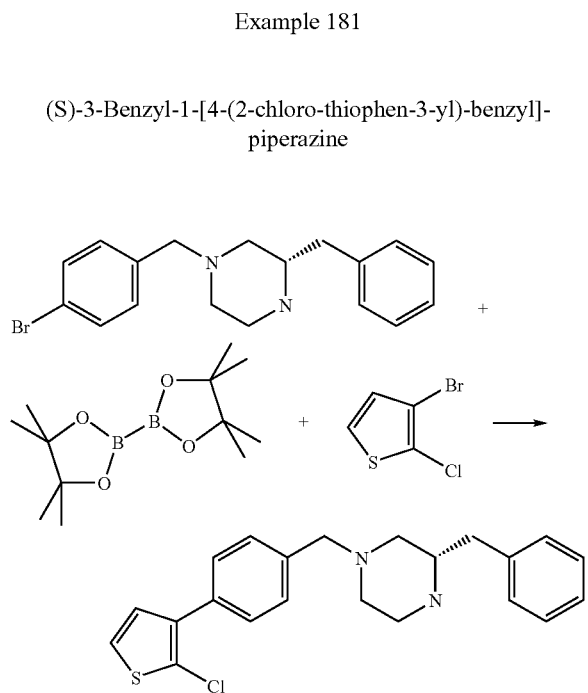

The above compound was made in the same manner as Example 7 but with the appropriate arylbromides. 56% yield. ES MS (+)m/z 383

Example 182

4'-((S)-3-Benzyl-piperazin-1-ylmethyl)-biphenyl-2-carbonitrile

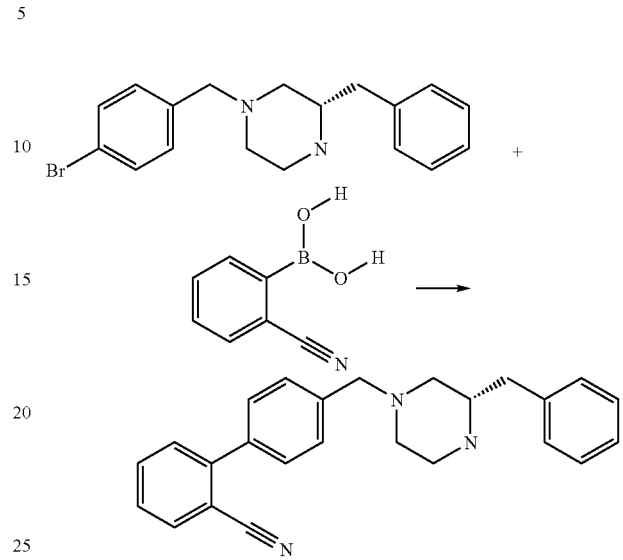

The above compound was made in the same manner as Example 1 but with the appropriate aryl bromide and boronic acid. 24% yield. ES MS (+)m/z 368

Example 183

(S)-4-(2',3'-Dichloro-biphenyl-4-ylmethyl)-2-phenyl-morpholine

The above compound was made in the same manner as Example 1 but with the appropriate aryl bromide and boronic acid. 78% yield. ES MS (+)m/z 398/400

Example 184

(S)-2-Benzyl-1-methyl-4-(2'-trifluoromethyl-biphenyl-4-ylmethyl)-piperazine (S)-2-Benzyl-4-(4-bromo-benzyl)-1-methyl-piperazine

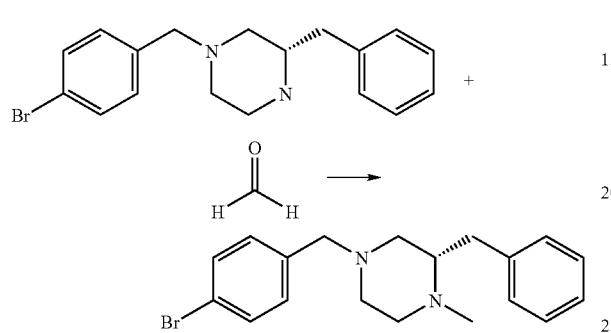

To a solution of 369 mg of 3-(S)-benzyl-1-(4-bromobenzyl)-piperazine in 3 mL of tetrahydrofuran was added 0.8 mL of formaldehyde and 0.15 mL acetic acid. After 2 h, 453 mg of sodium triacetoxyborohydride was added and the reaction was stirred overnight. Diluted carefully with aqueous saturated sodium bicarbonate solution and extracted with ethyl acetate. The combined organics were washed with brine, dried with sodium sulfate, filtered and concentrated in vacuo. Used crude in subsequent reactions. 82% yield. ES MS (+)m/z 361

(S)-2-Benzyl-1-methyl-4-(2'-trifluoromethyl-biphenyl-4-ylmethyl)-piperazine

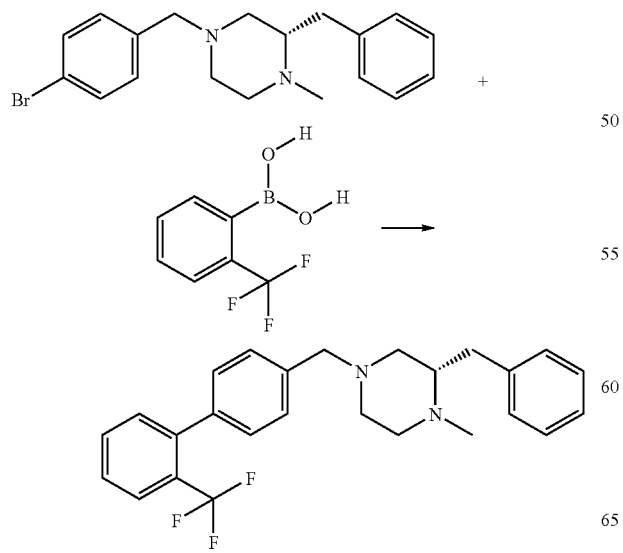

The above compound was made in the same manner as Example 1 but with the appropriate aryl bromide and boronic acid. 94% yield. ES MS (+)m/z 425

Example 185

(S)-2-Benzyl-4-(2'-chloro-biphenyl-4-ylmethyl)-1-methyl-piperazine

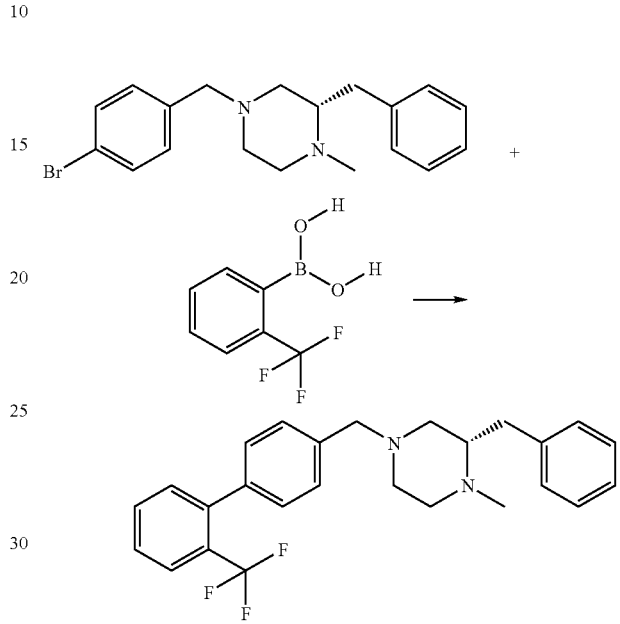

The above compound was made in the same manner as Example 1 but with the appropriate aryl bromide and boronic acid. 100% yield. ES MS (+)m/z 390

Example 186

(S)-3-Benzyl-1-(6-phenyl-pyridin-3-ylmethyl)-piperazine

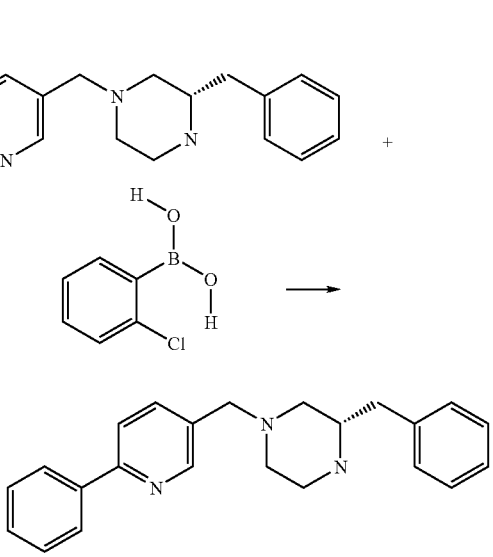

The above compound was made in the same manner as Example 1 but with the appropriate aryl halide and boronic acid. 33% yield. ES MS m/z 344

Example 187

(S)-2-Benzyl-4-(2',3'-dichloro-biphenyl-4-ylmethyl)-1-methyl-piperazine

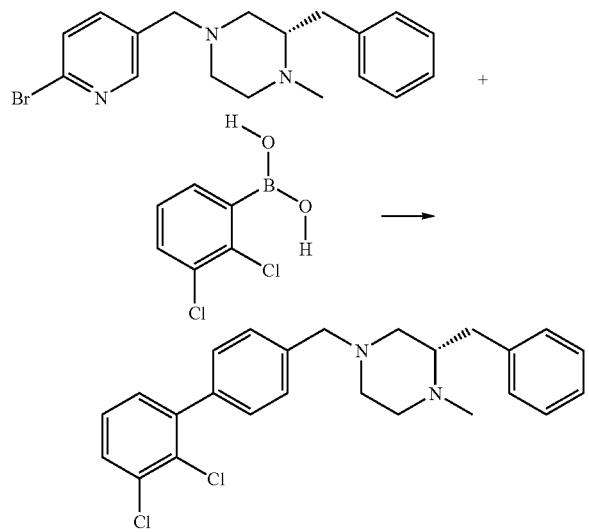

The above compound was made in the same manner as Example 1 but with the appropriate aryl halide and boronic acid. 20% yield. ES MS m/z 426

Example 188

(S)-2-Phenyl-4-(6-phenyl-pyridin-3-ylmethyl)-morpholine

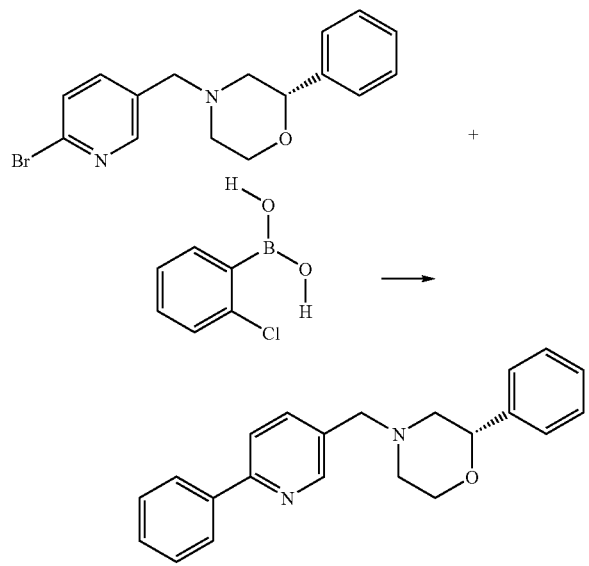

The above compound was made in the same manner as Example 1 but with the appropriate aryl halide and boronic acid. 50% yield. ES MS m/z 331

Example 189

(S)-4-[6-(3-Chloro-phenyl)-pyridin-3-ylmethyl]-2-phenyl-morpholine

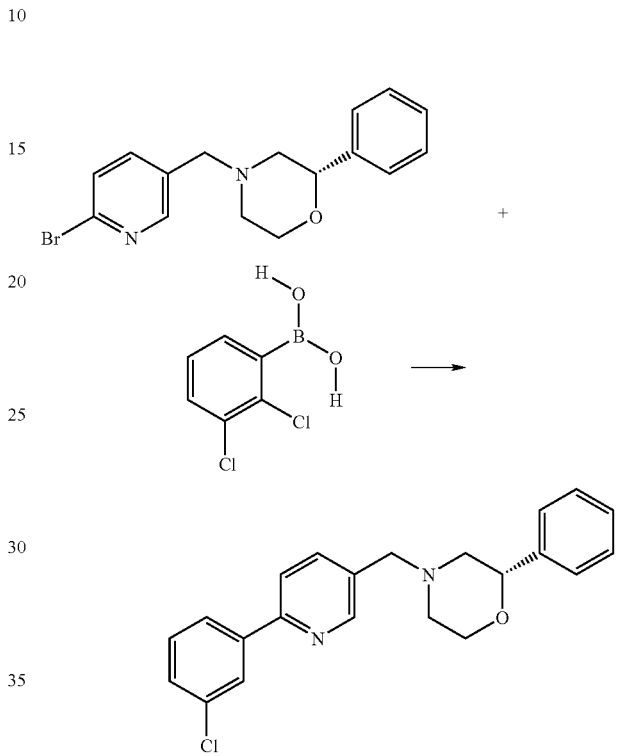

The above compound was made in the same manner as Example 1 but with the appropriate aryl halide and boronic acid. 50% yield. ES MS m/z 365

Example 190

(S)-4-(2'-Chloro-5'-methyl-biphenyl-4-ylmethyl)-2-phenyl-morpholine

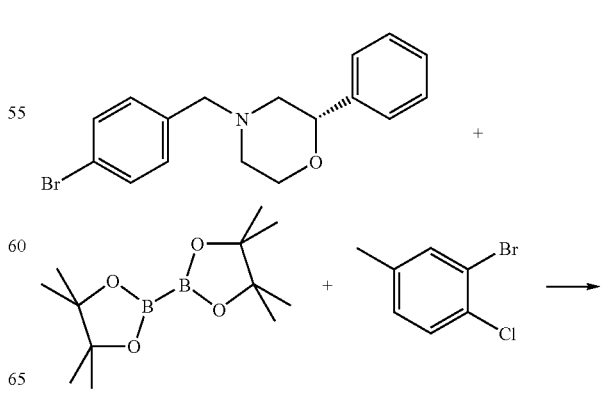

-continued

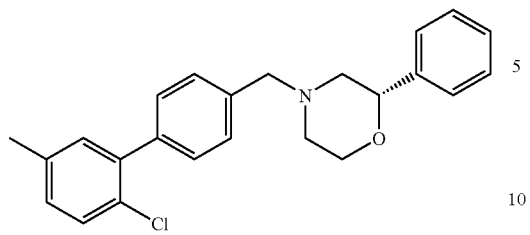

The above compound was made in the same manner as Example 7 but with the appropriate arylbromides. 34% yield. ES MS (+)m/z 377

Example 191

(S)-4-[4-(2-Chloro-thiophen-3-yl)-benzyl]-2-phenyl-morpholine

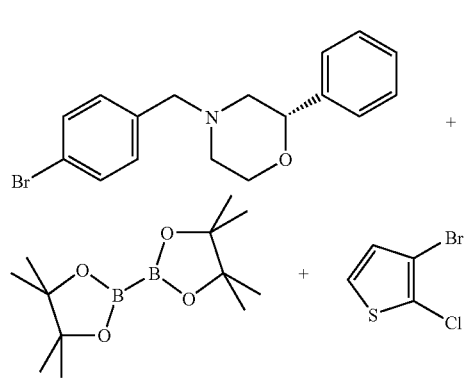

The above compound was made in the same manner as Example 7 but with the appropriate arylbromides. 42% yield. ES MS (+)m/z 370

Example 192

4'-((S)-2-Phenyl-morpholin-4-ylmethyl)-biphenyl-2-carbonitrile

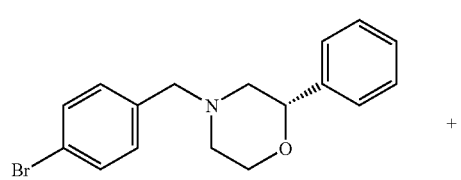

-continued

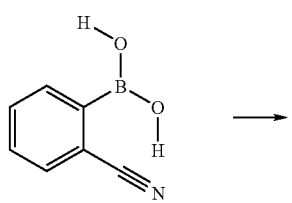

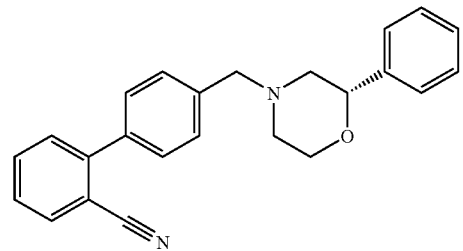

The above compound was made in the same manner as Example 1 but with the appropriate aryl halide and boronic acid. 29% yield. ES MS m/z 355

Example 193

(S)-4-(2'-Chloro-biphenyl-4-ylmethyl)-2-phenyl-morpholine

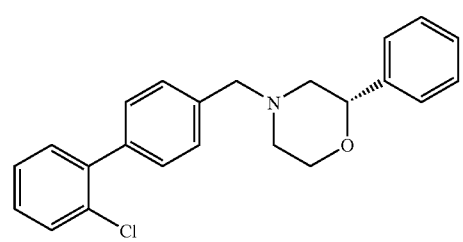

The above compound was made in the same manner as Example 1 but with the appropriate aryl halide and boronic acid. 100% yield. ES MS m/z 364

Example 194

(S)-4-(2',5'-Dichloro-biphenyl-4-ylmethyl)-2-phenyl-morpholine

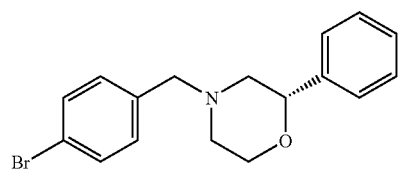

+

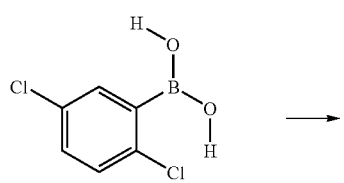

→

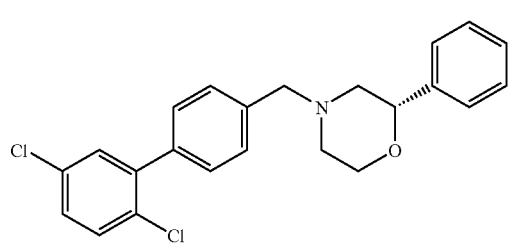

The above compound was made in the same manner as Example 1 but with the appropriate aryl halide and boronic acid. 57% yield. ES MS m/z 398

Example 195

2-Phenyl-4-(2'-trifluoromethyl-biphenyl-4-ylmethyl)-thiomorpholine 1,1-dioxide

4-(4-Bromo-benzyl)-2-phenyl-thiomorpholine

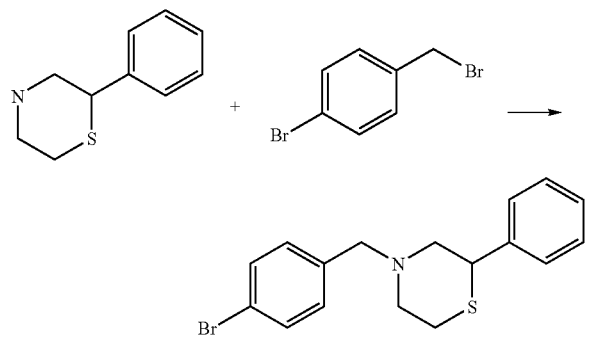

The above compound was made in the same manner as Example 2 but from commercially available 2-Phenylthiomorpholine. 28% yield. ES MS m/z 348/350

4-(4-Bromo-benzyl)-2-phenyl-thiomorpholine 1-oxide and 4-(4-Bromo-benzyl)-2-phenyl-thiomorpholine 1,1-dioxide

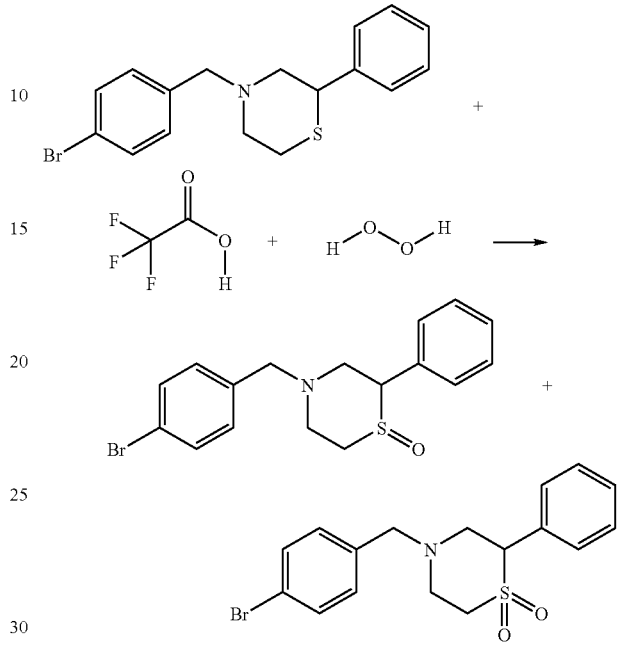

317 mg of 4-(4-Bromo-benzyl)-2-phenyl-thiomorpholine was dissolved in 3.2 mL of dichloromethane and a solution of 0.28 mL hydrogen peroxide (30% in water) and 2.76 mL of trifluoroacetic acid was added. The reaction stirred for 3.5 days at room temperature. The solution was diluted with aqueous saturated sodium bicarbonate solution and extracted with dichloromethane. The combined organics were washed with brine, dried with sodium sulfate and concentrated. The crude material was purified by flash chromatography to afford 37 mg of 4-(4-Bromo-benzyl)-2-phenyl-thiomorpholine 1-oxide and 36.5 mg of 4-(4-Bromo-benzyl)-2-phenyl-thiomorpholine 1,1-dioxide. ES MS m/z 365 and 382 respectively.

2-Phenyl-4-(2'-trifluoromethyl-biphenyl-4-ylmethyl)-thiomorpholine 1,1-dioxide

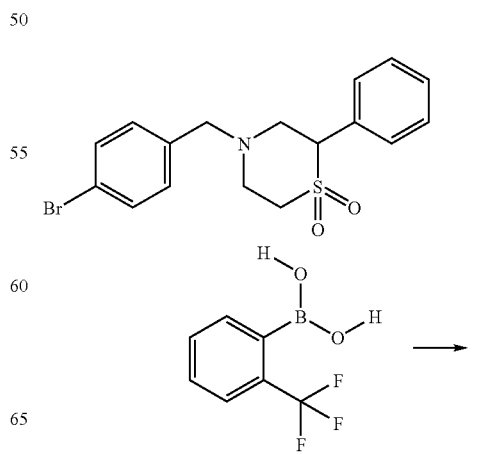

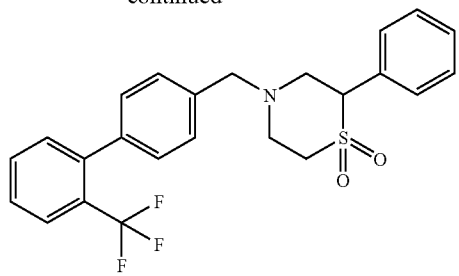

The above compound was made in the same manner as Example 1 but with the appropriate aryl halide and boronic acid. 64% yield. ES MS m/z 446

Example 196

2-Phenyl-4-(2'-trifluoromethyl-biphenyl-4-ylmethyl)-thiomorpholine 1-oxide

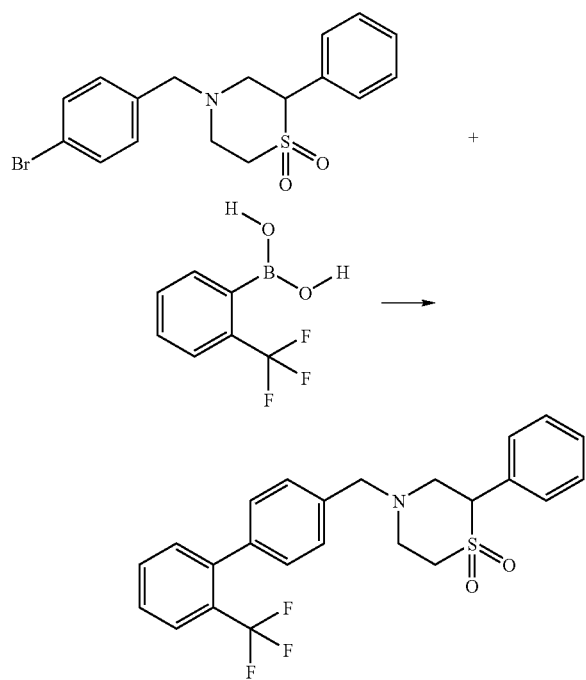

The above compound was made in the same manner as Example 1 but with the appropriate aryl halide and boronic acid. 67% yield. ES MS m/z 430

Example 197

1-(2'-Chloro-5'-methyl-biphenyl-4-ylmethyl)-3-phenyl-piperidine

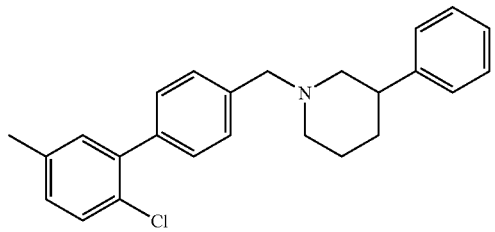

The above compound was made in a similar manner as Example 48 but with the appropriate boronic acid. 26% yield ES MS m/z 376.

Example 198

1-(2',5'-Dimethyl-biphenyl-4-ylmethyl)-3-phenyl-piperidine

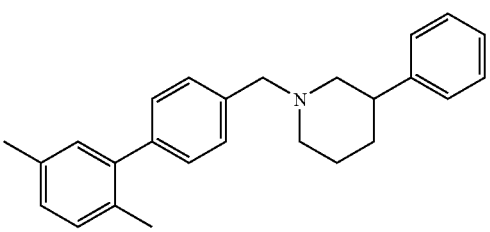

The above compound was made in a similar manner as Example 48 but with the appropriate boronic acid. 68% yield ES MS m/z 356.

Assessment of Biological Properties

The biological properties of the compounds of the formula I were assessed using the assays described below.

A. Human CB1 and CB2 Receptor Binding:

Experimental Method:

CB2 membranes were purchased and made from HEK293 EBNA cells stably transfected with human CB2 receptor cDNA (Perkin Elmer Life and Analytical Sciences). CB1 membranes were isolated from HEK cells stably co-transfected with human CB1 receptor and Gα16 cDNA's. The membrane preparation was bound to scintillation beads (Ysi-Poly-L-lysine SPA beads, GE Healthcare) for 4 hours at room temperature in assay buffer containing 50 mM Tris, pH 7.5, 2.5 mM EDTA, 5 mM $MgCl_2$, 0.8% fatty acid free Bovine Serum Albumin. Unbound membrane was removed by washing in assay buffer. Membrane-bead mixture was added to 96-well assay plates in the amounts of 15 ug membrane per well (CB2) or 2.5 ug per well (CB1) and 1 mg SPA bead per well. Compounds were added to the membrane-bead mixture in dose-response concentrations ranging from $1\times10^{-5}$ M to $1\times10^{-10}$ M with 0.25% DMSO, final. The competition reaction was initiated with the addition of $^3$H-CP55940 (Perkin Elmer Life and Analytical Sciences) at a final concentration of 1.5 nM (CB2) or 2.5 nM (CB1). The reaction was incubated at room temperature for 18 hours and read on TopCount NXT plate reader. Total and non-specific binding was determined in the absence and presence of 1.25 uM Win 55212 (Sigma). IC50 values for each compound were calculated as the concentration of compound that inhibits the specific binding of the radioactively labeled ligand to the receptor by 50% using the XLFit 4.1 four parameter logistic model. IC50 values were converted to inhibition constant (Ki) values using Cheng-Prusoff equation.

B. CB2R Mediated Modulation of cAMP Synthesis:

Compounds of the invention were evaluated for their CB2 agonist or inverse agonistic activity in accordance with the following experimental method. Compounds which were shown to bind to CB2 by the binding assay described above but which were not shown to exhibit CB2R-mediated modulation of cAMP synthesis by this assay were presumed to be CB2 antagonists.

Experimental Method:

CHO cells expressing human CB2R (Euroscreen) were plated at a density of 5000 cells per well in 384 well plates and incubated overnight at 37° C. After removing the media, the cells were treated with test compounds diluted in stimulation buffer containing 1 mM IBMX, 0.25% BSA and 10 uM Forskolin. The assay was incubated for 30 minutes at 37° C. Cells were lysed and the cAMP concentration was measured using DiscoverX-XS cAMP kit, following the manufacturer's protocol. In this setting, agonists will decrease forskolin induced production of cAMP while inverse agonists will further increase forskolin induced production of cAMP. EC50 of agonists were calculated as follows. The maximal amount of cAMP produced by forskolin compared to the level of cAMP inhibited by 1 uM CP55940 is defined as 100%. The EC50 value of each test compound was determined as the concentration at which 50% of the forskolin-stimulated cAMP synthesis was inhibited. Data was analyzed using a four-parameter logistic model. (Model 205 of XLfit 4.0).

C. CB1R Mediated Modulation of cAMP Synthesis:

Compounds of the invention were evaluated for their CB1 agonist or inverse agonistic activity in accordance with the following experimental method. Compounds which were shown to bind to CB1 by the binding assay described above but which were not shown to exhibit CB1R-mediated modulation of cAMP synthesis by this assay were presumed to be CB1 antagonists.

Experimental Method:

CHO cells expressing human CB1R (Euroscreen) were plated at a density of 5000 cells per well in 384 well plates and incubated overnight at 37° C. After removing the media, the cells were treated with test compounds diluted in stimulation buffer containing 1 mM IBMX, 0.25% BSA and 10 uM Forskolin. The assay was incubated for 30 minutes at 37° C. Cells were lysed and the cAMP concentration was measured using DiscoverX-XS cAMP kit, following the manufacturer's protocol. In this setting, agonists will decrease forskolin induced production of cAMP while inverse agonists will further increase forskolin induced production of cAMP. EC50 of agonists were calculated as follows. The maximal amount of cAMP produced by forskolin compared to the level of cAMP inhibited by 1 uM CP55940 is defined as 100%. The EC50 value of each test compound was determined as the concentration at which 50% of the forskolin-stimulated cAMP synthesis was inhibited. Data was analyzed using a four-parameter logistic model. (Model 205 of XLfit 4.0).

Compounds Having Agonist Activity

Through the use of the above described assays the following compounds were found to exhibit agonistic activity and thus to be particularly well suited for the treatment of pain as well as for the treatment of inflammation.

2-Phenyl-4-(2'-trifluoromethyl-biphenyl-4-ylmethyl)-morpholine;
4-(2'-Chloro-biphenyl-4-ylmethyl)-2-phenyl-morpholine;
4-(2'-Chloro-5'-methyl-biphenyl-4-ylmethyl)-2-phenyl-morpholine;
4-(2'-Trifluoromethyl-biphenyl-4-ylmethyl)-morpholine;
4-(2',3'-Dichloro-biphenyl-4-ylmethyl)-2-phenyl-morpholine;
4'-(2-Phenyl-morpholin-4-ylmethyl)-biphenyl-2-carbonitrile;
4-(2'-Ethoxy-biphenyl-4-ylmethyl)-2-phenyl-morpholine;
4-[4-(2-Chloro-thiophen-3-yl)-benzyl]-2-phenyl-morpholine;
2-Phenyl-4-(4-pyridin-2-yl-benzyl)-morpholine;
1-Benzenesulfonyl-2-phenyl-4-(2'-trifluoromethyl-biphenyl-4-ylmethyl)-piperazine;
3-Benzyl-1-(2'-trifluoromethyl-biphenyl-4-ylmethyl)-piperazine;
Phenyl-[2-benzyl-4-(2'-trifluoromethyl-biphenyl-4-ylmethyl)-piperazin-1-yl]-methanone;
2-Phenyl-4-(4-thiophen-3-yl-benzyl)-morpholine;
3-Phenyl-1-(2'-trifluoromethyl-biphenyl-4-ylmethyl)-piperidine;
1-(2'-Chloro-biphenyl-4-ylmethyl)-3-phenyl-piperidine;
(S)-4-(2',3'-Dichloro-biphenyl-4-ylmethyl)-2-phenyl-morpholine;
(S)-2-Phenyl-4-[6-(2-trifluoromethyl-phenyl)-pyridin-3-ylmethyl]-morpholine;
(S)-3-Benzyl-1-(6-phenyl-pyridin-3-ylmethyl)-piperazine;
(S)-2-Phenyl-4-(6-phenyl-pyridin-3-ylmethyl)-morpholine;
(S)-4-[6-(3-Chloro-phenyl)-pyridin-3-ylmethyl]-2-phenyl-morpholine;
(S)-4-(2'-Chloro-5'-methyl-biphenyl-4-ylmethyl)-2-phenyl-morpholine;
(S)-4-[4-(2-Chloro-thiophen-3-yl)-benzyl]-2-phenyl-morpholine;
4'-((S)-2-Phenyl-morpholin-4-ylmethyl)-biphenyl-2-carbonitrile; and
(S)-4-(2'-Chloro-biphenyl-4-ylmethyl)-2-phenyl-morpholine;

Of the above compounds, the following are preferred:
2-Phenyl-4-(2'-trifluoromethyl-biphenyl-4-ylmethyl)-morpholine;
4-(2'-Chloro-biphenyl-4-ylmethyl)-2-phenyl-morpholine;
4-(2'-Chloro-5'-methyl-biphenyl-4-ylmethyl)-2-phenyl-morpholine;
3-Phenyl-1-(2'-trifluoromethyl-biphenyl-4-ylmethyl)-piperidine;
1-(2'-Chloro-biphenyl-4-ylmethyl)-3-phenyl-piperidine;
(S)-4-(2',3'-Dichloro-biphenyl-4-ylmethyl)-2-phenyl-morpholine;
(S)-2-Phenyl-4-[6-(2-trifluoromethyl-phenyl)-pyridin-3-ylmethyl]-morpholine;
(S)-2-Phenyl-4-(6-phenyl-pyridin-3-ylmethyl)-morpholine;
(S)-4-(2'-Chloro-5'-methyl-biphenyl-4-ylmethyl)-2-phenyl-morpholine;
(S)-4-[4-(2-Chloro-thiophen-3-yl)-benzyl]-2-phenyl-morpholine;
4'-((S)-2-Phenyl-morpholin-4-ylmethyl)-biphenyl-2-carbonitrile; and
(S)-4-(2'-Chloro-biphenyl-4-ylmethyl)-2-phenyl-morpholine.

Therapeutic Use

As can be demonstrated by the assays described above, the compounds of the invention are useful in modulating the CB2 receptor function. By virtue of this fact, these compounds have therapeutic use in treating disease-states and conditions mediated by the CB2 receptor function or that would benefit from modulation of the CB2 receptor function.

As the compounds of the invention modulate the CB2 receptor function, they have very useful anti-inflammatory and immune-suppressive activity and they can be used in patients as drugs, particularly in the form of pharmaceutical compositions as set forth below, for the treatment of disease-states and conditions.

The agonist, antagonist and inverse agonist compounds according to the invention can be used in patients as drugs for the treatment of the following disease-states or indications that are accompanied by inflammatory processes:

(i) Lung diseases: e.g. asthma, bronchitis, allergic rhinitis, emphysema, adult respiratory distress syndrome (ARDS), pigeon fancier's disease, farmer's lung, chronic obstructive pulmonary disease (COPD), asthma including allergic asthma (atopic or non-atopic) as well as exercise-induced bronchoconstriction, occupational asthma, viral- or bacterial exacerbation of asthma, other non-allergic asthmas and "wheezy-infant syndrome", pneumoconiosis, including aluminosis, anthracosis, asbestosis, chalicosis, ptilosis, siderosis, silicosis, tabacosis and byssinosis;

(ii) Rheumatic diseases or autoimmune diseases or musculoskeletal diseases: all forms of rheumatic diseases, especially rheumatoid arthritis, acute rheumatic fever, and polymyalgia rheumatica; reactive arthritis; rheumatic soft tissue diseases; inflammatory soft tissue diseases of other genesis; arthritic symptoms in degenerative joint diseases (arthroses); tendinitis, bursitis, osteoarthritis, traumatic arthritis; collagenoses of any genesis, e.g., systemic lupus erythematosus, scleroderma, polymyositis, dermatomyositis, Sjögren syndrome, Still disease, Felty syndrome; and osteoporosis and other bone resorption diseases;

(iii) Allergic diseases: all forms of allergic reactions, e.g., angioneurotic edema, hay fever, insect bites, allergic reactions to drugs, blood derivatives, contrast agents, etc., anaphylactic shock (anaphylaxis), urticaria, angioneurotic edema, and contact dermatitis;

(iv) Vascular diseases: panarteritis nodosa, polyarteritis nodosa, periarteritis nodosa, arteritis temporalis, Wegner granulomatosis, giant cell arthritis, atherosclerosis, reperfusion injury and erythema nodosum;

(v) Dermatological diseases: e.g. dermatitis, psoriasis; sunburn, burns, eczema;

(vi) Renal diseases: e.g. nephrotic syndrome; and all types of nephritis, e.g., glomerulonephritis; pancreatits;

(vii) Hepatic diseases: e.g. acute liver cell disintegration; acute hepatitis of various genesis, e.g., viral, toxic, drug-induced; and chronically aggressive and/or chronically intermittent hepatitis;

(viii) Gastrointestinal diseases: e.g. inflammatory bowel diseases, irritable bowel syndrome, regional enteritis (Crohns disease), colitis ulcerosa; gastritis; aphthous ulcer, celiac disease, regional ileitis, gastroesophageal reflux disease;

(ix) Neuroprotection: e.g. in the treatment of neurodegeneration following stroke; cardiac arrest; pulmonary bypass; traumatic brain injury; spinal cord injury or the like;

(x) Eye diseases: allergic keratitis, uveitis, or iritis; conjunctivitis; blepharitis; neuritis nervi optici; choroiditis; glaucoma and sympathetic ophthalmia;

(xi) Diseases of the ear, nose, and throat (ENT) area: e.g. tinnitus; allergic rhinitis or hay fever; otitis externa; caused by contact eczema, infection, etc.; and otitis media;

(xii) Neurological diseases: e.g. brain edema, particularly tumor-related brain edema; multiple sclerosis; acute encephalomyelitis; meningitis; acute spinal cord injury; trauma; dementia, particularly degenerative dementia (including senile dementia, Alzheimer's disease; Parkinson's disease and Creutzfeldt-Jacob disease; Huntington's chorea, Pick's disease; motor neuron disease), vascular dementia (including multi-infarct dementia) as well as dementia associated with intracranial space occupying lesions; infections and related conditions (including HIV infection); Guillain-Barre syndrome; myasthenia gravis, stroke; and various forms of seizures, e.g., nodding spasms;

(xiii) Blood diseases: acquired hemolytic anemia; aplastic anemia, and idiopathic thrombocytopenia;

(xiv) Tumor diseases: acute lymphatic leukemia; Hodgkin's disease, malignant lymphoma; lymphogranulomatoses; lymphosarcoma; solid malignant tumors; extensive metastases;

(xv) Endocrine diseases: endocrine ophthalmopathy; endocrine orbitopathia; thyrotoxic crisis; Thyroiditis de Quervain; Hashimoto thyroiditis; Morbus Basedow; granulomatous thyroiditis; struma lymphomatosa; and Graves disease; type I diabetes (insulin-dependent diabetes);

(xvi) Organ and tissue transplantations and graft-versus-host diseases;

(xvii) Severe states of shock, e.g., septic shock, anaphylactic shock, and systemic inflammatory response syndrome (SIRS);

(xviii) Acute pain such as dental pain, perioperative, postoperative pain, traumatic pain, muscle pain, pain in burned skin, sun burn, trigeminal neuralgia, sun burn; spasm of the gastrointestinal tract or uterus, colics;

(xix) Visceral pain such as pain associated with chronic pelvic pain, pancreatitis, peptic ulcer, interstitial cystitis, renal colic, angina, dysmenorrhoea, menstruation, gynaecological pain, irritable bowel syndrome (IBS), non-ulcer dyspepsia, non-cardiac chest pain, myocardial ischemia;

(xx) Neuropathic pain such as low back pain, non-herpetic neuralgia, post herpetic neuralgia, diabetic neuropathy, nerve injury, acquired immune deficiency syndrome (AIDS) related neuropathic pain, head trauma, painful traumatic mononeuropathy, toxin and chemotherapy induced pain, phantom limb pain, painful polyneuropathy, thalamic pain syndrome, post-stroke pain, central nervous system injury, post surgical pain, stump pain, repetitive motion pain, pain induced by post mastectomy syndrome, multiple sclerosis, root avulsions, postthoracotomy syndrome, neuropathic pain associated hyperalgesia and allodynia.

(xxi) Inflammatory/nociceptive pain induced by or associated with disorders such as osteoarthritis, rheumatoid arthritis, rheumatic disease, teno-synovitis, gout, vulvodynia, myofascial pain (muscular injury, fibromyalgia), tendonitis, osteoarthritis, juvenile arthritis, spondylitis, gouty arthritis, psoriatic arthritis, muscoskeletal pain, fibromyalgia, sprains and strains, sympathetically maintained pain, myositis, pain associated with migraine, toothache, influenza and other viral infections such as the common cold, rheumatic fever, systemic lupus erythematosus;

(xxii) Cancer pain induced by or associated with tumors such as lymphatic leukemia; Hodgkin's disease, malignant lymphoma; lymphogranulomatoses; lymphosarcoma; solid malignant tumors; extensive metastases;

(xxiii) Headache such as cluster headache, migraine with and without aura, tension type headache, headache with different origins, headache disorders including prophylactic and acute use;

(xxiv) various other disease-states or conditions including, restenosis following percutaneous transluminal coronary angioplasty, acute and chronic pain, atherosclerosis, reperfusion injury, congestive heart failure, myocardial infarction, thermal injury, multiple organ injury secondary to trauma, necrotizing enterocolitis and syndromes associated with hemodialysis, leukopheresis, and granulocyte transfusion, sarcoidosis, gingivitis, pyrexia, edema resulting from trauma associated with burns, sprains or fracture, cerebral oedema and angioedema, Diabetes such as diabetic vasculopathy, diabetic neuropathy, diabetic retinopathy, post capillary resistance or diabetic symptoms associated with insulitis (e.g. hypergiycemia, diuresis, proteinuria and increased nitrite and kallikrein urinary excretion).

Other indications include: epilepsy, septic shock e.g. as antihypovolemic and/or antihypotensive agents, cancer, sepsis, osteoporosis, benign prostatic hyperplasia and hyperactive bladder, pruritis, vitiligo, general gastrointestinal disorders, disturbances of visceral motility at respiratory, genitourinary, gastrointestinal or vascular regions, wounds, burns, tissue damage and postoperative fever, syndromes associated with Itching.

Besides being useful for human treatment, these compounds are also useful for veterinary treatment of companion animals, exotic animals and farm animals, including mammals, rodents, and the like.

As noted before, those compounds which are CB2 agonists can also be employed for the treatment of pain.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

Combination Therapy

These compounds may also be employed in combination therapies with the following compounds:

non-steroidal antiinflammatory drugs (NSAIDs) including COX-2 inhibitors such as propionic acid derivatives (alminoprofen, benoxaprofen, bucloxic acid, carprofen, fenhufen, fenoprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (meclofenamic acid, mefe-namic acid, and tolfenamic acid), biphenyl-carboxylic acid derivatives, oxicams (isoxicam, meloxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone), and the coxibs (celecoxib, valecoXID, rofecoxib and etoricoxib);

opiate receptor agonists such as morphine, propoxyphene (Darvon), tramadol, buprenorphin;

sodium channel blockers such as carbamazepine, mexiletine, lamotrigine, pregabaline, tectin, NW-1029, CGX-1002;

N-type calcium channel blockers such as Ziconotide, NMED-160, SPI-860;

serotonergic and noradrenergic modulators such as SR-57746, paroxetine, duloxetine, clonidine, amitriptyline, citalopram;

corticosteroids such as betamethasone, budesonide, cortisone, dexamethasone, hydrocortisone, methylprednisolone, prednisolone, prednisone and triamcinolone;

histamine H1 receptor antagonists such as bromopheniramine, chlorpheniramine, dexchlorpheniramine, triprolidine, clemastine, diphenhydramine, diphenylpyraline, tripelennamine, hydroxyzine, methdiazine, promethazine, trimeprazine, azatadine, cyproheptadine, antazoline, pheniramine pyrilamine, astemizole, terfenadine, loratadine, cetirizine, desloratadine, fexofenadine and levocetirizine;

histamine H2 receptor antagonists such as cimetidine, famotidine and ranitidine;

proton pump inhibitors such as omeprazole, pantoprazole and esomeprazole;

leukotriene antagonists and 5-lipoxygenase inhibitors such as zafirlukast, montelukast, pranlukast and zileuton;

local anesthetics such as ambroxol, lidocaine;

VR1 agonists and antagonists such as NGX-4010, WL-1002, ALGRX-4975, WL-10001, AMG-517;

nicotinic acetylcholine receptor agonists such as ABT-202, A-366833, ABT-594; BTG-102, A-85380, CGX1204;

P2X3 receptor antagonists such as A-317491, ISIS-13920, AZD-9056;

NGF agonists and antagonists such as RI-724, RI-1024, AMG-819, AMG-403, PPH 207;

NK1 and NK2 antagonists such as DA-5018, R-116301; CP-728663, ZD-2249;

NMDA antagonist such as NER-MD-11, CNS-5161, EAA-090, AZ-756, CNP-3381;

potassium channel modulators such as CL-888, ICA-69673, retigabine;

GABA modulators such as lacosamide;

serotonergic and noradrenergic modulators such as SR-57746, paroxetine, duloxetine, clonidine, amitriptyline, citalopram, flibanserin; and combination with anti-migraine drugs like sumatriptan, zolmitriptan, naratriptan, eletriptan.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased inhibitory activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by Remington: The Science and Practice of Pharmacy, 20th Edition, A. Gennaro (ed.), Lippincott Williams & Wilkins, 2000; Handbook of Pharmaceutical Additives, Michael & Irene Ash (eds.), Gower, 1995; Handbook of Pharmaceutical Excipients, A. H. Kibbe (ed.), American Pharmaceutical Ass'n, 2000; H. C. Ansel and N. G. Popovish, Pharmaceutical Dosage Forms and Drug Delivery Systems, 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that is required for the formulation to be efficacious.

Pharmaceutical compositions suitable for buccal (sub-lingual) administration include lozenges comprising a compound of the present invention in a flavored base, usually sucrose, and acacia or tragacanth, and pastilles comprising the compound in an inert base such as gelatin and glycerin or sucrose and acacia.

Pharmaceutical compositions suitable for parenteral administration comprise sterile aqueous preparations of a compound of the present invention. These preparations are preferably administered intravenously, although administration can also be effected by means of subcutaneous, intramuscular, or intradermal injection. Injectable pharmaceutical formulations are commonly based upon injectable sterile saline, phosphate-buffered saline, oleaginous suspensions, or other injectable carriers known in the art and are generally rendered sterile and isotonic with the blood. The injectable pharmaceutical formulations may therefore be provided as a sterile injectable solution or suspension in a nontoxic parenterally acceptable diluent or solvent, including 1,3-butanediol, water, Ringer's solution, isotonic sodium chloride solution, fixed oils such as synthetic mono- or diglycerides, fatty acids such as oleic acid, and the like. Such injectable pharmaceutical formulations are formulated according to the known art using suitable dispersing or setting agents and suspending agents. Injectable compositions will generally contain from 0.1 to 5% w/w of a compound of the invention.

Solid dosage forms for oral administration of the compounds include capsules, tablets, pills, powders, and granules. For such oral administration, a pharmaceutically acceptable composition containing a compound(s) of the invention is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such solid pharmaceutical formulations may include formulations, as are well-known in the art, to provide prolonged or sustained delivery of the drug to the gastrointestinal tract by any number of mechanisms, which include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form.

Liquid dosage forms for oral administration of the compounds include emulsions, microemulsions, solutions, suspensions, syrups, and elixirs, optionally containing pharmaceutical adjuvants in a carrier, such as, for example, water, saline, aqueous dextrose, glycerol, ethanol and the like. These compositions can also contain additional adjuvants such as wetting, emulsifying, suspending, sweetening, flavoring, and perfuming agents.

Topical dosage forms of the compounds include ointments, pastes, creams, lotions, gels, powders, solutions, sprays, inhalants, eye ointments, eye or ear drops, impregnated dressings and aerosols, and may contain appropriate conventional additives such as preservatives, solvents to assist drug penetration and emollients in ointments and creams. Topical application may be once or more than once per day depending upon the usual medical considerations. Furthermore, preferred compounds for the present invention can be administered in intranasal form via topical use of suitable intranasal vehicles. The formulations may also contain compatible conventional carriers, such as cream or ointment bases and ethanol or oleyl alcohol for lotions. Such carriers may be present as from about 1% up to about 98% of the formulation, more usually they will form up to about 80% of the formulation.

Transdermal administration is also possible. Pharmaceutical compositions suitable for transdermal administration can be presented as discrete patches adapted to remain in intimate contact with the epidermis of the recipient for a prolonged period of time. To be administered in the form of a transdermal delivery system, the dosage administration will, of course, be continuous rather than intermittent throughout the dosage regimen. Such patches suitably contain a compound of the invention in an optionally buffered, aqueous solution, dissolved and/or dispersed in an adhesive, or dispersed in a polymer. A suitable concentration of the active compound is about 1% to 35%, preferably about 3% to 15%.

For administration by inhalation, the compounds of the invention are conveniently delivered in the form of an aerosol spray from a pump spray device not requiring a propellant gas or from a pressurized pack or a nebulizer with the use of a suitable propellant, e.g., dichlorodifluoromethane, trichlorofluoromethane, dichlorotetrafluoroethane, tetrafluoroethane, heptafluoropropane, carbon dioxide, or other suitable gas. In any case, the aerosol spray dosage unit may be determined by providing a valve to deliver a metered amount so that the resulting metered dose inhaler (MDI) is used to administer the compounds of the invention in a reproducible and controlled way. Such inhaler, nebulizer, or atomizer devices are known in the prior art, for example, in PCT International Publication Nos. WO 97/12687 (particularly FIG. 6 thereof, which is the basis for the commercial RESPIMAT® nebulizer); WO 94/07607; WO 97/12683; and WO 97/20590, to which reference is hereby made and each of which is incorporated herein by reference in their entireties.

Rectal administration can be effected utilizing unit dose suppositories in which the compound is admixed with low-melting water-soluble or insoluble solids such as fats, cocoa butter, glycerinated gelatin, hydrogenated vegetable oils, mixtures of polyethylene glycols of various molecular weights, or fatty acid esters of polyethylene glycols, or the like. The active compound is usually a minor component, often from about 0.05 to 10% by weight, with the remainder being the base component.

In all of the above pharmaceutical compositions, the compounds of the invention are formulated with an acceptable carrier or excipient. The carriers or excipients used must, of course, be acceptable in the sense of being compatible with the other ingredients of the composition and must not be deleterious to the patient. The carrier or excipient can be a solid or a liquid, or both, and is preferably formulated with the compound of the invention as a unit-dose composition, for example, a tablet, which can contain from 0.05% to 95% by weight of the active compound. Such carriers or excipients include inert fillers or diluents, binders, lubricants, disintegrating agents, solution retardants, resorption accelerators, absorption agents, and coloring agents. Suitable binders include starch, gelatin, natural sugars such as glucose or β-lactose, corn sweeteners, natural and synthetic gums such as acacia, tragacanth or sodium alginate, carboxymethylcellulose, polyethylene glycol, waxes, and the like. Lubricants include sodium oleate, sodium stearate, magnesium stearate, sodium benzoate, sodium acetate, sodium chloride, and the like. Disintegrators include starch, methyl cellulose, agar, bentonite, xanthan gum, and the like.

Pharmaceutically acceptable carriers and excipients encompass all the foregoing additives and the like.

Examples of Pharmaceutical Formulations

A. TABLETS

| Component | Amount per tablet (mg) |
|---|---|
| active substance | 100 |
| lactose | 140 |
| corn starch | 240 |
| polyvinylpyrrolidone | 15 |
| magnesium stearate | 5 |
| TOTAL | 500 |

The finely ground active substance, lactose, and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

B. TABLETS

| Component | Amount per tablet (mg) |
|---|---|
| active substance | 80 |
| lactose | 55 |
| corn starch | 190 |
| polyvinylpyrrolidone | 15 |
| magnesium stearate | 2 |
| microcrystalline cellulose | 35 |
| sodium-carboxymethyl starch | 23 |
| TOTAL | 400 |

The finely ground active substance, some of the corn starch, lactose, microcrystalline cellulose, and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

C. COATED TABLETS

| Component | Amount per tablet (mg) |
|---|---|
| active substance | 5 |
| lactose | 30 |
| corn starch | 41.5 |
| polyvinylpyrrolidone | 3 |
| magnesium stearate | 0.5 |
| TOTAL | 90 |

The active substance, corn starch, lactose, and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

D. CAPSULES

| Component | Amount per capsule (mg) |
|---|---|
| active substance | 50 |
| corn starch | 268.5 |
| magnesium stearate | 1.5 |
| TOTAL | 320 |

The substance and corn starch are mixed and moistened with water. The moist mass is screened and dried. The dry granules are screened and mixed with magnesium stearate. The finished mixture is packed into size 1 hard gelatine capsules.

E. AMPOULE SOLUTION

| Component | Amount per ampoule |
|---|---|
| active substance | 50 mg |
| sodium chloride | 50 mg |
| water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilized and sealed by fusion. The ampoules contain 5 mg, 25 mg, and 50 mg of active substance.

| F. SUPPOSITORIES | |
|---|---|
| Component | Amount per suppository (mg) |
| active substance | 50 |
| solid fat | 1650 |
| TOTAL | 1700 |

The hard fat is melted. At 40° C., the ground active substance is homogeneously dispersed therein. The mixture is cooled to 38° C. and poured into slightly chilled suppository molds.

| G. METERING AEROSOL | |
|---|---|
| Component | Amount |
| active substance | 0.005 |
| sorbitan trioleate | 0.1 |
| Monofluorotrichloromethane and difluorodichloromethane (2:3) | To 100 |

The suspension is transferred into a conventional aerosol container with a metering valve. Preferably, 50 µL of suspension are delivered per spray. The active substance may also be metered in higher doses if desired (e.g., 0.02% by weight).

| H. POWDER FOR INHALATION | |
|---|---|
| Component | Amount |
| active substance | 1.0 mg |
| lactose monohydrate | to 25 mg |

| I. POWDER FOR INHALATION | |
|---|---|
| Component | Amount |
| active substance | 2.0 mg |
| lactose monohydrate | to 25 mg |

| J. POWDER FOR INHALATION | |
|---|---|
| Component | Amount |
| active substance | 1.0 mg |
| lactose monohydrate | to 5 mg |

| K. POWDER FOR INHALATION | |
|---|---|
| Component | Amount |
| active substance | 2.0 mg |
| lactose monohydrate | to 5 mg |

In Examples H, I, J, and K, the powder for inhalation is produced in the usual way by mixing the individual ingredients together.

What is claimed is:

1. A compound of a formula:

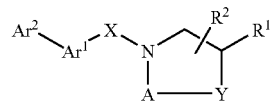

or the pharmaceutically acceptable salts thereof wherein,
$R^1$ is phenyl or benzyl;
$R^2$ is hydrogen or $C_1$-$C_6$ alkyl;
A is a group of the formula —$(CH_2)_n$—, wherein n is 2;
Y is O; or,
X is a methylene group;
$Ar^1$ is 1,4-phenylene; and,
$Ar^2$ is phenyl, which is optionally mono-substituted with chloro, cyano, trifluoromethyl, methoxy or ethoxy or disubstituted with chloro,
or a salt thereof.

2. The compound according to claim 1 wherein said compound is selected from the group consisting of:
2-Phenyl-4-(2'-trifluoromethyl-biphenyl-4-ylmethyl)-morpholine;
4-(2'-Chloro-biphenyl-4-ylmethyl)-2-phenyl-morpholine;
4-(2'-Chloro-5'-methyl-biphenyl-4-ylmethyl)-2-phenyl-morpholine;
4-(2',3'-Dichloro-biphenyl-4-ylmethyl)-2-phenyl-morpholine;
4'-(2-Phenyl-morpholin-4-ylmethyl)-biphenyl-2-carbonitrile;
4-(2'-Ethoxy-biphenyl-4-ylmethyl)-2-phenyl-morpholine;
(S)-4-(2',3'-Dichloro-biphenyl-4-ylmethyl)-2-phenyl-morpholine;
(S)-4-(2'-Chloro-5'-methyl-biphenyl-4-ylmethyl)-2-phenyl-morpholine;
4'-((S)-2-Phenyl-morpholin-4-ylmethyl)-biphenyl-2-carbonitrile; and
(S)-4-(2'-Chloro-biphenyl-4-ylmethyl)-2-phenyl-morpholine;
or the salt thereof.

3. The compound according to claim 1 wherein said compound is selected from the group consisting of:
2-Phenyl-4-(2'-trifluoromethyl-biphenyl-4-ylmethyl)-morpholine;
4-(2'-Chloro-biphenyl-4-ylmethyl)-2-phenyl-morpholine;
4-(2'-Chloro-5'-methyl-biphenyl-4-ylmethyl)-2-phenyl-morpholine;
(S)-4-(2',3'-Dichloro-biphenyl-4-ylmethyl)-2-phenyl-morpholine;
(S)-4-(2'-Chloro-5'-methyl-biphenyl-4-ylmethyl)-2-phenyl-morpholine;
4'-((S)-2-Phenyl-morpholin-4-ylmethyl)-biphenyl-2-carbonitrile; and
(S)-4-(2'-Chloro-biphenyl-4-ylmethyl)-2-phenyl-morpholine;
or the salt thereof.

4. A pharmaceutical composition comprising the compound according to claim 1 or a pharmaceutically acceptable salt thereof and a pharmaceutically acceptable carrier.

* * * * *